US005747660A

United States Patent [19]
Orlicky

[11] Patent Number: 5,747,660
[45] Date of Patent: May 5, 1998

[54] NUCLEIC ACID ENCODING PROSTAGLANDIN $F_{2\alpha}$ RECEPTOR REGULATORY PROTEIN

[75] Inventor: David J. Orlicky, Denver, Colo.

[73] Assignee: The University of Colorado, Boulder, Colo.

[21] Appl. No.: 554,612

[22] Filed: Nov. 6, 1995

[51] Int. Cl.$^6$ ............................ C12N 15/09; C07H 21/00
[52] U.S. Cl. ...................... 536/23.5; 536/24.31; 435/69.1
[58] Field of Search .............................. 536/23.5, 24.31; 435/69.1

[56] References Cited

U.S. PATENT DOCUMENTS 5,211,937  5/1993  Brandley et al. ........................ 424/1.1

OTHER PUBLICATIONS

Orlicky, D., et al., Binding and Second Messengers of Prostaglandins F2α and $E_1$ in Primary Cultures of Rabbit Endometrial Cells, *Journal of Cellular Physiology,* 127:61–72, (1986).

Orlicky, D., et al., Identification and Purification of a Bovine Corpora Luteal membrane Glycoprotein with [$^3$H] Prostaglandins $F_{2A}$ Binding Properties, *Prostaglandin Leukotrienes and Essential Fatty Acids,* 41:51–61, (1990).

Orlicky, D., et al., [$^3$H] Prostaglandin $F_{2\alpha}$ Membrane Binding Reexamine, *Prostaglandins Leukotrienes and Essential Fatty Acids,* 40:181–189, (1990).

Orlicky, D., et al., Immunohistochemical Localization of $PGF_{2\alpha}$ Receptor in the Rat Ovary, *Prostaglandins Leukotrienes and Essential Fatty Acids,* 46:223–229, (1992).

Orlicky, D., et al., Immunohistochemical Localization of $PGF_{2\alpha}$ Receptor in the Mouse Testis, *Prostaglandins Leukotrienes and Essential Fatty Acids,* 47:247–252, (1992).

Orlicky, D., et al., Immunohistochemical Localization of $PGF_{2\alpha}$ Receptor in the Rat Oviduct, *Prostaglandins Leukotrienes and Essential Fatty Acids,* 48:185–192, (1993).

Coleman, R., et al., *Pharmacological Reviews,* vol. 46, No. 2, 205–227.

Sugimoto, Y., et al., Cloning and Expression of a cDNA for Mouse Prostaglandin F Receptor, *The Journal of Biological Chemistry,* vol. 269, No. 2, 1356–1360.

Wieptz, G.J., et al., Receptors for Prostaglandins $F_{2\alpha}$ and $E_2$ in Ovine Corpora Lutea during Maternal Recognition of Pregnancy, *Biology of Reproduction,* 47:984–991, (1992).

*Primary Examiner*—Sally Teng
*Attorney, Agent, or Firm*—Karl Bozicevic; Bozicevic & Reed LLP

[57] ABSTRACT

A new protein is described, prostaglandin $F_{2\alpha}$ receptor regulatory protein (FPRP), which is able to inhibit the binding of prostaglandin $F_{2\alpha}$ ($PGF_{2\alpha}$) to its receptor (FP). Included are pharmaceutical compositions of FPRP and FPRP variants for treatment of $PGF_{2\alpha}$-mediated disorders, and assays for detecting FP in a biological sample.

4 Claims, 13 Drawing Sheets

| | | V | | V | | | | | | | | | | | V | |
| | G | X | X | L | X | C | - LOOP - | D | X | G | X | Y | X | C | X | |
| | | I | | I | | | | | | | | | | | T | |
| | | | | | | | | | | | | | | | A | |
| Consensus | | | | | | | | | | | | | | | | | SEQ ID NO: 3 |
| Loop 1 | G | T | E | L | V | I P | C$_{43}$ -69aa- | D | Q | G | H | K | Y | C$_{119}$ | S T | SEQ ID NO: 4 |
| Loop 2 | G | E | P | F | E | L R | C$_{169}$ -79aa- | D | Q | G | S | Y | R | C$_{247}$ | V | SEQ ID NO: 5 |
| Loop 3 | G | K | D | L | D | L S | C$_{299}$ -73aa- | N | S | G | Y | Y | L | C$_{373}$ | L | SEQ ID NO: 6 |
| Loop 4 | D | D | P | T | E | L Q | C$_{429}$ -85aa- | D | R | G | S | Y | Y | C$_{515}$ | V | SEQ ID NO: 7 |
| Loop 5 | G | N | T | F | E | M T | C$_{571}$ -84aa- | D | A | G | L | Y | R | C$_{655}$ | M V | SEQ ID NO: 8 |
| Loop 6 | G | D | L | I | K | L F | C$_{711}$ -82aa- | D | F | G | N | Y | Y | C$_{793}$ | S V | SEQ ID NO: 9 |

263 Mb
Chromosome 1

```
Rat  GGTTGGGTTT TCTTTTCTAG TGTGTAACAC AAGGATCTGC AGGATTTTCC GTAGA
Hum  ACG.T.AC.. ..C...TA.. ...GC...T. .......... .A........ .....

Rat  CAAAG A--GG-TCTC GTGTATTTTT GTCCCTATCC AAGGTTATAC AAACTAATTG
Hum  ..... .AA..A..T. .......... .A.... ...A. ....T..... T G......

Rat  TGTTGTTTTA TACTGTGGCC ACAAATATTA TGCAATGCAC CATTTGT
Hum  .A........ .......... .A........ .......... .......
```

FIG. 12A

```
Rat  ggaggaggag gaggagcggc ggcggggaag GAGGAGGAGG CGGAGAGTCG CTCCC
Hum  a......... .......a.. .......... .......... G......... .....

Rat  GCCGGCCGAG CATGGGGGCG CCGGCGCG CCG AGGCCGCTGC TGCTGGGGCT CCTAT
Hum  ........G. .......... ...T...CT. .......... .......... ...G.

Rat  CGCTGGgtga gtgcgcgtgg ggcgcggcgg ggcgct
Hum  ...T...... ...c...... ...t.a.... ..a.a
```

FIG. 12B

SEQUENCE LISTING ( 1 ) GENERAL INFORMATION:

( i i i ) NUMBER OF SEQUENCES: 51

( 2 ) INFORMATION FOR SEQ ID NO:1:

( i ) SEQUENCE CHARACTERISTICS:
      ( A ) LENGTH: 879 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:1:

```
Met Gly Arg Pro Ala Pro Arg Pro Leu Leu Leu Ala Leu Leu Ser Leu
 1               5                  10                  15

Ala Val Cys Arg Gly Arg Val Val Arg Val Pro Ala Gly Thr Leu Val
            20                  25                  30

Arg Val Val Gly Thr Glu Leu Val Ile Pro Cys Asn Val Ser Asp Tyr
        35                  40                  45

Asp Gly Pro Ser Glu Gln Asn Phe Asp Trp Ser Phe Ser Ser Ser Gly
    50                  55                  60

Ser Ser Phe Val Glu Leu Ala Ser Thr Trp Glu Val Gly Phe Pro Ala
65                  70                  75                  80

Gln Gln Tyr Arg Glu Arg Leu Gln Arg Gly Asp Ile Leu Leu Arg Arg
                85                  90                  95

Thr Ala Asn Asp Ala Val Glu Leu His Ile Lys Asn Val Gln Pro Ser
            100                 105                 110

Asp Gln Gly His Tyr Lys Cys Ser Thr Pro Ser Thr Asp Ala Thr Val
        115                 120                 125

Gln Gly Asn Tyr Glu Asp Thr Met Gln Val Lys Val Leu Ala Asp Ala
    130                 135                 140

Leu Val Val Gly Pro Ser Ser Arg Pro Pro Pro Gly Leu Ser Leu Arg
145                 150                 155                 160

Glu Gly Glu Pro Phe Glu Leu Arg Cys Ile Ala Ser Thr Thr Ser Pro
                165                 170                 175

Leu His Thr His Leu Ala Leu Arg Trp Glu Leu His Arg Gly Pro Val
            180                 185                 190

His Arg Ser Ile Leu Ala Leu Ser His Glu Gly Arg Phe His Pro Gly
        195                 200                 205

Pro Gly Tyr Glu Gln Arg Tyr His Ser Gly Asp Val Arg Leu Asp Thr
    210                 215                 220

Val Gly Ser Asp Ala Tyr Arg Leu Ser Val Ala Arg Ala Leu Ser Ala
225                 230                 235                 240

Asp Gln Gly Ser Tyr Arg Cys Val Val Ser Glu Trp Ile Thr Glu Gln
                245                 250                 255

Gly Ser Trp Gln Glu Ile Gln Glu Lys Ala Val Glu Val Ala Thr Val
            260                 265                 270

Val Ile Gln Pro Thr Ala Leu Gln Leu Ala Val Pro Arg Thr Val Ser
        275                 280                 285

Val Thr Glu Gly Lys Asp Leu Asp Leu Ser Cys Asn Ile Thr Thr Asp
    290                 295                 300

Arg Val Asp Asp Val Arg Pro Glu Val Thr Trp Tyr Phe Lys Lys Thr
305                 310                 315                 320

Pro Asp Thr Ser Leu Leu Ala Ser His Met Leu Ala Arg Leu Asp Arg
```

-continued

|  |  |  |  |  |  | 325 |  |  |  | 330 |  |  |  | 335 |  |
|---|---|---|---|---|---|---|---|---|---|---|---|---|---|---|---|
| Asp | Ser | Leu | Val | His | Ser | Ser | Pro | His | Val | Ala | Leu | Ser | His | Val | Asp |
|  |  |  | 340 |  |  |  |  | 345 |  |  |  |  | 350 |  |  |
| Thr | Arg | Ser | Tyr | His | Leu | Leu | Val | Arg | Asp | Val | Ser | Lys | Glu | Asn | Ser |
|  |  | 355 |  |  |  |  | 360 |  |  |  |  | 365 |  |  |  |
| Gly | Tyr | Tyr | Leu | Cys | Leu | Val | Ala | Leu | Trp | Ala | Pro | Gly | His | Asn | Arg |
|  |  | 370 |  |  |  |  | 375 |  |  |  | 380 |  |  |  |  |
| Ser | Trp | His | Lys | Val | Ala | Glu | Ala | Met | Ser | Ala | Pro | Ser | Gly | Val | Ser |
| 385 |  |  |  |  | 390 |  |  |  |  | 395 |  |  |  |  | 400 |
| Val | Thr | Trp | Leu | Glu | Pro | Glu | Tyr | Gln | Val | Tyr | Leu | Asn | Ala | Ser | Lys |
|  |  |  |  | 405 |  |  |  |  | 410 |  |  |  |  | 415 |  |
| Val | Pro | Gly | Phe | Ser | Asp | Asp | Pro | Thr | Glu | Leu | Gln | Cys | Arg | Val | Ile |
|  |  |  | 420 |  |  |  |  | 425 |  |  |  |  | 430 |  |  |
| Asp | Thr | Lys | Arg | Val | Asp | Ala | Gly | Val | Arg | Leu | Thr | Val | Ser | Trp | Tyr |
|  |  | 435 |  |  |  |  | 440 |  |  |  |  | 445 |  |  |  |
| Tyr | Arg | Met | Asn | Arg | Arg | Asn | Asp | Asp | Val | Val | Ala | Ser | Glu | Leu | Leu |
|  | 450 |  |  |  |  | 455 |  |  |  |  | 460 |  |  |  |  |
| Ala | Val | Met | Asp | Gly | Asp | Trp | Thr | Leu | Arg | Tyr | Gly | Glu | Arg | Ser | Lys |
| 465 |  |  |  |  | 470 |  |  |  |  | 475 |  |  |  |  | 480 |
| Gln | Arg | Ala | Gln | Asp | Gly | Glu | Phe | Ile | Phe | Ser | Lys | Glu | His | Thr | Asp |
|  |  |  |  | 485 |  |  |  |  | 490 |  |  |  |  | 495 |  |
| Thr | Phe | Ser | Phe | Arg | Ile | Gln | Arg | Thr | Glu | Glu | Asp | Arg | Gly | Ser |
|  |  |  | 500 |  |  |  |  | 505 |  |  |  |  | 510 |  |  |
| Tyr | Tyr | Cys | Val | Val | Ser | Ala | Trp | Thr | Arg | Gln | Arg | Asn | Ser | Ser | Trp |
|  |  | 515 |  |  |  |  | 520 |  |  |  |  | 525 |  |  |  |
| Val | Lys | Ser | Lys | Asp | Val | Phe | Ser | Lys | Pro | Val | Asn | Ile | Phe | Trp | Ala |
|  | 530 |  |  |  |  | 535 |  |  |  |  | 540 |  |  |  |  |
| Ser | Glu | Asp | Ser | Val | Leu | Val | Val | Lys | Ala | Arg | Gln | Pro | Lys | Pro | Phe |
| 545 |  |  |  |  | 550 |  |  |  |  | 555 |  |  |  |  | 560 |
| Phe | Ala | Ala | Gly | Asn | Thr | Phe | Glu | Met | Thr | Cys | Lys | Val | Ser | Ser | Lys |
|  |  |  |  | 565 |  |  |  |  | 570 |  |  |  |  | 575 |  |
| Asn | Ile | Lys | Ser | Pro | Arg | Tyr | Ser | Val | Leu | Ile | Thr | Ala | Glu | Lys | Pro |
|  |  |  | 580 |  |  |  |  | 585 |  |  |  |  | 590 |  |  |
| Val | Gly | Asp | Leu | Ser | Ser | Pro | Asn | Glu | Thr | Lys | Tyr | Ile | Ile | Ser | Leu |
|  |  | 595 |  |  |  |  | 600 |  |  |  |  | 605 |  |  |  |
| Asp | Gln | Asp | Ser | Val | Val | Lys | Leu | Glu | Asn | Trp | Thr | Asp | Ala | Ser | Arg |
|  | 610 |  |  |  |  | 615 |  |  |  |  | 620 |  |  |  |  |
| Val | Asp | Gly | Val | Val | Leu | Glu | Lys | Val | Gln | Glu | Asp | Glu | Phe | Arg | Tyr |
| 625 |  |  |  |  | 630 |  |  |  |  | 635 |  |  |  |  | 640 |
| Arg | Met | Tyr | Gln | Thr | Gln | Val | Ser | Asp | Ala | Gly | Leu | Tyr | Arg | Cys | Met |
|  |  |  |  | 645 |  |  |  |  | 650 |  |  |  |  | 655 |  |
| Val | Thr | Ala | Trp | Ser | Pro | Ile | Gly | Gly | Ser | Leu | Trp | Arg | Glu | Ala | Ala |
|  |  |  | 660 |  |  |  |  | 665 |  |  |  |  | 670 |  |  |
| Thr | Ser | Leu | Ser | Asn | Pro | Ile | Glu | Ile | Asp | Phe | Gln | Thr | Ser | Gly | Pro |
|  |  | 675 |  |  |  |  | 680 |  |  |  |  | 685 |  |  |  |
| Ile | Phe | Asn | Ala | Ser | Val | His | Ser | Asp | Thr | Leu | Ser | Val | Thr | Arg | Gly |
|  | 690 |  |  |  |  | 695 |  |  |  |  | 700 |  |  |  |  |
| Asp | Leu | Ile | Lys | Leu | Phe | Cys | Ile | Val | Thr | Val | Asp | Gly | Ala | Val | Leu |
| 705 |  |  |  |  | 710 |  |  |  |  | 715 |  |  |  |  | 720 |
| Asp | Pro | Asp | Asp | Met | Ala | Phe | Asp | Val | Ser | Trp | Phe | Ala | Val | His | Ser |
|  |  |  |  | 725 |  |  |  |  | 730 |  |  |  |  | 735 |  |
| Phe | Gly | Leu | Asp | Lys | Ala | Pro | Ile | Leu | Leu | Ser | Ser | Leu | Asp | Arg | Lys |
|  |  |  | 740 |  |  |  |  | 745 |  |  |  |  | 750 |  |  |

| | | | | | | | | | | | | | |
|---|---|---|---|---|---|---|---|---|---|---|---|---|---|
| Gly | Val | Val 755 | Thr | Thr | Gly | Gln | Arg 760 | Asp | Trp | Lys | Ser | Thr 765 | Val | Ser | Leu |
| Glu | Arg 770 | Val | Ser | Val | Leu | Glu 775 | Phe | Leu | Leu | Gln | Val 780 | His | Gly | Ser | Glu |
| Asp 785 | Gln | Asp | Phe | Gly | Asn 790 | Tyr | Tyr | Cys | Ser | Val 795 | Thr | Pro | Trp | Val | Arg 800 |
| Ser | Pro | Thr | Gly | Ser 805 | Trp | Gln | Arg | Glu | Ala 810 | Glu | Ile | His | Ser | Arg 815 | Pro |
| Ile | Phe | Ile | Thr 820 | Val | Lys | Met | Asp | Val 825 | Leu | Asn | Ala | Phe | Lys 830 | Tyr | Pro |
| Leu | Leu | Ile 835 | Gly | Val | Gly | Leu | Ser 840 | Thr | Val | Ile | Arg | Leu 845 | Leu | Ser | Cys |
| Leu | Ile 850 | Gly | Tyr | Cys | Ser | Ser 855 | His | Trp | Cys | Cys | Lys 860 | Lys | Glu | Val | Arg |
| Glu 865 | Thr | Arg | Arg | Glu | Arg 870 | Arg | Arg | Leu | Met | Ser 875 | Met | Glu | Met | Asp |

(2) INFORMATION FOR SEQ ID NO:2:

(i) SEQUENCE CHARACTERISTICS:
        (A) LENGTH: 5843 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:2:

```
CAGCGCCCAG GAGGAGGAGG CGGAGAGTCG CTCCCGCCGG CCGAGCATGG GGCGCCCGGC          60
GCCGAGGCCG CTGCTGCTGG CGCTCCTATC GCTGGCTGTC TGCCGCGGGC GTGTGGTGAG         120
AGTCCCTGCG GGCACCCTGG TTCGAGTGGT GGGCACTGAG CTGGTGATCC CCTGCAATGT         180
CAGTGACTAT GATGGCCCCA GTGAGCAAAA CTTTGACTGG AGCTTCTCGT CTTCGGGAAG         240
CAGCTTTGTG GAGCTCGCCA GCACCTGGGA GGTGGGCTTC CCGGCGCAGC AGTACCGTGA         300
GCGGCTGCAG CGGGGCGACA TCCTGTTGAG GAGGACAGCC AATGATGCTG TGGAGCTGCA         360
CATAAAGAAT GTCCAGCCCT CGGACCAAGG CCACTACAAG TGTTCAACTC CAAGCACAGA         420
CGCCACCGTC CAGGGCAACT ATGAGGACAC ARTGCAGGTT AAAGTGCTGG CAGATGCCCT         480
GGTGGTGGGC CCCAGCTCCC GGCCTCCTCC AGGCCTGAGC CTGCGCGAGG GGGAGCCCTT         540
TGAACTTCGA TGTATCGCAT CTACTACGTC ACCGTTGCAC ACACACCTGG CACTTCGGTG         600
GGAACTGCAC CGTGGCCCAG TGCACCGAAG CATCCTAGCC CTAAGCCACG AGGGCAGGTT         660
TCACCCAGGA CCTGGCTATG AACAGCGCTA CCACAGTGGG GATGTACGCC TGGACACGGT         720
GGGCAGCGAT GCCTACCGCC TCTCCGTAGC CCGGGCACTC TCTGCAGACC AGGGTTCCTA         780
CAGATGTGTG GTCAGTGAGT GGATCACAGA GCAAGGCAGC TGGCAAGAAA TCCAAGAAAA         840
AGCTGTGGAA GTGGCCACTG TGGTGATCCA GCCAACAGCT CTGCAACTGG CCGTGCCCAG         900
GACAGTGTCT GTGACCGAAG GAAAGGACCT GGACCTTTCT TGCAACATCA CAACAGACCG         960
TGTGGATGAT GTCCGGCCTG AGGTGACATG GTACTTCAAA AAGACACCCG ATACCTCTTT        1020
GCTTGCCTCC CATATGCTGG CTCGGCTGGA CCGTGATTCC CTGGTACACA GCTCACCACA        1080
CGTTGCTCTC AGCCACGTGG ATACCCGCTC TTACCATCTA CTGGTGCGAG ATGTTAGCAA        1140
AGAAAACTCC GGTTACTATC TATGCCTCGT GGCCCTCTGG GCTCCTGGAC ACAACCGGAG        1200
CTGGCACAAG GTGGCAGAGG CCATGTCTGC CCCATCTGGT GTAAGCGTGA CCTGGCTAGA        1260
ACCAGAATAC CAGGTCTACC TGAATGCTTC TAAGGTCCCC GGGTTTTCCG ACGACCCCAC        1320
```

```
AGAACTGCAA TGCCGGGTGA TAGACACGAA GCGTGTGGAT GCCGGTGTCC GACTTACTGT   1380
GTCGTGGTAC TATAGAATGA ACCGTCGCAA TGATGACGTG GTGGCCAGCG AGCTTCTCGC   1440
CGTCATGGAC GGGGACTGGA CTCTGAGATA CGGGGAGAGA AGCAAACAGC GGGCCCAGGA   1500
CGGCGAGTTT ATCTTTTCTA AGGAGCACAC AGACACATTC AGTTTCCGGA TCCAAAGGAC   1560
TACGGAGGAA GACAGGGGCA GTTATTACTG TGTTGTGTCT GCCTGGACCA GGCAGAGGAA   1620
CAGCAGCTGG GTGAAGAGCA AAGATGTCTT CTCCAAGCCC GTCAACATAT TCTGGGCCTC   1680
GGAAGATTCT GTGCTCGTGG TGAAGGCACG GCAGCCAAAG CCTTTCTTTG CTGCAGGGAA   1740
TACATTTGAG ATGACTTGCA AAGTGTCTTC CAAGAATATT AAGTCTCCAC GATACTCTGT   1800
TCTCATCACG GCTGAGAAGC CTGTTGGGGA CCTCTCCAGT CCCAATGAAA CCAAGTACAT   1860
CATCTCCCTG GACCAGGATT CCGTGGTGAA GCTGGAGAAC TGGACCGACG CATCTCGGGT   1920
GGACGGCGTC GTGTTAGAGA AGGTTCAAGA GGATGAGTTC CGATACCGAA TGTACCAGAC   1980
TCAGGTCTCC GATGCGGGCC TGTACCGCTG CATGGTGACA GCCTGGTCTC CTATCGGGGG   2040
CAGCTTGTGG CGAGAGGCAG CGACCAGTCT TTCCAATCCT ATTGAGATTG ACTTCCAAAC   2100
CTCAGGTCCC ATATTTAACG CCTCTGTGCA TTCAGACACT CTGTCCGTCA CCCGGGGAGA   2160
TCTCATCAAG TTGTTCTGTA TCGTCACTGT GGACGGAGCA GTGCTGGACC CAGATGACAT   2220
GGCCTTCGAT GTATCCTGGT TTGCAGTACA CTCTTTTGGC TTGGACAAGG CTCCCATCCT   2280
CCTATCCTCC TTGGACCGGA AGGGAGTCGT GACTACAGGC CAGAGGGACT GGAAGAGTAC   2340
CGTCAGCCTG GAGCGAGTGA GCGTGCTGGA ATTTTGCTG CAAGTGCATR GCTCTGAGGA   2400
CCAGGACTTT GGCAACTACT ATTGTTCTGT GACTCCCTGG GTGAGGTCAC CAACTGGTTC   2460
CTGGCAGAGG GAAGCCGAGA TCCACTCCAG GCCCATCTTT ATAACTGTGA AGATGGATGT   2520
GCTGAACGCC TTCAAGTACC CGCTGCTGAT CGGCGTGGGC CTGTCCACAG TCATCSGGCT   2580
CCTGTCCTGC CTCATTGGGT ACTGCAGTTC CCATTGGTGC TGTAAGAAGG AGGTGCGGGA   2640
GACGCGTCGG GAGCGCCGCA GGCTCATGTC CATGGAGATG GATTAAGCAG TTGGAGGGAC   2700
AGAGGAACGT TGTAGGAGCA GTGGGGTGGG GGGTGAGAAG AGGACTCTGA GATTTTACAA   2760
CCGAGTGTGT TACACTAAAA CCGGTCCTCT CTAATCTCAG GTGGGACTCA GCGCTCTCTC   2820
TTTTCTGCAT GTCAAGTTCC GAGCGCGGAC ATGTTTACCA GCACACGGCT CTTCTTCCCA   2880
CGGCACTTTC TGATATGTAA CAATCGAGTG TGTGTCTCCC CCCCCCGCT GAAGCTGTTT    2940
AATGGTTAAC CCCCGTCTAA TTAGTTTTCT CCTAGCAGCT TATCGATCCT CTGATTCACG   3000
TGTGTTGATC ACTTTTGATT TAAGGGATCG CAGTGAGGAA GGGCGAAAGC ATTCAGAGTT   3060
GGTCATCATG AGTAAGAGGG TACCTGCCCA CCCGAAAGCC AGCATCCACA AGCAGCCATC   3120
TGGAGAGCTG CTACCTGCTG CTCTCTACCC TGGCCCAGAA CTGATAGAGA CCTGTGCCAA   3180
GGCAAGCTGT GGCTATGACT ACCCTGCCCA TCCCCATTG TCAGGAGTTT AAACTATATT    3240
GGAACCTAAA CTCTATAACT TCTTGACCCC ATAAGCCTTT TGTTTCCCTT TCTCCTCTAC   3300
CCTCTTCTGT TTTCGGGTTT GTTTCTGTGA GAGTGAGGAT ATGGCAGCCC TGGAGTCTAG   3360
AATTTGGCTT TCCACCAAGC ACCTTATCTC GCCACCTTAG CCTTAAGAAT GAGTATGAAG   3420
AAAAATCCAC CACCACCTCT GTCCAGGGCA GGTCTGTGAG GAGAGGACAC TGGGGAAGGA   3480
AAGGCACAGA TGCTTGCTTA CTTGCTCACT CTGTAGTTCT GAGGCCGCTG TGCCTGCTCC   3540
AGGAATCCAA GGGTGAGTGG GAGCAGAGGG CATCTGAGTT GTGCCGCTGA GCCAGGTGCC   3600
CTGTCCCTTC ATGAGAGGCA CTGTCCCTTG TACCCCCAGG ACCAGCATGG GAGCCACAAA   3660
TGTGCCACAT TGAGCTCCTT CCCAGGAAGG CAGATTGCTG CCTGCCAGAC TGACTGACTT   3720
```

```
CAAGGAATCA GAAATTGCCT GGAGCAAGCG TGTGTTCTCT GTGACCTTTT TCAGTCCTTG   3780
AAGTCTTTTT AAGATCCCCG CAGGGGGTGG TGAAGAGGGG TATACTTTGT GGACGGTTTG   3840
CTTTCCTATT AGAAACACAA AGGGAACCCA GCAATTTAGT GTTATGTGAA TGGCCTGTAA   3900
AATAGGATTG AAGGCAGCCG GCTCTGCCTG ACTGGGCCCA GCAGGAATAG GACAGAGGGC   3960
AGGCACACCT TCCAGGTCAC CAGTGCCTGC TCCATCAGGG CCTCAGCCAT GCAAAGTCTC   4020
TCGCCCTAGC ATAGCCTTCC AGGAGCCTCC GATAGGTACT GAGGCTCATC AGCCACCCGG   4080
TACCCTCACC CTACCCTCTA CCTCTGAAGG ATTAACATT  GTTGTCTTCC AAAGGGGAGT   4140
GGGGGAGGAG AGCTCCTTTC TCTTAAGCAA TAAAGTAATA AGAAAAGATG GCCATTCACG   4200
GGCAGCTCTA GTCACCATGG GACCGGATGC GCTGAGCTCC CCCCTCCCCA CCTTCTCTCC   4260
ATGTGGCCCA TGGTGGCTTT TGTATTTGCC ACCCAGTTTC CTCTGCTTGT TTCGAGCCCA   4320
CCTTGGAGAC TGCTCTTATG ATGAGATTCT GAGCCGGTGG CTCTAGCCCA GGTGGGGGGT   4380
ACAGGTTTAG AGTCGGTAGC AAGAAGAGGG ACAGCAGGTG CACCCCACAC AAGCAAGAGA   4440
GGCCAGAGAA AGAGGGGAGG CTTCGGAAGA CATGGCTGTT CTACATGTCG CTCTCTTATT   4500
GCTAGCTCAG ACGTGAGGCA CAGGTGACTG TACAAACAGG AATTAGGGGA GTAGAACCAA   4560
GTATTAGGAA CTTCAAGCCT GTGCCATTAC TGGAGAAGAT TCAGGGCCTT TGCAGTGCAG   4620
CCCTCCTTAG GAGGACAAGA GAGATTTAGC CTTGGATGAG TTGAGGTGAG CCCTAGCTGT   4680
ACATGAACCC ACAGAGGTCC AAGCGGGTAA CTGATGGTGA GAGATGAGTG ATCGGTCCTA   4740
CCTTCCCCTT TCCCTTTTGT CTGATGTTGA GATTTGAACC TGAGTTGTGG AGGTCATGCC   4800
CAAACCCCTC CATGTTGCTT AGGGCTGGAA GAGGGACCAG AAACCCCAGG ACCTAGTTCC   4860
TTTTGGGAAT ATTGGCATTC TGGGGTATGT GTCTTTTTAA GTGTGGTCAA ACACTCTTGA   4920
TGTACCAAAT AGTGTTCCCC GTGAAGCGCT CTTCCTGAGG CTCCCACCCA GCAACACTGG   4980
TCTGAGGGAA GGAAAGGCCA AACCAGGCCT GGGCACATGA AATTGCACTT CTTAAAGAGA   5040
AACTTTTTAG AAGGTTGGGT ATTTTCTTA  ATCACAAAAA TCTCCCACTG AAAGAACCTA   5100
AGCTACATTC AGATCGAAGC CTCTAAATTA AATTGTTTAC TTTACAATGT TTACACACAT   5160
GACTCACTTT TTTAGAAAAA TAAGAAAACT GCAAACTCCG GCTTTTTAAC AACTTTTCAG   5220
CTTTTTCATG CATGGGATAG ATATGCTGGC AACCTGACTC ACCAGCTGGA TCAAATCCTC   5280
ATTTAGAAAT GTCCCGATAT GTGGATATAT GTGTCTTCCC CCCTCCCAAC CACACAGCTC   5340
CCTCCTGCCC AGACCTCTGT CTGTTTCTCT GGTGGCTTTT GCCTCCTGCT TTGCAGACCG   5400
CCTGCAGCCA TGATTTTGTT ACGGCATCCA CGAGCCAAAG ACTGCGCCTT GGGAGCAGGA   5460
ACAATAAGCA ATACTACACC ACTCGCTACT GTCGGGGGTC TTTTTCTCTT TCTTTTCTTT   5520
TTTAGCTTCA CTGATGGCAA CAGAGGAAGA AAGGAATTGA GGTTTAGGCA AGTTCTCTTC   5580
CCCTGTGTGA CCAGATTCTC GGTGACACAC AGTTGTGCAG ATCACTAGGA GAACAAGGTT   5640
GGGTTTTCTT TTCTAGTGTG TAACACAAGG ATCTGCAGGA TTTTCCGTAG ACAAAGAGGT   5700
CTCGTGTATT TTTGTCCCTA TCCAAGGTTA TACAAACTAA TTGTGTTGTT TTATACTGTG   5760
GCCACAAATA TTATGCAATG CACCATTTGT TTTGTTTTT  ATTTATTAA  AGGAAATTTA   5820
ATTTAAAAAA AAAAAAAAAA AAA                                          5843
```

( 2 ) INFORMATION FOR SEQ ID NO:3:

( i ) SEQUENCE CHARACTERISTICS:
        ( A ) LENGTH: 86 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:3:

| Gly | Xaa | Xaa | Xaa | Xaa | Xaa | Xaa | Cys | Xaa | Xaa | Xaa | Xaa | Xaa | Xaa | Xaa |
|---|---|---|---|---|---|---|---|---|---|---|---|---|---|---|
| | | | | 5 | | | | | 10 | | | | | 15 |

| Xaa | Xaa | Xaa | Xaa | Xaa | Xaa | Xaa | Xaa | Xaa | Xaa | Xaa | Xaa | Xaa | Xaa | Xaa |
|---|---|---|---|---|---|---|---|---|---|---|---|---|---|---|
| | | | | 20 | | | | | 25 | | | | | 30 |

| Xaa | Xaa | Xaa | Xaa | Xaa | Xaa | Xaa | Xaa | Xaa | Xaa | Xaa | Xaa | Xaa | Xaa | Xaa |
|---|---|---|---|---|---|---|---|---|---|---|---|---|---|---|
| | | | 35 | | | | | 40 | | | | | 45 | |

| Xaa | Xaa | Xaa | Xaa | Xaa | Xaa | Xaa | Xaa | Xaa | Xaa | Xaa | Xaa | Xaa | Xaa | Xaa |
|---|---|---|---|---|---|---|---|---|---|---|---|---|---|---|
| | 50 | | | | | 55 | | | | | 60 | | | |

| Xaa | Xaa | Xaa | Xaa | Xaa | Xaa | Xaa | Xaa | Xaa | Xaa | Xaa | Xaa | Xaa | Asp | Xaa | Gly |
|---|---|---|---|---|---|---|---|---|---|---|---|---|---|---|---|
| 65 | | | | | 70 | | | | | 75 | | | | | 80 |

| Xaa | Tyr | Xaa | Cys | Xaa | Xaa |
|---|---|---|---|---|---|
| | | | | 85 | |

( 2 ) INFORMATION FOR SEQ ID NO:4:

( i ) SEQUENCE CHARACTERISTICS:
        ( A ) LENGTH: 85 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:4:

| Gly | Thr | Glu | Leu | Val | Ile | Pro | Cys | Xaa | Xaa | Xaa | Xaa | Xaa | Xaa | Xaa |
|---|---|---|---|---|---|---|---|---|---|---|---|---|---|---|
| | | | | 5 | | | | | 10 | | | | | 15 |

| Xaa | Xaa | Xaa | Xaa | Xaa | Xaa | Xaa | Xaa | Xaa | Xaa | Xaa | Xaa | Xaa | Xaa | Xaa |
|---|---|---|---|---|---|---|---|---|---|---|---|---|---|---|
| | | | | 20 | | | | | 25 | | | | | 30 |

| Xaa | Xaa | Xaa | Xaa | Xaa | Xaa | Xaa | Xaa | Xaa | Xaa | Xaa | Xaa | Xaa | Xaa | Xaa |
|---|---|---|---|---|---|---|---|---|---|---|---|---|---|---|
| | | | 35 | | | | | 40 | | | | | 45 | |

| Xaa | Xaa | Xaa | Xaa | Xaa | Xaa | Xaa | Xaa | Xaa | Xaa | Xaa | Xaa | Xaa | Xaa | Xaa |
|---|---|---|---|---|---|---|---|---|---|---|---|---|---|---|
| | 50 | | | | | 55 | | | | | 60 | | | |

| Xaa | Xaa | Xaa | Xaa | Xaa | Xaa | Xaa | Xaa | Xaa | Xaa | Xaa | Xaa | Asp | Gln | Gly | His |
|---|---|---|---|---|---|---|---|---|---|---|---|---|---|---|---|
| 65 | | | | | 70 | | | | | 75 | | | | | 80 |

| Lys | Tyr | Cys | Ser | Thr |
|---|---|---|---|---|
| | | | | 85 |

( 2 ) INFORMATION FOR SEQ ID NO:5:

( i ) SEQUENCE CHARACTERISTICS:
        ( A ) LENGTH: 96 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:5:

| Gly | Glu | Pro | Phe | Glu | Leu | Arg | Cys | Xaa | Xaa | Xaa | Xaa | Xaa | Xaa | Xaa |
|---|---|---|---|---|---|---|---|---|---|---|---|---|---|---|
| | | | | 5 | | | | | 10 | | | | | 15 |

| Xaa | Xaa | Xaa | Xaa | Xaa | Xaa | Xaa | Xaa | Xaa | Xaa | Xaa | Xaa | Xaa | Xaa | Xaa |
|---|---|---|---|---|---|---|---|---|---|---|---|---|---|---|
| | | | | 20 | | | | | 25 | | | | | 30 |

| Xaa | Xaa | Xaa | Xaa | Xaa | Xaa | Xaa | Xaa | Xaa | Xaa | Xaa | Xaa | Xaa | Xaa | Xaa |
|---|---|---|---|---|---|---|---|---|---|---|---|---|---|---|
| | | | 35 | | | | | 40 | | | | | 45 | |

| Xaa | Xaa | Xaa | Xaa | Xaa | Xaa | Xaa | Xaa | Xaa | Xaa | Xaa | Xaa | Xaa | Xaa | Xaa |
|---|---|---|---|---|---|---|---|---|---|---|---|---|---|---|
| | 50 | | | | | 55 | | | | | 60 | | | |

| Xaa | Xaa | Xaa | Xaa | Xaa | Xaa | Xaa | Xaa | Xaa | Xaa | Xaa | Xaa | Xaa | Xaa | Xaa |
|---|---|---|---|---|---|---|---|---|---|---|---|---|---|---|
| 65 | | | | | 70 | | | | | 75 | | | | | 80 |

```
Xaa Xaa Xaa Xaa Xaa Xaa Xaa Asp Gln Gly Ser Tyr Arg Cys Val Val
            85                  90                      95
```

( 2 ) INFORMATION FOR SEQ ID NO:6:

( i ) SEQUENCE CHARACTERISTICS:
        ( A ) LENGTH: 90 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:6:

```
Gly Lys Asp Leu Asp Leu Ser Cys Xaa Xaa Xaa Xaa Xaa Xaa Xaa
                5                   10                      15
Xaa Xaa Xaa Xaa Xaa Xaa Xaa Xaa Xaa Xaa Xaa Xaa Xaa Xaa Xaa
            20                  25                      30
Xaa Xaa Xaa Xaa Xaa Xaa Xaa Xaa Xaa Xaa Xaa Xaa Xaa Xaa Xaa
            35                  40                      45
Xaa Xaa Xaa Xaa Xaa Xaa Xaa Xaa Xaa Xaa Xaa Xaa Xaa Xaa Xaa
        50                  55                      60
Xaa Xaa Xaa Xaa Xaa Xaa Xaa Xaa Xaa Xaa Xaa Xaa Xaa Xaa Xaa
65                  70                      75                  80
Xaa Asn Ser Gly Tyr Tyr Leu Cys Leu Val
            85                  90
```

( 2 ) INFORMATION FOR SEQ ID NO:7:

( i ) SEQUENCE CHARACTERISTICS:
        ( A ) LENGTH: 102 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:7:

```
Asp Asn Pro Thr Glu Leu Gln Cys Xaa Xaa Xaa Xaa Xaa Xaa Xaa
                5                   10                      15
Xaa Xaa Xaa Xaa Xaa Xaa Xaa Xaa Xaa Xaa Xaa Xaa Xaa Xaa Xaa
            20                  25                      30
Xaa Xaa Xaa Xaa Xaa Xaa Xaa Xaa Xaa Xaa Xaa Xaa Xaa Xaa Xaa
            35                  40                      45
Xaa Xaa Xaa Xaa Xaa Xaa Xaa Xaa Xaa Xaa Xaa Xaa Xaa Xaa Xaa
        50                  55                      60
Xaa Xaa Xaa Xaa Xaa Xaa Xaa Xaa Xaa Xaa Xaa Xaa Xaa Xaa Xaa
65                  70                      75                  80
Xaa Xaa Xaa Xaa Xaa Xaa Xaa Xaa Xaa Xaa Xaa Xaa Xaa Asp Arg Gly
            85                  90                      95
Ser Tyr Tyr Cys Val Val
            100
```

( 2 ) INFORMATION FOR SEQ ID NO:8:

( i ) SEQUENCE CHARACTERISTICS:
        ( A ) LENGTH: 101 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:8:

```
Gly Xaa Thr Phe Glu Met Thr Cys Xaa Xaa Xaa Xaa Xaa Xaa Xaa
                5                   10                      15
```

| Xaa | Xaa | Xaa | Xaa | Xaa | Xaa | Xaa | Xaa | Xaa | Xaa | Xaa | Xaa | Xaa | Xaa | Xaa |
|     |     |     | 20  |     |     |     |     | 25  |     |     |     |     | 30  |     |

| Xaa | Xaa | Xaa | Xaa | Xaa | Xaa | Xaa | Xaa | Xaa | Xaa | Xaa | Xaa | Xaa | Xaa | Xaa |
|     |     |     | 35  |     |     |     |     | 40  |     |     |     |     | 45  |     |

| Xaa | Xaa | Xaa | Xaa | Xaa | Xaa | Xaa | Xaa | Xaa | Xaa | Xaa | Xaa | Xaa | Xaa | Xaa |
|     |     |     | 50  |     |     |     |     | 55  |     |     |     |     | 60  |     |

| Xaa | Xaa | Xaa | Xaa | Xaa | Xaa | Xaa | Xaa | Xaa | Xaa | Xaa | Xaa | Xaa | Xaa | Xaa |
| 65  |     |     |     |     |     | 70  |     |     |     |     | 75  |     |     | 80  |

| Xaa | Xaa | Xaa | Xaa | Xaa | Xaa | Xaa | Xaa | Xaa | Xaa | Xaa | Xaa | Asp | Ala | Gly | Leu |
|     |     |     |     | 85  |     |     |     |     | 90  |     |     |     |     | 95  |     |

Tyr Arg Cys Met Val
            100

(2) INFORMATION FOR SEQ ID NO:9:

(i) SEQUENCE CHARACTERISTICS:
        (A) LENGTH: 99 amino acids
        (B) TYPE: amino acid
        (D) TOPOLOGY: linear (ii) MOLECULE TYPE: peptide (xi) SEQUENCE DESCRIPTION: SEQ ID NO:9:

| Gly | Asp | Leu | Ile | Lys | Leu | Phe | Cys | Xaa | Xaa | Xaa | Xaa | Xaa | Xaa | Xaa |
|     |     |     |     | 5   |     |     |     |     | 10  |     |     |     |     | 15  |

| Xaa | Xaa | Xaa | Xaa | Xaa | Xaa | Xaa | Xaa | Xaa | Xaa | Xaa | Xaa | Xaa | Xaa | Xaa |
|     |     |     | 20  |     |     |     |     | 25  |     |     |     |     | 30  |     |

| Xaa | Xaa | Xaa | Xaa | Xaa | Xaa | Xaa | Xaa | Xaa | Xaa | Xaa | Xaa | Xaa | Xaa | Xaa |
|     |     |     | 35  |     |     |     |     | 40  |     |     |     |     | 45  |     |

| Xaa | Xaa | Xaa | Xaa | Xaa | Xaa | Xaa | Xaa | Xaa | Xaa | Xaa | Xaa | Xaa | Xaa | Xaa |
|     |     |     | 50  |     |     |     |     | 55  |     |     |     |     | 60  |     |

| Xaa | Xaa | Xaa | Xaa | Xaa | Xaa | Xaa | Xaa | Xaa | Xaa | Xaa | Xaa | Xaa | Xaa | Xaa |
| 65  |     |     |     |     |     | 70  |     |     |     |     | 75  |     |     | 80  |

| Xaa | Xaa | Xaa | Xaa | Xaa | Xaa | Xaa | Xaa | Xaa | Xaa | Asp | Phe | Gly | Asn | Tyr | Tyr |
|     |     |     |     | 85  |     |     |     |     | 90  |     |     |     |     | 95  |     |

Cys Ser Val
          99

(2) INFORMATION FOR SEQ ID NO:10:

(i) SEQUENCE CHARACTERISTICS:
        (A) LENGTH: 2909 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:10:

```
GGCCGAGCAT GGGGCGCCCG GCGCCGAGGC CGCTGCTGCT GGCGCTCCTA TCGCTGGCTG      60
TCTGCCGCGG GCGTGTGGTG AGAGTCCCTG CGGGCACCCT GGTTCGAGTG GTGGGCACTG     120
AGCTGGTGAT CCCCTGCAAT GTCAGTGACT ATGATGGCCC CAGTGAGCAA AACTTTGACT     180
GGAGCTTCTC GTCTTCGGGA AGCAGCTTTG TGGAGCTCGC CAGCACCTGG GAGGTGGGCT     240
TCCCGGCGCA GCAGTACCGT GAGCGGCTGC AGCGGGGCGA CATCCTGTTG AGGAGGACAG     300
CCAATGATGC TGTGGAGCTG CACATAAAGA ATGTCCAGCC CTCGGACCAA GGCCACTACA     360
AGTGTTCAAC TCCAAGCACA GACGCCACCG TCCAGGGCAA CTATGAGGAC ACAATGCAGG     420
TTAAAGTGCT GGCAGATGCC CTGGTGGTGG GCCCCAGCTC CCGGCCTCCT CCAGGCCTGA     480
```

-continued

```
GCCTGCGCGA GGGGGAGCCC TTTGAACTTC GATGTATCGC ATCTACTACG TCACCGTTGC    540
ACACACACCT GGCACTTCGG TGGGAACTGC ACCGTGGCCC AGTGCACCGA AGCATCCTAG    600
CCCTAAGCCA CGAGGGCAGG TTTCACCCAG GACCTGGCTA TGAACAGCGC TACCACAGTG    660
GGGATGTACG CCTGGACACG GTGGGCAGCG ATGCCTACCG CCTCTCCGTA GCCCGGGCAC    720
TCTCTGCAGA CCAGGGTTCC TACAGATGTG TGGTCAGTGA GTGGATCACA GAGCAAGGCA    780
GCTGGCAAGA AATCCAAGAA AAAGCTGTGG AAGTGGCCAC TGTGGTGATC CAGCCAACAG    840
CTCTGCAACT GGCCGTGCCC AGGACAGTGT CTGTGACCGA AGGAAAGGAC CTGGACCTTT    900
CTTGCAACAT CACAACAGAC CGTGTGGATG ATGTCCGGCC TGAGGTGACA TGGTACTTCA    960
AAAAGACACC CGATACCTCT TTGCTTGCCT CCCATATGCT GGCTCGGCTG GACCGTGATT   1020
CCCTGGTACA CAGCTCACCA CACGTTGCTC TCAGCCACGT GGATACCCGC TCTTACCATC   1080
TACTGGTGCG AGATGTTAGC AAAGAAAACT CCGGTTACTA TCTATGCCTC GTGGCCCTCT   1140
GGGCTCCTGG ACACAACCGG AGCTGGCACA AGGTGGCAGA GGCCATGTCT GCCCCATCTG   1200
GTGTAAGCGT GACCTGGCTA GAACCAGAAT ACCAGGTCTA CCTGAATGCT TCTAAGGTCC   1260
CCGGGTTTTC CGACGACCCC ACAGAACTGC AATGCCGGGT GATAGACACG AAGCGTGTGG   1320
ATGCCGGTGT CCGACTTACT GTGTCGTGGT ACTATAGAAT GAACCGTCGC AATGATGACG   1380
TGGTGGCCAG CGAGCTTCTC GCCGTCATGG ACGGGACTG GACTCTGAGA TACGGGAGA    1440
GAAGCAAACA GCGGGCCCAG GACGGCGAGT TTATCTTTTC TAAGGAGCAC ACAGACACAT   1500
TCAGTTTCCG GATCCAAAGG ACTACGGAGG AAGACAGGGG CAGTTATTAC TGTGTTGTGT   1560
CTGCCTGGAC CAGGCAGAGG AACAGCAGCT GGGTGAAGAG CAAAGATGTC TTCTCCAAGC   1620
CCGTCAACAT ATTCTGGGCC TCGGAAGATT CTGTGCTCGT GGTGAAGGCA CGGCAGCCAA   1680
AGCCTTTCTT TGCTGCAGGG AATACATTTG AGATGACTTG CAAAGTGTCT TCCAAGAATA   1740
TTAAGTCTCC ACGATACTCT GTTCTCATCA CGGCTGAGAA GCCTGTTGGG GACCTCTCCA   1800
GTCCCAATGA AACCAAGTAC ATCATCTCCC TGGACCAGGA TTCCGTGGTG AAGCTGGAGA   1860
ACTGGACCGA CGCATCTCGG GTGGACGGCG TCGTGTTAGA GAAGGTTCAA GAGGATGAGT   1920
TCCGATACCG AATGTACCAG ACTCAGGTCT CCGATGCGGG CCTGTACCGC TGCATGGTGA   1980
CAGCCTGGTC TCCTATCGGG GGCAGCTTGT GGCGAGAGGC AGCGACCAGT CTTTCCAATC   2040
CTATTGAGAT TGACTTCCAA ACCTCAGGTC CCATATTTAA CGCCTCTGTG CATTCAGACA   2100
CTCTGTCCGT CACCCGGGGA GATCTCATCA AGTTGTTCTG TATCGTCACT GTGGACGGAG   2160
CAGTGCTGGA CCCAGATGAC ATGGCCTTCG ATGTATCCTG GTTGCAGTA CACTCTTTTG   2220
GCTTGGACAA GGCTCCCATC CTCCTATCCT CCTTGGACCG GAAGGGAGTC GTGACTACAG   2280
GCCAGAGGGA CTGGAAGAGT ACCGTCAGCC TGGAGCGAGT GAGCGTGCTG GAATTTTTGC   2340
TGCAAGTGCA TAGCTCTGAG GACCAGGACT TTGGCAACTA CTATTGTTCT GTGACTCCCT   2400
GGGTGAGGTC ACCAACTGGT TCCTGGCAGA GGGAAGCCGA GATCCACTCC AGGCCCATCT   2460
TTATAACTGT GAAGATGGAT GTGCTGAACG CCTTCAAGTA CCCGCTGCTG ATCGGCGTGG   2520
GCCTGTCCAC AGTCATCGGG CTCCTGTCCT GCCTCATTGG GTACTGCAGT TCCCATTGGT   2580
GCTGTAAGAA GGAGGTGCGG GAGACGCGTC GGGAGCGCCG CAGGCTCATG TCCATGGAGA   2640
TGGATTAAGC AGTTGGAGGG ACAGAGGAAC GTTGTAGGAG CAGTGGGGTG GGGGGTGAGA   2700
AGAGGACTCT GAGATTTTAC AACCGAGTGT GTTACACTAA AACCGGTCCT CTCTAATCTC   2760
AGGTGGGACT CAGCGCTCTC TCTTTTCTGC ATGTCAAGTT CCGAGCGCGG ACATGTTTAC   2820
CAGCACACGG CTCTTCTTCC CACGGCACTT TCTGATATGT AACAATCGAG TGTGTGTCTC   2880
```

CCCCCCCCCG CTGAAGCTGT TAATGGTT 2909

( 2 ) INFORMATION FOR SEQ ID NO:11:

( i ) SEQUENCE CHARACTERISTICS:
    ( A ) LENGTH: 2909 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:11:

| | | | | | | |
|---|---|---|---|---|---|---|
| GGCCGAGCAT | GGGGCGCCCG | GCGCCGAGGC | CGCTGCTGCT | GGCGCTCCTA | TCGCTGGCTG | 60 |
| TCTGCCGCGG | GCGTGTGGTG | AGAGTCCCTG | CGGGCACCCT | GGTTCGAGTG | GTGGGCACTG | 120 |
| AGCTGGTGAT | CCCCTGCAAT | GTCAGTGACT | ATGATGGCCC | CAGTGAGCAA | AACTTTGACT | 180 |
| GGAGCTTCTC | GTCTTCGGGA | AGCAGCTTTG | TGGAGCTCGC | CAGCACCTGG | GAGGTGGGCT | 240 |
| TCCCGGCGCA | GCAGTACCGT | GAGCGGCTGC | AGCGGGCGA | CATCCTGTTG | AGGAGGACAG | 300 |
| CCAATGATGC | TGTGGAGCTG | CACATAAAGA | ATGTCCAGCC | CTCGGACCAA | GGCCACTACA | 360 |
| AGTGTTCAAC | TCCAAGCACA | GACGCCACCG | TCCAGGGCAA | CTATGAGGAC | ACAATGCAGG | 420 |
| TTAAAGTGCT | GGCAGATGCC | CTGGTGGTGG | GCCCCAGCTC | CCGGCCTCCT | CCAGGCCTGA | 480 |
| GCCTGCGCGA | GGGGGAGCCC | TTTGAACTTC | GATGTATCGC | ATCTACTACG | TCACCGTTGC | 540 |
| ACACACACCT | GGCACTTCGG | TGGGAACTGC | ACCGTGGCCC | AGTGCACCGA | AGCATCCTAG | 600 |
| CCCTAAGCCA | CGAGGGCAGG | TTTCACCCAG | GACCTGGCTA | TGAACAGCGC | TACCACAGTG | 660 |
| GGGATGTACG | CCTGGACACG | GTGGGCAGCG | ATGCCTACCG | CCTCTCCGTA | GCCCGGGCAC | 720 |
| TCTCTGCAGA | CCAGGGTTCC | TACAGATGTG | TGGTCAGTGA | GTGGATCACA | GAGCAAGGCA | 780 |
| GCTGGCAAGA | AATCCAAGAA | AAAGCTGTGG | AAGTGGCCAC | TGTGGTGATC | CAGCCAACAG | 840 |
| CTCTGCAACT | GGCCGTGCCC | AGGACAGTGT | CTGTGACCGA | AGGAAAGGAC | CTGGACCTTT | 900 |
| CTTGCAACAT | CACAACAGAC | CGTGTGGATG | ATGTCCGGCC | TGAGGTGACA | TGGTACTTCA | 960 |
| AAAAGACACC | CGATACCTCT | TTGCTTGCCT | CCCATATGCT | GGCTCGGCTG | GACCGTGATT | 1020 |
| CCCTGGTACA | CAGCTCACCA | CACGTTGCTC | TCAGCCACGT | GGATACCCGC | TCTTACCATC | 1080 |
| TACTGGTGCG | AGATGTTAGC | AAAGAAAACT | CCGGTTACTA | TCTATGCCTC | GTGGCCCTCT | 1140 |
| GGGCTCCTGG | ACACAACCGG | AGCTGGCACA | AGGTGGCAGA | GGCCATGTCT | GCCCCATCTG | 1200 |
| GTGTAAGCGT | GACCTGGCTA | GAACCAGAAT | ACCAGGTCTA | CCTGAATGCT | TCTAAGGTCC | 1260 |
| CCGGGTTTTC | CGACGACCCC | ACAGAACTGC | AATGCCGGGT | GATAGACACG | AAGCGTGTGG | 1320 |
| ATGCCGGTGT | CCGACTTACT | GTGTCGTGGT | ACTATAGAAT | GAACCGTCGC | AATGATGACG | 1380 |
| TGGTGGCCAG | CGAGCTTCTC | GCCGTCATGG | ACGGGACTG | GACTCTGAGA | TACGGGAGA | 1440 |
| GAAGCAAACA | GCGGGCCCAG | GACGGCGAGT | TTATCTTTTC | TAAGGAGCAC | ACAGACACAT | 1500 |
| TCAGTTTCCG | GATCCAAAGG | ACTACGGAGG | AAGACAGGGG | CAGTTATTAC | TGTGTTGTGT | 1560 |
| CTGCCTGGAC | CAGGCAGAGG | AACAGCAGCT | GGGTGAAGAG | CAAAGATGTC | TTCTCCAAGC | 1620 |
| CCGTCAACAT | ATTCTGGGCC | TCGGAAGATT | CTGTGCTCGT | GGTGAAGGCA | CGGCAGCCAA | 1680 |
| AGCCTTTCTT | TGCTGCAGGG | AATACATTTG | AGATGACTTG | CAAAGTGTCT | TCCAAGAATA | 1740 |
| TTAAGTCTCC | ACGATACTCT | GTTCTCATCA | CGGCTGAGAA | GCCTGTTGGG | GACCTCTCCA | 1800 |
| GTCCCAATGA | AACCAAGTAC | ATCATCTCCC | TGGACCAGGA | TTCCGTGGTG | AAGCTGGAGA | 1860 |
| ACTGGACCGA | CGCATCTCGG | GTGGACGGCG | TCGTGTTAGA | GAAGGTTCAA | GAGGATGAGT | 1920 |

| | | | | | |
|---|---|---|---|---|---|
| TCCGATACCG | AATGTACCAG | ACTCAGGTCT | CCGATGCGGG | CCTGTACCGC | TGCATGGTGA | 1980
| CAGCCTGGTC | TCCTATCGGG | GGCAGCTTGT | GGCGAGAGGC | AGCGACCAGT | CTTTCCAATC | 2040
| CTATTGAGAT | TGACTTCCAA | ACCTCAGGTC | CCATATTTAA | CGCCTCTGTG | CATTCAGACA | 2100
| CTCTGTCCGT | CACCCGGGGA | GATCTCATCA | AGTTGTTCTG | TATCGTCACT | GTGGACGGAG | 2160
| CAGTGCTGGA | CCCAGATGAC | ATGGCCTTCG | ATGTATCCTG | GTTTGCAGTA | CACTCTTTTG | 2220
| GCTTGGACAA | GGCTCCCATC | CTCCTATCCT | CCTTGGACCG | GAAGGGAGTC | GTGACTACAG | 2280
| GCCAGAGGGA | CTGGAAGAGT | ACCGTCAGCC | TGGAGCGAGT | GAGCGTGCTG | GAATTTTTGC | 2340
| TGCAAGTGCA | TAGCTCTGAG | GACCAGGACT | TTGGCAACTA | CTATTGTTCT | GTGACTCCCT | 2400
| GGGTGAGGTC | ACCAACTGGT | TCCTGGCAGA | GGGAAGCCGA | GATCCACTCC | AGGCCCATCT | 2460
| TTATAACTGT | GAAGATGGAT | GTGCTGAACG | CCTTCAAGTA | CCCGCTGCTG | ATCGGCGTGG | 2520
| GCCTGTCCAC | AGTCATCCGG | CTCCTGTCCT | GCCTCATTGG | GTACTGCAGT | TCCCATTGGT | 2580
| GCTGTAAGAA | GGAGGTGCGG | GAGACGCGTC | GGGAGCGCCG | CAGGCTCATG | TCCATGGAGA | 2640
| TGGATTAAGC | AGTTGGAGGG | ACAGAGGAAC | GTTGTAGGAG | CAGTGGGGTG | GGGGGTGAGA | 2700
| AGAGGACTCT | GAGATTTTAC | AACCGAGTGT | GTTACACTAA | AACCGGTCCT | CTCTAATCTC | 2760
| AGGTGGGACT | CAGCGCTCTC | TCTTTTCTGC | ATGTCAAGTT | CCGAGCGCGG | ACATGTTTAC | 2820
| CAGCACACGG | CTCTTCTTCC | CACGGCACTT | TCTGATATGT | AACAATCGAG | TGTGTGTCTC | 2880
| CCCCCCCCCG | CTGAAGCTGT | TTAATGGTT | | | | 2909

( 2 ) INFORMATION FOR SEQ ID NO:12:

( i ) SEQUENCE CHARACTERISTICS:
        ( A ) LENGTH: 2636 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:12:

| | | | | | |
|---|---|---|---|---|---|
| GGCCGAGCAT | GGGGCGCCCG | GCGCCGAGGC | CGCTGCTGCT | GGCGCTCCTA | TCGCTGGCTG | 60
| TCTGCCGCGG | GCGTGTGGTG | AGAGTCCCTG | CGGGCACCCT | GGTTCGAGTG | GTGGGCACTG | 120
| AGCTGGTGAT | CCCCTGCAAT | GTCAGTGACT | ATGATGGCCC | CAGTGAGCAA | AACTTTGACT | 180
| GGAGCTTCTC | GTCTTCGGGA | AGCAGCTTTG | TGGAGCTCGC | CAGCACCTGG | GAGGTGGGCT | 240
| TCCCGGCGCA | GCAGTACCGT | GAGCGGCTGC | AGCGGGGCGA | CATCCTGTTG | AGGAGGACAG | 300
| CCAATGATGC | TGTGGAGCTG | CACATAAAGA | ATGTCCAGCC | CTCGGACCAA | GGCCACTACA | 360
| AGTGTTCAAC | TCCAAGCACA | GACGCCACCG | TCCAGGGCAA | CTATGAGGAC | ACAATGCAGG | 420
| TTAAAGTGCT | GGCAGATGCC | CTGGTGGTGG | GCCCCAGCTC | CCGGCCTCCT | CCAGGCCTGA | 480
| GCCTGCGCGA | GGGGGAGCCC | TTTGAACTTC | GATGTATCGC | ATCTACTACG | TCACCGTTGC | 540
| ACACACACCT | GGCACTTCGG | TGGGAACTGC | ACCGTGGCCC | AGTGCACCGA | AGCATCCTAG | 600
| CCCTAAGCCA | CGAGGGCAGG | TTTCACCCAG | GACCTGGCTA | TGAACAGCGC | TACCACAGTG | 660
| GGGATGTACG | CCTGGACACG | GTGGGCAGCG | ATGCCTACCG | CCTCTCCGTA | GCCCGGGCAC | 720
| TCTCTGCAGA | CCAGGGTTCC | TACAGATGTG | TGGTCAGTGA | GTGGATCACA | GAGCAAGGCA | 780
| GCTGGCAAGA | AATCCAAGAA | AAAGCTGTGG | AAGTGGCCAC | TGTGGTGATC | CAGCCAACAG | 840
| CTCTGCAACT | GGCCGTGCCC | AGGACAGTGT | CTGTGACCGA | AGGAAAGGAC | CTGGACCTTT | 900
| CTTGCAACAT | CACAACAGAC | CGTGTGGATG | ATGTCCGGCC | TGAGGTGACA | TGGTACTTCA | 960
| AAAAGACACC | CGATACCTCT | TTGCTTGCCT | CCCATATGCT | GGCTCGGCTG | GACCGTGATT | 1020

| | | | | | |
|---|---|---|---|---|---|
| CCCTGGTACA | CAGCTCACCA | CACGTTGCTC | TCAGCCACGT | GGATACCCGC | TCTTACCATC | 1080 |
| TACTGGTGCG | AGATGTTAGC | AAAGAAAACT | CCGGTTACTA | TCTATGCCTC | GTGGCCCTCT | 1140 |
| GGGCTCCTGG | ACACAACCGG | AGCTGGCACA | AGGTGGCAGA | GGCCATGTCT | GCCCCATCTG | 1200 |
| GTGTAAGCGT | GACCTGGCTA | GAACCAGAAT | ACCAGGTCTA | CCTGAATGCT | TCTAAGGTCC | 1260 |
| CCGGGTTTTC | CGACGACCCC | ACAGAACTGC | AATGCCGGGT | GATAGACACG | AAGCGTGTGG | 1320 |
| ATGCCGGTGT | CCGACTTACT | GTGTCGTGGT | ACTATAGAAT | GAACCGTCGC | AATGATGACG | 1380 |
| TGGTGGCCAG | CGAGCTTCTC | GCCGTCATGG | ACGGGACTG | GACTCTGAGA | TACGGGAGA | 1440 |
| GAAGCAAACA | GCGGGCCCAG | GACGGCGAGT | TTATCTTTTC | TAAGGAGCAC | ACAGACACAT | 1500 |
| TCAGTTTCCG | GATCCAAAGG | ACTACGGAGG | AAGACAGGGG | CAGTTATTAC | TGTGTTGTGT | 1560 |
| CTGCCTGGAC | CAGGCAGAGG | AACAGCAGCT | GGGTGAAGAG | CAAAGATGTC | TTCTCCAAGC | 1620 |
| CCGTCAACAT | ATTCTGGGCC | TCGGAAGATT | CTGTGCTCGT | GGTGAAGGCA | CGGCAGCCAA | 1680 |
| AGCCTTTCTT | TGCTGCAGGG | AATACATTTG | AGATGACTTG | CAAAGTGTCT | TCCAAGAATA | 1740 |
| TTAAGTCTCC | ACGATACTCT | GTTCTCATCA | CGGCTGAGAA | GCCTGTTGGG | GACCTCTCCA | 1800 |
| GTCCCAATGA | AACCAAGTAC | ATCATCTCCC | TGGACCAGGA | TTCCGTGGTG | AAGCTGGAGA | 1860 |
| ACTGGACCGA | CGCATCTCGG | GTGGACGGCG | TCGTGTTAGA | GAAGGTTCAA | GAGGATGAGT | 1920 |
| TCCGATACCG | AATGTACCAG | ACTCAGGTCT | CCGATGCGGG | CCTGTACCGC | TGCATGGTGA | 1980 |
| CAGCCTGGTC | TCCTATCGGG | GGCAGCTTGT | GGCGAGAGGC | AGCGACCAGT | CTTTCCAATC | 2040 |
| CTATTGAGAT | TGACTTCCAA | ACCTCAGGTC | CCATATTTAA | CGCCTCTGTG | CATTCAGACA | 2100 |
| CTCTGTCCGT | CACCCGGGGA | GATCTCATCA | AGTTGTTCTG | TATCGTCACT | GTGGACGGAG | 2160 |
| CAGTGCTGGA | CCCAGATGAC | ATGGCCTTCG | ATGTATCCTG | GTTTGCAGTA | CACTCTTTTG | 2220 |
| GCTTGGACAA | GGCTCCCATC | CTCCTATCCT | CCTTGGACCG | GAAGGGAGTC | GTGACTACAG | 2280 |
| GCCAGAGGGA | CTGGAAGAGT | ACCGTCAGCC | TGGAGCGAGT | GAGCGTGCTG | GAATTTTTGC | 2340 |
| TGCAAGTGCA | TAGCTCTGAG | GACCAGATGG | ATTAAGCAGT | TGGAGGGACA | GAGGAACGTT | 2400 |
| GTAGGAGCAG | TGGGGTGGGG | GGTGAGAAGA | GGACTCTGAG | ATTTACAAC | CGAGTGTGTT | 2460 |
| ACACTAAAAC | CGGTCCTCTC | TAATCTCAGG | TGGGACTCAG | CGCTCTCTCT | TTTCTGCATG | 2520 |
| TCAAGTTCCG | AGCGCGGACA | TGTTACCAG | CACACGGCTC | TTCTTCCCAC | GGCACTTTCT | 2580 |
| GATATGTAAC | AATCGAGTGT | GTGTCTCCCC | CCCCCCGCTG | AAGCTGTTTA | ATGGTT | 2636 |

( 2 ) INFORMATION FOR SEQ ID NO:13:

( i ) SEQUENCE CHARACTERISTICS:
        ( A ) LENGTH: 1784 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:13:

| | | | | | |
|---|---|---|---|---|---|
| GGCCGAGCAT | GGGGCGCCCG | GCGCCGAGGC | CGCTGCTGCT | GGCGCTCCTA | TCGCTGGCTG | 60 |
| TCTGCCGCGG | GCGTGTGGTG | AGAGTCCCTG | CGGGCACCCT | GGTTCGAGTG | GTGGGCACTG | 120 |
| AGCTGGTGAT | CCCCTGCAAT | GTCAGTGACT | ATGATGGCCC | CAGTGAGCAA | AACTTTGACT | 180 |
| GGAGCTTCTC | GTCTTCGGGA | AGCAGCTTTG | TGGAGCTCGC | CAGCACCTGG | GAGGTGGGCT | 240 |
| TCCCGGCGCA | GCAGTACCGT | GAGCGGCTGC | AGCGGGGCGA | CATCCTGTTG | AGGAGGACAG | 300 |
| CCAATGATGC | TGTGGAGCTG | CACATAAAGA | ATGTCCAGCC | CTCGGACCAA | GGCCACTACA | 360 |

```
AGTGTTCAAC  TCCAAGCACA  GACGCCACCG  TCCAGGGCAA  CTATGAGGAC  ACAATGCAGG   420
TTAAAGTGCT  GGCAGATGCC  CTGGTGGTGG  GCCCCAGCTC  CCGGCCTCCT  CCAGGCCTGA   480
GCCTGCGCGA  GGGGGAGCCC  TTTGAACTTC  GATGTATCGC  ATCTACTACG  TCACCGTTGC   540
ACACACACCT  GGCACTTCGG  TGGGAACTGC  ACCGTGGCCC  AGTGCACCGA  AGCATCCTAG   600
CCCTAAGCCA  CGAGGGCAGG  TTTCACCCAG  GACCTGGCTA  TGAACAGCGC  TACCACAGTG   660
GGGATGTACG  CCTGGACACG  GTGGGCAGCG  ATGCCTACCG  CCTCTCCGTA  GCCCGGGCAC   720
TCTCTGCAGA  CCAGGGTTCC  TACAGATGTG  TGGTCAGTGA  GTGGATCACA  GAGCAAGGCA   780
GCTGGCAAGA  AATCCAAGAA  AAAGCTGTGG  AAGTGGCCAC  TGTGGTGATC  CAGCCAACAG   840
CTCTGCAACT  GGCCGTGCCC  AGGACAGTGT  CTGTGACCGA  AGGAAAGGAC  CTGGACCTTT   900
CTTGCAACAT  CACAACAGAC  CGTGTGGATG  ATGTCCGGCC  TGAGGTGACA  TGGTACTTCA   960
AAAAGACACC  CGATACCTCT  TTGCTTGCCT  CCCATATGCT  GGCTCGGCTG  GACCGTGATT  1020
CCCTGGTACA  CAGCTCACCA  CACGTTGCTC  TCAGCCACGT  GGATACCCGC  TCTTACCATC  1080
TACTGGTGCG  AGATGTTAGC  AAAGAAAACT  CCGGTTACTA  TCTATGCCTC  GTGGCCCTCT  1140
GGGCTCCTGG  ACACAACCGG  AGCTGGCACA  AGGTGGCAGA  GGCCATGTCT  GCCCATCTG   1200
GTGTAAGCGT  GACCTGGCTA  GAACCAGAAT  ACCAGGTCTA  CCTGAATGCT  TCTAAGGTCC  1260
CCGGGTTTTC  CGACGACCCC  ACAGAACTGC  AATGCCGGGT  GATAGACACG  AAGCGTGTGG  1320
ATGCCGGTGT  CCGACTTACT  GTGTCGTGGT  ACTATAGAAT  GAACCGTCGC  AATGATGACG  1380
TGGTGGCCAG  CGAGCTTCTC  GCCGTCATGG  ACGGGACTG   GACTCTGAGA  TACGGGGAGA  1440
GAAGCAAACA  GCGGGCCCAG  GACGGCGAGT  TTATCTTTTC  TAAGGAGCAC  ACAGACACAT  1500
TCAGTTTCCG  GATCATGGAT  TAAGCAGTTG  GAGGGACAGA  GGAACGTTGT  AGGAGCAGTG  1560
GGGTGGGGGG  TGAGAAGAGG  ACTCTGAGAT  TTTACAACCG  AGTGTGTTAC  ACTAAAACCG  1620
GTCCTCTCTA  ATCTCAGGTG  GGACTCAGCG  CTCTCTCTTT  TCTGCATGTC  AAGTTCCGAG  1680
CGCGGACATG  TTTACCAGCA  CACGGCTCTT  CTTCCCACGG  CACTTTCTGA  TATGTAACAA  1740
TCGAGTGTGT  GTCTCCCCCC  CCCCGCTGAA  GCTGTTTAAT  GGTT                    1784
```

( 2 ) INFORMATION FOR SEQ ID NO:14:

( i ) SEQUENCE CHARACTERISTICS:
        ( A ) LENGTH: 1213 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:14:

```
GGCCGAGCAT  GGGGCGCCCG  GCGCCGAGGC  CGCTGCTGCT  GGCGCTCCTA  TCGCTGGCTG    60
TCTGCCGCGG  GCGTGTGGTG  AGAGTCCCTG  CGGGCACCCT  GGTTCGAGTG  GTGGGCACTG   120
AGCTGGTGAT  CCCCTGCAAT  GTCAGTGACT  ATGATGGCCC  CAGTGAGCAA  AACTTTGACT   180
GGAGCTTCTC  GTCTTCGGGA  AGCAGCTTTG  TGGAGCTCGC  CAGCACCTGG  GAGGTGGGCT   240
TCCCGGCGCA  GCAGTACCGT  GAGCGGCTGC  AGCGGGGCGA  CATCCTGTTG  AGGAGGACAG   300
CCAATGATGC  TGTGGAGCTG  CACATAAAGA  ATGTCCAGCC  CTCGGACCAA  GGCCACTACA   360
AGTGTTCAAC  TCCAAGCACA  GACGCCACCG  TCCAGGGCAA  CTATGAGGAC  ACAATGCAGG   420
TTAAAGTGCT  GGCAGATGCC  CTGGTGGTGG  GCCCCAGCTC  CCGGCCTCCT  CCAGGCCTGA   480
GCCTGCGCGA  GGGGGAGCCC  TTTGAACTTC  GATGTATCGC  ATCTACTACG  TCACCGTTGC   540
ACACACACCT  GGCACTTCGG  TGGGAACTGC  ACCGTGGCCC  AGTGCACCGA  AGCATCCTAG   600
```

-continued

| | | | | | |
|---|---|---|---|---|---|
| CCCTAAGCCA | CGAGGGCAGG | TTTCACCCAG | GACCTGGCTA | TGAACAGCGC | TACCACAGTG | 660 |
| GGGATGTACG | CCTGGACACG | GTGGGCAGCG | ATGCCTACCG | CCTCTCCGTA | GCCCGGGCAC | 720 |
| TCTCTGCAGA | CCAGGGTTCC | TACAGATGTG | TGGTCAGTGA | GTGGATCACA | GAGCAAGGCA | 780 |
| GCTGGCAAGA | AATCCAAGAA | AAAGCTGTGG | AAGTGGCCAC | TGTGGTGATC | CAGCCAACAG | 840 |
| CTCTGCAACT | GGCCGTGCCC | AGGACAGTGT | CTGTGACCGA | AGGAAAGGAC | CTGGACCTTT | 900 |
| CTTGCAACAT | CACAACAGAC | CGTGTGGATG | ATGTCCGGCC | TGAATGGATT | AAGCAGTTGG | 960 |
| AGGGACAGAG | GAACGTTGTA | GGAGCAGTGG | GGTGGGGGGT | GAGAAGAGGA | CTCTGAGATT | 1020 |
| TTACAACCGA | GTGTGTTACA | CTAAAACCGG | TCCTCTCTAA | TCTCAGGTGG | GACTCAGCGC | 1080 |
| TCTCTCTTTT | CTGCATGTCA | AGTTCCGAGC | GCGGACATGT | TTACCAGCAC | ACGGCTCTTC | 1140 |
| TTCCCACGGC | ACTTTCTGAT | ATGTAACAAT | CGAGTGTGTG | TCTCCCCCCC | CCCGCTGAAG | 1200 |
| CTGTTTAATG | GTT | | | | | 1213 |

(2) INFORMATION FOR SEQ ID NO:15:

(i) SEQUENCE CHARACTERISTICS:
        (A) LENGTH: 483 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:15:

| | | | | | |
|---|---|---|---|---|---|
| GGCCGAGCAT | GGGGCGCCCG | GCGCCGAGGC | CGCTGCTGCT | GGCGCTCCTA | TCGCTGGCTG | 60 |
| TCTGCCGCGG | GCGTGTGGTG | AGAGTCCCTG | CGGGCACCCT | GGTTCGAGTG | GTGGGCACTG | 120 |
| AGCTGGTGAT | CCCCTGCAAT | GTCAGTGACT | ATGATGGCCC | CAGTGAGCAA | AACTTTGACT | 180 |
| GGAGCTTCTC | GTCTTCGGGA | AGCAGCTTTG | TGGATGGATT | AAGCAGTTGG | AGGGACAGAG | 240 |
| GAACGTTGTA | GGAGCAGTGG | GGTGGGGGGT | GAGAAGAGGA | CTCTGAGATT | TTACAACCGA | 300 |
| GTGTGTTACA | CTAAAACCGG | TCCTCTCTAA | TCTCAGGTGG | GACTCAGCGC | TCTCTCTTTT | 360 |
| CTGCATGTCA | AGTTCCGAGC | GCGGACATGT | TTACCAGCAC | ACGGCTCTTC | TTCCACGGC | 420 |
| ACTTTCTGAT | ATGTAACAAT | CGAGTGTGTG | TCTCCCCCCC | CCCGCTGAAG | CTGTTTAATG | 480 |
| GTT | | | | | | 483 |

(2) INFORMATION FOR SEQ ID NO:16:

(i) SEQUENCE CHARACTERISTICS:
        (A) LENGTH: 1508 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:16:

| | | | | | |
|---|---|---|---|---|---|
| GGCCGAGCAT | GGGGCGCCCG | GCGCCGAGGC | CGCTGCTGCT | GGCGCTCCTA | TCGCTGGCTG | 60 |
| TCTGCCGCGG | GCGTGTGGTG | AGAGTCCCTG | CGGGCACCCT | GGTTCGAGTG | GTGGGCACTG | 120 |
| AGCTGGTGAT | CCCCTGCAAT | GTCAGTGACT | ATGATGGCCC | CAGTGAGCAA | AACTTTGACT | 180 |
| GGAGCTTCTC | GTCTTCGGGA | AGCAGCTTTG | TGGAGCTCGC | CAGCACCTGG | GAGGTGGGCT | 240 |
| TCCCGGCGCA | GCAGTACCGT | GAGCGGCTGC | AGCGGGCGA | CATCCTGTTG | AGGAGGACAG | 300 |
| CCAATGATGC | TGTGGAGCTG | CACATAAAGA | ATGTCCAGCC | CTCGGACCAA | GGCCACTACA | 360 |
| AGTGTTCAAC | TCCAAGCACA | GACGCCACCG | TCCAGGGCAA | CTATGAGGAC | ACAATGCAGG | 420 |

| | | | | | |
|---|---|---|---|---|---|
|TTAAAGTGCT|GGCAGATGCC|CTGGTGGTGG|GCCCCAGCTC|CCGGCCTCCT|CCAGGCCTGA|480|
|GCCTGCGCGA|GGGGGAGCCC|TTTGAACTTC|GATGTATCGC|ATCTACTACG|TCACCGTTGC|540|
|ACACACACCT|GGCACTTCGG|TGGGAACTGC|ACCGTGGCCC|AGTGCACCGA|AGCATCCTAG|600|
|CCCTAAGCCA|CGAGGGCAGG|TTTCACCCAG|GACCTGGCTA|TGAACAGCGC|TACCACAGTG|660|
|GGGATGTACG|CCTGGACACG|GTGGGCAGCG|ATGCCTACCG|CCTCTCCGTA|GCCGGGGAG|720|
|ATCTCATCAA|GTTGTTCTGT|ATCGTCACTG|TGGACGGAGC|AGTGCTGGAC|CCAGATGACA|780|
|TGGCCTTCGA|TGTATCCTGG|TTTGCAGTAC|ACTCTTTTGG|CTTGGACAAG|GCTCCCATCC|840|
|TCCTATCCTC|CTTGGACCGG|AAGGGAGTCG|TGACTACAGG|CCAGAGGGAC|TGGAAGAGTA|900|
|CCGTCAGCCT|GGAGCGAGTG|AGCGTGCTGG|AATTTTGCT|GCAAGTGCAT|AGCTCTGAGG|960|
|ACCAGGACTT|TGGCAACTAC|TATTGTTCTG|TGACTCCCTG|GGTGAGGTCA|CCAACTGGTT|1020|
|CCTGGCAGAG|GGAAGCCGAG|ATCCACTCCA|GGCCCATCTT|TATAACTGTG|AAGATGGATG|1080|
|TGCTGAACGC|CTTCAAGTAC|CCGCTGCTGA|TCGGCGTGGG|CCTGTCCACA|GTCATCGGGC|1140|
|TCCTGTCCTG|CCTCATTGGG|TACTGCAGTT|CCCATTGGTG|CTGTAAGAAG|GAGGTGCGGG|1200|
|AGACGCGTCG|GGAGCGCCGC|AGGCTCATGT|CCATGGAGAT|GGATTAAGCA|GTTGGAGGGA|1260|
|CAGAGGAACG|TTGTAGGAGC|AGTGGGGTGG|GGGTGAGAA|GAGGACTCTG|AGATTTTACA|1320|
|ACCGAGTGTG|TTACACTAAA|ACCGGTCCTC|TCTAATCTCA|GGTGGGACTC|AGCGCTCTCT|1380|
|CTTTTCTGCA|TGTCAAGTTC|CGAGCGCGGA|CATGTTTACC|AGCACACGGC|TCTTCTTCCC|1440|
|ACGGCACTTT|CTGATATGTA|ACAATCGAGT|GTGTGTCTCC|CCCCCCCGC|TGAAGCTGTT|1500|
|TAATGGTT| | | | | |1508|

( 2 ) INFORMATION FOR SEQ ID NO:17:

( i ) SEQUENCE CHARACTERISTICS:
        ( A ) LENGTH: 1007 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:17:

| | | | | | |
|---|---|---|---|---|---|
|GGCCGAGCAT|GGGGCGCCCG|GCGCCGAGGC|CGCTGCTGCT|GGCGCTCCTA|TCGCTGGCTG|60|
|TCTGCCGCGG|GCGTGTGGTG|AGAGTCCCTG|CGGGCACCCT|GGTTCGAGTG|GTGGGCACTG|120|
|AGCTGGTGAT|CCCCTGCAAT|GTCAGTGACT|ATGATGGCCC|CAGTGAGCAA|AACTTTGACT|180|
|GGAGCTTCTC|GTCTTCGGGA|AGCAGCTTTG|TGGGGGGAGA|TCTCATCAAG|TTGTTCTGTA|240|
|TCGTCACTGT|GGACGGAGCA|GTGCTGGACC|CAGATGACAT|GGCCTTCGAT|GTATCCTGGT|300|
|TTGCAGTACA|CTCTTTTGGC|TTGGACAAGG|CTCCCATCCT|CCTATCCTCC|TTGGACCGGA|360|
|AGGGAGTCGT|GACTACAGGC|CAGAGGGACT|GGAAGAGTAC|CGTCAGCCTG|GAGCGAGTGA|420|
|GCGTGCTGGA|ATTTTGCTG|CAAGTGCATA|GCTCTGAGGA|CCAGGACTTT|GGCAACTACT|480|
|ATTGTTCTGT|GACTCCCTGG|GTGAGGTCAC|CAACTGGTTC|CTGGCAGAGG|GAAGCCGAGA|540|
|TCCACTCCAG|GCCCATCTTT|ATAACTGTGA|AGATGGATGT|GCTGAACGCC|TTCAAGTACC|600|
|CGCTGCTGAT|CGGCGTGGGC|CTGTCCACAG|TCATCGGGCT|CCTGTCCTGC|CTCATTGGGT|660|
|ACTGCAGTTC|CCATTGGTGC|TGTAAGAAGG|AGGTGCGGGA|GACGCGTCGG|GAGCGCCGCA|720|
|GGCTCATGTC|CATGGAGATG|GATTAAGCAG|TTGGAGGGAC|AGAGGAACGT|TGTAGGAGCA|780|
|GTGGGGTGGG|GGGTGAGAAG|AGGACTCTGA|GATTTTACAA|CCGAGTGTGT|TACACTAAAA|840|

5,747,660

61 62

-continued

| CCGGTCCTCT | CTAATCTCAG | GTGGGACTCA | GCGCTCTCTC | TTTTCTGCAT | GTCAAGTTCC | 900 |
| GAGCGCGGAC | ATGTTTACCA | GCACACGGCT | CTTCTTCCCA | CGGCACTTTC | TGATATGTAA | 960 |
| CAATCGAGTG | TGTGTCTCCC | CCCCCCCGCT | GAAGCTGTTT | AATGGTT | | 1007 |

( 2 ) INFORMATION FOR SEQ ID NO:18:

( i ) SEQUENCE CHARACTERISTICS:
        ( A ) LENGTH: 1007 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:18:

| GGCCGAGCAT | GGGGCGCCCG | GCGCCGAGGC | CGCTGCTGCT | GGCGCTCCTA | TCGCTGGCTG | 60 |
| TCTGCCGCGG | GCGTGTGGTG | AGAGTCCCTG | CGGGCACCCT | GGTTCGAGTG | GTGGGCACTG | 120 |
| AGCTGGTGAT | CCCCTGCAAT | GTCAGTGACT | ATGATGGCCC | CAGTGAGCAA | AACTTTGACT | 180 |
| GGAGCTTCTC | GTCTTCGGGA | AGCAGCTTTG | TGGGGGAGA | TCTCATCAAG | TTGTTCTGTA | 240 |
| TCGTCACTGT | GGACGGAGCA | GTGCTGGACC | CAGATGACAT | GGCCTTCGAT | GTATCCTGGT | 300 |
| TTGCAGTACA | CTCTTTTGGC | TTGGACAAGG | CTCCCATCCT | CCTATCCTCC | TTGGACCGGA | 360 |
| AGGGAGTCGT | GACTACAGGC | CAGAGGGACT | GGAAGAGTAC | CGTCAGCCTG | GAGCGAGTGA | 420 |
| GCGTGCTGGA | ATTTTGCTG | CAAGTGCATA | GCTCTGAGGA | CCAGGACTTT | GGCAACTACT | 480 |
| ATTGTTCTGT | GACTCCCTGG | GTGAGGTCAC | CAACTGGTTC | CTGGCAGAGG | GAAGCCGAGA | 540 |
| TCCACTCCAG | GCCCATCTTT | ATAACTGTGA | AGATGGATGT | GCTGAACGCC | TTCAAGTACC | 600 |
| CGCTGCTGAT | CGGCGTGGGC | CTGTCCACAG | TCATCCGGCT | CCTGTCCTGC | CTCATTGGGT | 660 |
| ACTGCAGTTC | CCATTGGTGC | TGTAAGAAGG | AGGTGCGGGA | GACGCGTCGG | GAGCGCCGCA | 720 |
| GGCTCATGTC | CATGGAGATG | GATTAAGCAG | TTGGAGGGAC | AGAGGAACGT | TGTAGGAGCA | 780 |
| GTGGGGTGGG | GGGTGAGAAG | AGGACTCTGA | GATTTTACAA | CCGAGTGTGT | TACACTAAAA | 840 |
| CCGGTCCTCT | CTAATCTCAG | GTGGGACTCA | GCGCTCTCTC | TTTTCTGCAT | GTCAAGTTCC | 900 |
| GAGCGCGGAC | ATGTTTACCA | GCACACGGCT | CTTCTTCCCA | CGGCACTTTC | TGATATGTAA | 960 |
| CAATCGAGTG | TGTGTCTCCC | CCCCCCCGCT | GAAGCTGTTT | AATGGTT | | 1007 |

( 2 ) INFORMATION FOR SEQ ID NO:19:

( i ) SEQUENCE CHARACTERISTICS:
        ( A ) LENGTH: 632 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:19:

| GGCCGAGCAT | GGGGCGCCCG | GCGCCGAGGC | CGCTGCTGCT | GGCGCTCCTA | TCGCTGGCTG | 60 |
| TCTGCCGCGG | GCGTGTGGTG | AGAGTCCCTG | CGGGCACCCT | GGTTCGAGTG | GTGGGCACTG | 120 |
| AGCTGGTGAT | CCCCTGCAAT | GTCAGTGACT | ATGATGGCCC | CAGTGAGCAA | AACTTTGACT | 180 |
| GGAGCTTCTC | GTCTTCGGGA | AGCAGCTTTG | TGGCCTTCAA | GTACCCGCTG | CTGATCGGCG | 240 |
| TGGGCCTGTC | CACAGTCATC | GGGCTCCTGT | CCTGCCTCAT | TGGGTACTGC | AGTTCCCATT | 300 |
| GGTGCTGTAA | GAAGGAGGTG | CGGGAGACGC | GTCGGGAGCG | CCGCAGGCTC | ATGTCCATGG | 360 |
| AGATGGATTA | AGCAGTTGGA | GGGACAGAGG | AACGTTGTAG | GAGCAGTGGG | GTGGGGGTG | 420 |

```
AGAAGAGGAC  TCTGAGATTT  TACAACCGAG  TGTGTTACAC  TAAAACCGGT  CCTCTCTAAT      480

CTCAGGTGGG  ACTCAGCGCT  CTCTCTTTTC  TGCATGTCAA  GTTCCGAGCG  CGGACATGTT      540

TACCAGCACA  CGGCTCTTCT  TCCCACGGCA  CTTTCTGATA  TGTAACAATC  GAGTGTGTGT      600

CTCCCCCCCC  CCGCTGAAGC  TGTTTAATGG  TT                                      632
```

( 2 ) INFORMATION FOR SEQ ID NO:20:

( i ) SEQUENCE CHARACTERISTICS:
          ( A ) LENGTH: 932 base pairs
          ( B ) TYPE: nucleic acid
          ( C ) STRANDEDNESS: single
          ( D ) TOPOLOGY: linear ( i i ) MOLECULE TYPE: cDNA ( x i ) SEQUENCE DESCRIPTION: SEQ ID NO:20:

```
GGCCGAGCAT  GGGGCGCCCG  GCGCCGAGGC  CGCTGCTGCT  GGCGCTCCTA  TCGCTGGCTG       60

TCTGCCGCGG  GCGTGTGGTG  AGAGTCCCTG  CGGGCACCCT  GGTTCGAGTG  GTGGGCACTG      120

AGCTGGTGAT  CCCCTGCAAT  GTCAGTGACT  ATGATGGCCC  CAGTGAGCAA  AACTTTGACT      180

GGAGCTTCTC  GTCTTCGGGA  AGCAGCTTTG  TGGGGGAGA   TCTCATCAAG  TTGTTCTGTA      240

TCGTCACTGT  GGACGGAGCA  GTGCTGGACC  CAGATGACAT  GGCCTTCGAT  GTATCCTGGT      300

TTGCAGTACA  CTCTTTTGGC  TTGGACAAGG  CTCCCATCCT  CCTATCCTCC  TTGGACCGGA      360

AGGGAGTCGT  GACTACAGGC  CAGAGGGACT  GGAAGAGTAC  CGTCAGCCTG  GAGCGAGTGA      420

GCGTGCTGGA  ATTTTGCTG   CAAGTGCATA  GCTCTGAGGA  CCAGGACTTT  GGCAACTACT      480

ATTGTTCTGT  GACTCCCTGG  GTGAGGTCAC  CAACTGGTTC  CTGGCAGAGG  GAAGCCGAGA      540

TCCACTCCAG  GCCCATCTTT  ATAACTGTGA  AGATGGATGT  GCTGAACGCC  TTCAAGTACC      600

CGCTGCTGAT  CGGCGTGGGC  CTGTCCACAG  TCATCGGGCT  CCTGTCCTGC  CTCATTGGGT      660

ACATGGATTA  AGCAGTTGGA  GGGACAGAGG  AACGTTGTAG  GAGCAGTGGG  GTGGGGGGTG      720

AGAAGAGGAC  TCTGAGATTT  TACAACCGAG  TGTGTTACAC  TAAAACCGGT  CCTCTCTAAT      780

CTCAGGTGGG  ACTCAGCGCT  CTCTCTTTTC  TGCATGTCAA  GTTCCGAGCG  CGGACATGTT      840

TACCAGCACA  CGGCTCTTCT  TCCCACGGCA  CTTTCTGATA  TGTAACAATC  GAGTGTGTGT      900

CTCCCCCCCC  CCGCTGAAGC  TGTTTAATGG  TT                                      932
```

( 2 ) INFORMATION FOR SEQ ID NO:21:

( i ) SEQUENCE CHARACTERISTICS:
          ( A ) LENGTH: 734 base pairs
          ( B ) TYPE: nucleic acid
          ( C ) STRANDEDNESS: single
          ( D ) TOPOLOGY: linear ( i i ) MOLECULE TYPE: cDNA ( x i ) SEQUENCE DESCRIPTION: SEQ ID NO:21:

```
GGCCGAGCAT  GGGGCGCCCG  GCGCCGAGGC  CGCTGCTGCT  GGCGCTCCTA  TCGCTGGCTG       60

TCTGCCGCGG  GCGTGTGGTG  AGAGTCCCTG  CGGGCACCCT  GGTTCGAGTG  GTGGGCACTG      120

AGCTGGTGAT  CCCCTGCAAT  GTCAGTGACT  ATGATGGCCC  CAGTGAGCAA  AACTTTGACT      180

GGAGCTTCTC  GTCTTCGGGA  AGCAGCTTTG  TGGGGGAGA   TCTCATCAAG  TTGTTCTGTA      240

TCGTCACTGT  GGACGGAGCA  GTGCTGGACC  CAGATGACAT  GGCCTTCGAT  GTATCCTGGT      300

TTGCAGTACA  CTCTTTTGGC  TTGGACAAGG  CTCCCATCCT  CCTATCCTCC  TTGGACCGGA      360

AGGGAGTCGT  GACTACAGGC  CAGAGGGACT  GGAAGAGTAC  CGTCAGCCTG  GAGCGAGTGA      420
```

```
GCGTGCTGGA  ATTTTTGCTG  CAAGTGCATA  GCTCTGAGGA  CCAGATGGAT  TAAGCAGTTG     480

GAGGGACAGA  GGAACGTTGT  AGGAGCAGTG  GGGTGGGGGG  TGAGAAGAGG  ACTCTGAGAT     540

TTTACAACCG  AGTGTGTTAC  ACTAAACCG   GTCCTCTCTA  ATCTCAGGTG  GGACTCAGCG     600

CTCTCTCTTT  TCTGCATGTC  AAGTTCCGAG  CGCGGACATG  TTTACCAGCA  CACGGCTCTT     660

CTTCCCACGG  CACTTTCTGA  TATGTAACAA  TCGAGTGTGT  GTCTCCCCC   CCCCGCTGAA     720

GCTGTTTAAT  GGTT                                                          734
```

( 2 ) INFORMATION FOR SEQ ID NO:22:

( i ) SEQUENCE CHARACTERISTICS:
        ( A ) LENGTH: 557 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:22:

```
GGCCGAGCAT  GGGGCGCCCG  GCGCCGAGGC  CGCTGCTGCT  GGCGCTCCTA  TCGCTGGCTG      60

TCTGCCGCGG  GCGTGTGGTG  AGAGTCCCTG  CGGGCACCCT  GGTTCGAGTG  GTGGGCACTG     120

AGCTGGTGAT  CCCCTGCAAT  GTCAGTGACT  ATGATGGCCC  CAGTGAGCAA  AACTTTGACT     180

GGAGCTTCTC  GTCTTCGGGA  AGCAGCTTTG  TGGCCTTCAA  GTACCCGCTG  CTGATCGGCG     240

TGGGCCTGTC  CACAGTCATC  GGGCTCCTGT  CCTGCCTCAT  TGGGTACATG  GATTAAGCAG     300

TTGGAGGGAC  AGAGGAACGT  TGTAGGAGCA  GTGGGGTGGG  GGGTGAGAAG  AGGACTCTGA     360

GATTTTACAA  CCGAGTGTGT  TACACTAAAA  CCGGTCCTCT  CTAATCTCAG  GTGGGACTCA     420

GCGCTCTCTC  TTTTCTGCAT  GTCAAGTTCC  GAGCGCGGAC  ATGTTTACCA  GCACACGGCT     480

CTTCTTCCCA  CGGCACTTTC  TGATATGTAA  CAATCGAGTG  TGTGTCTCCC  CCCCCCGCT     540

GAAGCTGTTT  AATGGTT                                                       557
```

( 2 ) INFORMATION FOR SEQ ID NO:23:

( i ) SEQUENCE CHARACTERISTICS:
        ( A ) LENGTH: 554 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:23:

```
GGCCGAGCAT  GGGGCGCCCG  GCGCCGAGGC  CGCTGCTGCT  GGCGCTCCTA  TCGCTGGCTG      60

TCTGCCGCGG  GCGTGTGGTG  AGAGTCCCTG  CGGGCACCCT  GGTTCGAGTG  GTGGGCACTG     120

AGCTGGTGAT  CCCCTGCAAT  GTCAGTGACT  ATGATGGCCC  CAGTGAGCAA  AACTTTGACT     180

GGAGCTTCTC  GTCTTCGGGA  AGCAGCTTTG  TGGGTTCCCA  TTGGTGCTGT  AAGAAGGAGG     240

TGCGGGAGAC  GCGTCGGGAG  CGCCGCAGGC  TCATGTCCAT  GGAGATGGAT  TAAGCAGTTG     300

GAGGGACAGA  GGAACGTTGT  AGGAGCAGTG  GGGTGGGGGG  TGAGAAGAGG  ACTCTGAGAT     360

TTTACAACCG  AGTGTGTTAC  ACTAAAACCG  GTCCTCTCTA  ATCTCAGGTG  GGACTCAGCG     420

CTCTCTCTTT  TCTGCATGTC  AAGTTCCGAG  CGCGGACATG  TTTACCAGCA  CACGGCTCTT     480

CTTCCCACGG  CACTTTCTGA  TATGTAACAA  TCGAGTGTGT  GTCTCCCCC   CCCCGCTGAA     540

GCTGTTTAAT  GGTT                                                          554
```

( 2 ) INFORMATION FOR SEQ ID NO:24:

(i) SEQUENCE CHARACTERISTICS:
  (A) LENGTH: 201 base pairs
  (B) TYPE: nucleic acid
  (C) STRANDEDNESS: single
  (D) TOPOLOGY: linear (ii) MOLECULE TYPE: cDNA (xi) SEQUENCE DESCRIPTION: SEQ ID NO:24:

| | | | | | |
|---|---|---|---|---|---|
| GAATTCCACC | ATGGGGTACT | GCAGTTCCCA | TTGGTGCTGT | AAGAAGGAGG | TGCGGGAGAC | 60 |
| GCGTCGGGAG | CGCCGCAGGC | TCATGTCCAT | GGAGATGGAT | TAAGCAGTTG | GAGGGACAGA | 120 |
| GGAACGTTGT | AGGAGCAGTG | GGGTGGGGGG | TGAGAAGAGG | ACTCTGAGAT | TTTACAACCG | 180 |
| AGTGTGTTAC | AGGGCGGATC | C | | | | 201 |

(2) INFORMATION FOR SEQ ID NO:25:

(i) SEQUENCE CHARACTERISTICS:
  (A) LENGTH: 3729 base pairs
  (B) TYPE: nucleic acid
  (C) STRANDEDNESS: double
  (D) TOPOLOGY: linear (ii) MOLECULE TYPE: cDNA (xi) SEQUENCE DESCRIPTION: SEQ ID NO:25:

| | | | | | |
|---|---|---|---|---|---|
| CACGGCTGAG | AAGCCTGTTG | GGGACCTCTC | CAGTCCCAAT | GAAACCAAGT | ACATCATCTC | 60 |
| CCTGGACCAG | GATTCCGTGG | TGAAGCTGGA | GAACTGGACC | GACGCATCTC | GGGTGGACGG | 120 |
| CGTCGTGTTA | GAGAAGGTTC | AAGAGGATGA | GTTCCGATAC | CGAATGTACC | AGACTCAGGT | 180 |
| CTCCGATGCG | GGCCTGTACC | GCTGCATGGT | GACAGCCTGG | TCTCCTATCG | GGGGCAGCTT | 240 |
| GTGGCGAGAG | GCAGCGACCA | GTCTTTCCAA | TCCTATTGAG | ATTGACTTCC | AAACCTCAGG | 300 |
| TCCCATATTT | AACGCCTCTG | TGCATTCAGA | CACTCTGTCC | GTCACCCGGG | GAGATCTCAT | 360 |
| CAAGTTGTTC | TGTATCGTCA | CTGTGGACGG | AGCAGTGCTG | GACCCAGATG | ACATGGCCTT | 420 |
| CGATGTATCC | TGGTTTGCAG | TACACTCTTT | TGGCTTGGAC | AAGGCTCCCA | TCCTCCTATC | 480 |
| CTCCTTGGAC | CGGAAGGGAG | TCGTGACTAC | AGGCCAGAGG | GACTGGAAGA | GTACCGTCAG | 540 |
| CCTGGAGCGA | GTGAGCGTGC | TGGAATTTTT | GCTGCAAGTG | CATGGCTCTG | AGGACCAGGA | 600 |
| CTTTGGCAAC | TACTATTGTT | CTGTGACTCC | CTGGGTGAGG | TCACCAACTG | GTTCCTGGCA | 660 |
| GAGGGAAGCC | GAGATCCACT | CCAGGCCCAT | CTTTATAACT | GTGAAGATGG | ATGTGCTGAA | 720 |
| CGCCTTCAAG | TACCCGCTGC | TGATCGGCGT | GGGCCTGTCC | ACAGTCATCC | GGCTCCTGTC | 780 |
| CTGCCTCATT | GGGTACTGCA | GTTCCCATTG | GTGCTGTAAG | AAGGAGGTGC | GGGAGACGCG | 840 |
| TCGGGAGCGC | CGCAGGCTCA | TGTCCATGGA | GATGGATTAA | GCAGTTGGAG | GGACAGAGGA | 900 |
| ACGTTGTAGG | AGCAGTGGGG | TGGGGGGTGA | GAAGAGGACT | CTGAGATTTT | ACAACCGAGT | 960 |
| GTGTTACACT | AAAACCGGTC | CTCTCTAATC | TCAGGTGGGA | CTCAGCGCTC | TCTCTTTTCT | 1020 |
| GCATGTCAAG | TTCCGAGCGC | GGACATGTTT | ACCAGCACAC | GGCTCTTCTT | CCCACGGCAC | 1080 |
| TTTCTGATAT | GTAACAATCG | AGTGTGTGTC | TCCCCCCCCC | CGCTGAAGCT | GTTTAATGGT | 1140 |
| TAACCCCCGT | CTAATTAGTT | TTCTCCTAGC | AGCTTATCGA | TCCTCTGATT | CACGTGTGTT | 1200 |
| GATCACTTTT | GATTTAAGGG | ATCGCAGTGA | GGAAGGGCGA | AAGCATTCAG | AGTTGGTCAT | 1260 |
| CATGAGTAAG | AGGGTACCTG | CCCACCCGAA | AGCCAGCATC | CACAAGCAGC | CATCTGGAGA | 1320 |
| GCTGCTACCT | GCTGCTCTCT | ACCCTGGCCC | AGAACTGATA | GAGACCTGTG | CCAAGGCAAG | 1380 |
| CTGTGGCTAT | GACTACCCTG | CCCATCCCCC | ATTGTCAGGA | GTTAAACTA | TATTGGAACC | 1440 |

-continued

```
TAAACTCTAT AACTTCTTGA CCCCATAAGC CTTTTGTTTC CCTTTCTCCT CTACCCTCTT    1500
CTGTTTTCGG GTTTGTTTCT GTGAGAGTGA GGATATGGCA GCCCTGGAGT CTAGAATTTG    1560
GCTTTCCACC AAGCACCTTA TCTCGCCACC TTAGCCTTAA GAATGAGTAT GAAGAAAAAT    1620
CCACCACCAC CTCTGTCCAG GGCAGGTCTG TGAGGAGAGG ACACTGGGGA AGGAAAGGCA    1680
CAGATGCTTG CTTACTTGCT CACTCTGTAG TTCTGAGGCC GCTGTGCCTG CTCCAGGAAT    1740
CCAAGGGTGA GTGGGAGCAG AGGGCATCTG AGTTGTGCCG CTGAGCCAGG TGCCCTGTCC    1800
CTTCATGAGA GGCACTGTCC CTTGTACCCC CAGGACCAGC ATGGGAGCCA CAAATGTGCC    1860
ACATTGAGCT CCTTCCCAGG AAGGCAGATT GCTGCCTGCC AGACTGACTG ACTTCAAGGA    1920
ATCAGAAATT GCCTGGAGCA AGCGTGTGTT CTCTGTGACC TTTTTCAGTC CTTGAAGTCT    1980
TTTTAAGATC CCCGCAGGGG GTGGTGAAGA GGGGTATACT TTGTGGACGG TTTGCTTTCC    2040
TATTAGAAAC ACAAAGGGAA CCCAGCAATT TAGTGTTATG TGAATGGCCT GTAAAATAGG    2100
ATTGAAGGCA GCCGGCTCTG CCTGACTGGG CCCAGCAGGA ATAGGACAGA GGGCAGGCAC    2160
ACCTTCCAGG TCACCAGTGC CTGCTCCATC AGGGCCTCAG CCATGCAAAG TCTCTCGCCC    2220
TAGCATAGCC TTCCAGGAGC CTCCGATAGG TACTGAGGCT CATCAGCCAC CCGGTACCCT    2280
CACCCTACCC TCTACCTCTG AAGGATTTAA CATTGTTGTC TTCCAAAGGG GAGTGGGGGA    2340
GGAGAGCTCC TTTCTCTTAA GCAATAAAGT AATAAGAAAA GATGGCCATT CACGGGCAGC    2400
TCTAGTCACC ATGGGACCGG ATGCGCTGAG CTCCCCCCTC CCACCTTCT CTCCATGTGG     2460
CCCATGGTGG CTTTTGTATT TGCCACCCAG TTTCCTCTGC TTGTTTCGAG CCCACCTTGG    2520
AGACTGCTCT TATGATGAGA TTCTGAGCCG GTGGCTCTAG CCCAGGTGGG GGGTACAGGT    2580
TTAGAGTCGG TAGCAAGAAG AGGGACAGCA GGTGCACCCC ACACAAGCAA GAGAGGCCAG    2640
AGAAAGAGGG GAGGCTTCGG AAGACATGGC TGTTCTACAT GTCGCTCTCT TATTGCTAGC    2700
TCAGACGTGA GGCACAGGTG ACTGTACAAA CAGGAATTAG GGGAGTAGAA CCAAGTATTA    2760
GGAACTTCAA GCCTGTGCCA TTACTGGAGA AGATTCAGGG CCTTTGCAGT GCAGCCCTCC    2820
TTAGGAGGAC AAGAGAGATT TAGCCTTGGA TGAGTTGAGG TGAGCCCTAG CTGTACATGA    2880
ACCCACAGAG GTCCAAGCGG GTAACTGATG GTGAGAGATG AGTGATCGGT CCTACCTTCC    2940
CCTTTCCCTT TTGTCTGATG TTGAGATTTG AACCTGAGTT GTGGAGGTCA TGCCCAAACC    3000
CCTCCATGTT GCTTAGGGCT GGAAGAGGGA CCAGAAACCC CAGGACCTAG TTCCTTTTGG    3060
GAATATTGGC ATTCTGGGGT ATGTGTCTTT TTAAGTGTGG TCAAACACTC TTGATGTACC    3120
AAATAGTGTT CCCCGTGAAG CGCTCTTCCT GAGGCTCCCA CCCAGCAACA CTGGTCTGAG    3180
GGAAGGAAAG GCCAAACCAG GCCTGGGCAC ATGAAATTGC ACTTCTTAAA GAGAAACTTT    3240
TTAGAAGGTT GGGTATTTTT CTTAATCACA AAAATCTCCC ACTGAAAGAA CCTAAGCTAC    3300
ATTCAGATCG AAGCCTCTAA ATTAAATTGT TTACTTTACA ATGTTACAC ACATGACTCA     3360
CTTTTTTAGA AAAATAAGAA AACTGCAAAC TCCGGCTTTT TAACAACTTT TCAGCTTTTT    3420
CATGCATGGG ATAGATATGC TGGCAACCTG ACTCACCAGC TGGATCAAAT CCTCATTTAG    3480
AAATGTCCCG ATATGTGGAT ATATGTGTCT TCCCCCCTCC CAACCACACA GCTCCCTCCT    3540
GCCCAGACCT CTGTCTGTTT CTCTGGTGGC TTTTGCCTCC TGCTTTGCAG ACCGCCTGCA    3600
GCCATGATTT TGTTACGGCA TCCACGAGCC AAAGACTGCG CCTTGGGAGC AGGAACAATA    3660
AGCAATACTA CACCACTCGC TACTGTCGGG GGTCTTTTTC TCTTATTTGT TTTTGTTTTT    3720
ATTTTATTA                                                            3729
```

( 2 ) INFORMATION FOR SEQ ID NO:26:

( i ) SEQUENCE CHARACTERISTICS:
  ( A ) LENGTH: 836 base pairs
  ( B ) TYPE: nucleic acid
  ( C ) STRANDEDNESS: double
  ( D ) TOPOLOGY: linear ( i i ) MOLECULE TYPE: cDNA ( x i ) SEQUENCE DESCRIPTION: SEQ ID NO:26:

| | | | | | | |
|---|---|---|---|---|---|---|
| CACGGCTGAG | AAGCCTGTTG | GGGACCTCTC | CAGTCCCAAT | GAAACCAAGT | ACATCATCTC | 60 |
| CCTGGACCAG | GATTCCGTGG | TGAAGCTGGA | GAACTGGACC | GACGCATCTC | GGGTGGACGG | 120 |
| CGTCGTGTTA | GAGAAGGTTC | AAGAGGATGA | GTTCCGATAC | CGAATGTACC | AGACTCAGGT | 180 |
| CTCCGATGCG | GGCCTGTACC | GCTGCATGGT | GACAGCCTGG | TCTCCTATCG | GGGGCAGCTT | 240 |
| GTGGCGAGAG | GCAGCGACCA | GTCTTTCCAA | TCCTATTGAG | ATTGACTTCC | AAACCTCAGG | 300 |
| TCCCATATTT | AACGCCTCTG | TGCATTCAGA | CACTCTGTCC | GTCACCCGGG | GAGATCTCAT | 360 |
| CAAGTTGTTC | TGTATCGTCA | CTGTGGACGG | AGCAGTGCTG | GACCCAGATG | ACATGGCCTT | 420 |
| CGATGTATCC | TGGTTTGCAG | TACACTCTTT | TGGCTTGGAC | AAGGCTCCCA | TCCTCCTATC | 480 |
| CTCCTTGGAC | CGGAAGGGAG | TCGTGACTAC | AGGCCAGAGG | GACTGGAAGA | GTACCGTCAG | 540 |
| CCTGGAGCGA | GTGAGCGTGC | TGGAATTTTT | GCTGCAAGTG | CATGGCTCTG | AGGACCAGGA | 600 |
| CTTTGGCAAC | TACTATTGTT | CTGTGACTCC | CTGGGTGAGG | TCACCAACTG | GTTCCTGGCA | 660 |
| GAGGGAAGCC | GAGATCCACT | CCAGGCCCAT | CTTTATAACT | GTGAAGATGG | ATGTGCTGAA | 720 |
| CGCCTTCAAG | TACCCGCTGC | TGATCGGCGT | GGGCCTGTCC | ACAGTCATCC | GGCTCCTGTC | 780 |
| CTGCCTCATT | GGGTACTGCA | GTTCCCATTG | GTGCTGTAAG | AAGGAGGTGC | GGGAGA | 836 |

( 2 ) INFORMATION FOR SEQ ID NO:27:

( i ) SEQUENCE CHARACTERISTICS:
    ( A ) LENGTH: 133 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:27:

| | | | | | | |
|---|---|---|---|---|---|---|
| GGATTTTCCG | TAGACAAAGA | GGTCTCGTGT | ATTTTGTCC | CTATCCAAGG | TTATACAAAC | 60 |
| TAATTGTGTT | GTTTTATACT | GTGGCCACAA | ATATTATGCA | ATGCACCATT | TGTTTTGTT | 120 |
| TTTATTTTAT | TAA | | | | | 133 |

( 2 ) INFORMATION FOR SEQ ID NO:28:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:28:

CCTCCCAGGT GCTGGCG                                                                       17

( 2 ) INFORMATION FOR SEQ ID NO:29:

( i ) SEQUENCE CHARACTERISTICS:
    ( A ) LENGTH: 32 base pairs
    ( B ) TYPE: nucleic acid
    ( C ) STRANDEDNESS: single ( D ) TOPOLOGY: linear ( i i ) MOLECULE TYPE: DNA ( x i ) SEQUENCE DESCRIPTION: SEQ ID NO:29:

AAGCTGCTTC CCGAAGACGA GAAGCTCCAG TC  32

( 2 ) INFORMATION FOR SEQ ID NO:30:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:30:

CTGAATTCTA GATCGATG  18

( 2 ) INFORMATION FOR SEQ ID NO:31:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:31:

GAGACTTAAG ATCTAGCTAC  20

( 2 ) INFORMATION FOR SEQ ID NO:32:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:32:

GCTCACTGGG GCCATCA  17

( 2 ) INFORMATION FOR SEQ ID NO:33:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:33:

GGAGGCGGAG AGTCGCT  17

( 2 ) INFORMATION FOR SEQ ID NO:34:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:34:

GGACTCTCAC CACACGC					17

( 2 ) INFORMATION FOR SEQ ID NO:35:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:35:

AGCGCCAGCA GCAGCGG					17

( 2 ) INFORMATION FOR SEQ ID NO:36:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:36:

CAGCGCCCAG GAGGAGGAG					19

( 2 ) INFORMATION FOR SEQ ID NO:37:

( i ) SEQUENCE CHARACTERISTICS:
        ( A ) LENGTH: 69 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:37:

GGAGGCGGAG AGTCGCTCCC GCCGGCCGAG CATGGGCGC CCGGCGCCGA GGCCGCTGCT					60

GCTGGCGCT					69

( 2 ) INFORMATION FOR SEQ ID NO:38:

( i ) SEQUENCE CHARACTERISTICS:
        ( A ) LENGTH: 177 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:38:

CTGTCTGCCG CGGGCGTGTG GTGAGAGTCC CTGCGGGCAC CCTGGTTCGA GTGGTGGGCA					60

CTGAGCTGGT GATCCCCTGC AATGTCAGTG ACTATGATGG CCCCAGTGAG CAAAACTTTG					120

ACTGGAGCTT CTCGTCTTCG GGAAGCAGCT TTGTGGAGCT CGCCAGCACC TGGGAGG					177

( 2 ) INFORMATION FOR SEQ ID NO:39:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:39:

Arg Val Val Arg Val Pro Ala Gly Ser Leu Val Arg Val Val Gly Thr
        5                       10                      15

Glu Leu Val Ile Pro
         20

( 2 ) INFORMATION FOR SEQ ID NO:40:

( i ) SEQUENCE CHARACTERISTICS:
          ( A ) LENGTH: 17 base pairs
          ( B ) TYPE: nucleic acid
          ( C ) STRANDEDNESS: single
          ( D ) TOPOLOGY: linear ( i i ) MOLECULE TYPE: DNA ( x i ) SEQUENCE DESCRIPTION: SEQ ID NO:40:

ATCACWGAYT TCTTTGG 17

( 2 ) INFORMATION FOR SEQ ID NO:41:

( i ) SEQUENCE CHARACTERISTICS:
          ( A ) LENGTH: 16 base pairs
          ( B ) TYPE: nucleic acid
          ( C ) STRANDEDNESS: single
          ( D ) TOPOLOGY: linear ( i i ) MOLECULE TYPE: DNA ( x i ) SEQUENCE DESCRIPTION: SEQ ID NO:41:

TGATTCCAYG TTGCAT 16

( 2 ) INFORMATION FOR SEQ ID NO:42:

( i ) SEQUENCE CHARACTERISTICS:
          ( A ) LENGTH: 46 base pairs
          ( B ) TYPE: nucleic acid
          ( C ) STRANDEDNESS: single
          ( D ) TOPOLOGY: linear ( i i ) MOLECULE TYPE: DNA ( x i ) SEQUENCE DESCRIPTION: SEQ ID NO:42:

GAATTCAGGA TGCAGTTCCT GGTTGCGTTG CTCCTGCTGA GTGCAG 46

( 2 ) INFORMATION FOR SEQ ID NO:43:

( i ) SEQUENCE CHARACTERISTICS:
          ( A ) LENGTH: 46 base pairs
          ( B ) TYPE: nucleic acid
          ( C ) STRANDEDNESS: single
          ( D ) TOPOLOGY: linear ( i i ) MOLECULE TYPE: DNA ( x i ) SEQUENCE DESCRIPTION: SEQ ID NO:43:

CTGCACTCAG CAGGAGCAAC GCAACCAGGA ACTGCATCCT GAATTC 46

( 2 ) INFORMATION FOR SEQ ID NO:44:

( i ) SEQUENCE CHARACTERISTICS:
          ( A ) LENGTH: 17 amino acids
          ( B ) TYPE: amino acid
          ( D ) TOPOLOGY: linear ( i i ) MOLECULE TYPE: peptide ( x i ) SEQUENCE DESCRIPTION: SEQ ID NO:44:

Met Gln Phe Leu Val Ala Leu Leu Leu Leu Ser Ala Ala Val Cys His

```
                1                       5                          10                          15
Gly
17

( 2 ) INFORMATION FOR SEQ ID NO:45:

( i ) SEQUENCE CHARACTERISTICS:
                  ( A ) LENGTH: 17 amino acids
                  ( B ) TYPE: amino acid
                  ( D ) TOPOLOGY: linear ( i i ) MOLECULE TYPE: peptide ( x i ) SEQUENCE DESCRIPTION: SEQ ID NO:45:

Met Gln Phe Leu Val Ala Leu Leu Leu Leu Ser Val Ala Val Ala Arg
                        5                         10                          15
Ala
17

( 2 ) INFORMATION FOR SEQ ID NO:46:

( i ) SEQUENCE CHARACTERISTICS:
                  ( A ) LENGTH: 19 base pairs
                  ( B ) TYPE: nucleic acid
                  ( C ) STRANDEDNESS: single
                  ( D ) TOPOLOGY: linear ( i i ) MOLECULE TYPE: DNA ( x i ) SEQUENCE DESCRIPTION: SEQ ID NO:46:

ACAAATGGTG CATTGCATA                                                                                    19

( 2 ) INFORMATION FOR SEQ ID NO:47:

( i ) SEQUENCE CHARACTERISTICS:
                  ( A ) LENGTH: 19 base pairs
                  ( B ) TYPE: nucleic acid
                  ( C ) STRANDEDNESS: single
                  ( D ) TOPOLOGY: linear ( i i ) MOLECULE TYPE: DNA ( x i ) SEQUENCE DESCRIPTION: SEQ ID NO:47:

ACGTTGACTT TCCTTTTAA                                                                                    19

( 2 ) INFORMATION FOR SEQ ID NO:48:

( i ) SEQUENCE CHARACTERISTICS:
                  ( A ) LENGTH: 146 base pairs
                  ( B ) TYPE: nucleic acid
                  ( C ) STRANDEDNESS: single
                  ( D ) TOPOLOGY: linear ( i i ) MOLECULE TYPE: DNA ( x i ) SEQUENCE DESCRIPTION: SEQ ID NO:48:

AGAGGAGGAG GAGGAGAGGC GGCGGGGAAG GAGGAGGAGG GGGAGAGTCG CTCCCGCCGG           60

GCGAGCATGG GGGCGCCTGG CCTCGAGGCC GCTGCTGCTG GCGCTCCTGT CGTTGGGTGA          120

GTGTGCGCGG GGCTCAGCGG GGCACA                                               146

( 2 ) INFORMATION FOR SEQ ID NO:49:

( i ) SEQUENCE CHARACTERISTICS:
                  ( A ) LENGTH: 2906 base pairs
                  ( B ) TYPE: nucleic acid
                  ( C ) STRANDEDNESS: single
                  ( D ) TOPOLOGY: linear
```

( i i ) MOLECULE TYPE: cDNA ( x i ) SEQUENCE DESCRIPTION: SEQ ID NO:49:

| | | | | | |
|---|---|---|---|---|---|
| CCTTGTTCTT | AACCATATTT | ATTATTCTGA | TCAAAACACT | CATTGAAGCT | TTATTATTCC | 60 |
| GGAAATCTAG | GATATTAGTC | TCCAATTTTT | TTTAAAACAT | GCATAAAATA | TTTAAGGTAA | 120 |
| GATATGAAGA | AGATGGTGTG | CTCATTGCTA | TTCTTTACTT | TGTGGATAAA | TTGTATAGCA | 180 |
| TATTAGAAAC | CGGATCTGGA | GTTAAACTGG | TCCAGATGAT | TCAGAGCTCC | ATAGAGCTTG | 240 |
| ATTACATGTC | TCGGTCCCAG | GTGACGGTTT | TGGGCTCCTT | CAGAGTGACG | TGTTAACTC | 300 |
| TGCAAGATAT | ACATCGGTCT | CGGTGGGTGT | GAATTCAGTG | TGAGCCAGGA | TGTAGAAAGA | 360 |
| CCAGTCCTTG | CTGAAGGACA | GATCTGACAT | CTCGATATTT | GGTATCTTCT | TTCCATTCTT | 420 |
| CAGTAGCTCA | ATTTCTATCT | GAGGTGGGTG | GAACTGAGAC | ACGTAGCAGT | TGAGGAAGTT | 480 |
| GGGCTTCCCA | TTCTCCGGTG | GATGGCGAGA | GTACACTTGA | ATTTGGGGAG | TTTTCTGAAT | 540 |
| GGCAAGCACG | ACGGCCAGAG | AGACAAGCAC | CAGAAAGATC | ACGGTCACCG | AGCGAGCCAT | 600 |
| CGTGCCGGTC | CGGTCAGCAG | GACGCATCAG | GATGGTTGTT | CTGTTTGTT | TGTTTCTTG | 660 |
| AGATTGCTCT | TTCTAGGGAA | GTGAACTGAC | AGGAGTCCGC | TTGGGTGGTA | TCTCTACCTG | 720 |
| GAAAGAGAAA | AACAGAACTA | GGGAGCAGAT | GCACACTGTT | GTCAGACTTC | TGCAACCTGA | 780 |
| CTTATGATAG | GCTGGGCAAA | CTCATCCCAC | CCAGGGTGC | TGAGGCACTT | GGCTCTAAAT | 840 |
| GTCAGATGAC | TGGCAATTGG | GTCGTTCTGA | TTCCTGTCCT | GTGTGCTGCA | GATGTCTGCA | 900 |
| CTTCGAGGCT | GCACAGTCGT | GACAGAGAGA | TGACTTGAGG | GGACGGCGT | TTATCTCCAC | 960 |
| AACGATGTCC | ATAAACAGTT | CCAAGCAGCC | GGTGTCCTCT | GCAGCTGGAC | TCATCGCCAA | 1020 |
| CACGACTTGC | CAGACGGAGA | ACCGGCTTTC | AGTGTTCTTT | TCAATAATCT | TCATGACGGT | 1080 |
| GGGGATTGTA | TCTAACAGCC | TGGCCATTGC | CATCCTCATG | AAGGCATATC | AGAGATTTAG | 1140 |
| ACGGAAGTCG | AAGGCTTCTT | TCCTGCTCTT | GGCTAGTGGC | CTGGTGATCA | CAGACTTCTT | 1200 |
| CGGCCACCTC | ATCAACGGAG | GGATAGCTGT | CTTCGTATAC | GCTTCTGATA | AAGACTGGAT | 1260 |
| CCGCTTCGAT | CAATCGAACA | TCCTGTGCAG | TGTTTTTGGG | ATGTCCATGG | TGTTCTCTGG | 1320 |
| CTTGTGCCCA | CTTTTCCTGG | GCAGTACGAT | GGCCATTGAG | AGGTGCATCG | GGTCACCAA | 1380 |
| CCCTCTATTC | CACTCTACAA | AGATCACGTC | TAAGCATGTG | AAAATGATAC | TGAGCGGTGT | 1440 |
| GTGCATGTTT | GCTGTCTTCG | TGGCCCTGTT | GCCCATCCTT | GGACACCGAG | ATTATCAAAT | 1500 |
| CCAAGCATCC | AGAACTTGGT | GCTTCTACAA | CACAGAGCAC | ATCGAAGACT | GGAAGACAG | 1560 |
| GTTCTATCTC | TTGTTCTTTT | CTTCCCTGGG | ACTCTTAGCT | CTCGGCATCT | CATTCTCGTG | 1620 |
| CAACGCCGTC | ACGGGAGTCA | CACTTTTGAG | AGTGAAGTTT | AGAAGTCAGC | AGCACAGGCA | 1680 |
| AGGCAGGTCT | CACCACCTGG | AGATGGTGAT | TCAGCTCCTG | GCCATAATGT | GTGTCTCCTG | 1740 |
| CGTCTGCTGG | AGTCCCTTTC | TGGTGACGAT | GGCCAACATT | GCAATCAATG | GAAATAATTC | 1800 |
| CCCAGTGACC | TGTGAGACGA | CGCTCTTTGC | TCTCCGAATG | GCAACCTGGA | ACCAGATATT | 1860 |
| AGACCCCTGG | GTCTACATTC | TGCTACGGAA | GGCTGTCCTT | AGGAACCTGT | ACAAGCTTGC | 1920 |
| CAGTCGCTGC | TGTGGAGTGA | ACATCATCAG | CTTGCACATC | TGGGAACTCA | GCTCCATCAA | 1980 |
| GAATTCCTTA | AAGGTTGCTG | CTATCTCTGA | GTCACCGGCT | GCAGAGAAGG | AGAATCAGCA | 2040 |
| AGCATCTAGT | GAGGCTGGAC | TGTAAGTCAA | TGCACAGCTA | GAAGAAAGTT | ATGGGAACTT | 2100 |
| CCGAAACATC | TTACCTGACC | AGACTCAGAG | CATAACTGGA | ACACTTGGAC | CTCTGTGTGT | 2160 |
| AGTTCGGGAG | TACACTGGTC | AGACAAAGCT | TCTGACTTTT | GTTATGCTGG | CTGCTGCATG | 2220 |
| GTTGTGCATT | TTCATTTGTT | GGTGTCAACA | GGAGATTCAA | CATGGTGGAG | TTAAGTAGAG | 2280 |

```
TACACATTTT ATCTGCGTGA CTTATGTTTT TGGAATAAAT GAATCTGTTG AGGCCCTGTG      2340

CCTTTATTTG ACCTATTTTT CCAAGCACCT TAATGCTACC TGCACCGTGA CATGGCCATT      2400

TGAGGAGCAC TGACTTGCAG ACAAAGCTTA AAGTAACACA AGACTTTTTG TGTTGTGTGT      2460

GCAGCTCTGC TCTGTTTACC AACCCACGTG TCCTCAATGT CTGCATGACC ATGACATCTG      2520

AGTCTCATGG TGACTTTGAT GGCCACTATG TAGGCAGCTC AGCTTGACAT TGTGGGGCTG      2580

ATGAGGATAA TCATTCTTGT CACAACTCAC ATGTGTGGTT GCTTGCATTT GTTGTTGTGA      2640

AGGTCAATTA TTTTTCCAC ATTGGCTGTC CTCCTATAAA GTCATAGGTT TTCAGTGTCT        2700

AAGTAATCCC CCTTTCCTCT GAAAATTGTA GAGGAATACA GGCTTTATCT TAGCACAGAT      2760

TCAGCTCATG ATAGCATATC ATAAAGCCCT ATTGTGGATG ATGCAAACAT TGAAATCCCA      2820

CTTACACATG CCAAGAACAT GGCAGACATT GCTTTACCTG AGCTATCATT TCTGTGTCAG      2880

AGAATAAAAA ACGATCAAGA CACAAA                                                                  2906
```

(2) INFORMATION FOR SEQ ID NO:50:

(i) SEQUENCE CHARACTERISTICS:
        (A) LENGTH: 366 amino acids
        (B) TYPE: amino acid
        (D) TOPOLOGY: linear (ii) MOLECULE TYPE: peptide (xi) SEQUENCE DESCRIPTION: SEQ ID NO:50:

```
Met Ser Ile Asn Ser Ser Lys Gln Pro Val Ser Ser Ala Ala Gly Leu
  1               5                  10                  15

Ile Ala Asn Thr Thr Cys Gln Thr Glu Asn Arg Leu Ser Val Phe Phe
                 20                  25                  30

Ser Ile Ile Phe Met Thr Val Gly Ile Val Ser Asn Ser Leu Ala Ile
             35                  40                  45

Ala Ile Leu Met Lys Ala Tyr Gln Arg Phe Arg Arg Lys Ser Lys Ala
         50                  55                  60

Ser Phe Leu Leu Leu Ala Ser Gly Leu Val Ile Thr Asp Phe Phe Gly
 65                  70                  75                  80

His Leu Ile Asn Gly Gly Ile Ala Val Phe Val Tyr Ala Ser Asp Lys
                 85                  90                  95

Asp Trp Ile Arg Phe Asp Gln Ser Asn Ile Leu Cys Ser Val Phe Gly
                100                 105                 110

Met Ser Met Val Phe Ser Gly Leu Cys Pro Leu Phe Leu Gly Ser Thr
            115                 120                 125

Met Ala Ile Glu Arg Cys Ile Gly Val Thr Asn Pro Leu Phe His Ser
        130                 135                 140

Thr Lys Ile Thr Ser Lys His Val Lys Met Ile Leu Ser Gly Val Cys
145                 150                 155                 160

Met Phe Ala Val Phe Val Ala Leu Leu Pro Ile Leu Gly His Arg Asp
                165                 170                 175

Tyr Gln Ile Gln Ala Ser Arg Thr Trp Cys Phe Tyr Asn Thr Glu His
                180                 185                 190

Ile Glu Asp Trp Glu Asp Arg Phe Tyr Leu Leu Phe Phe Ser Ser Leu
            195                 200                 205

Gly Leu Leu Ala Leu Gly Ile Ser Phe Ser Cys Asn Ala Val Thr Gly
        210                 215                 220

Val Thr Leu Leu Arg Val Lys Phe Arg Ser Gln Gln His Arg Gln Gly
225                 230                 235                 240
```

|     |     |     |     |     |     |     |     |     |     |     |     |     |     |     |
| --- | --- | --- | --- | --- | --- | --- | --- | --- | --- | --- | --- | --- | --- | --- |
| Arg | Ser | His | His | Leu 245 | Glu | Met | Val | Ile | Gln 250 | Leu | Leu | Ala | Ile | Met 255 | Cys |
| Val | Ser | Cys | Val 260 | Cys | Trp | Ser | Pro | Phe 265 | Leu | Val | Thr | Met | Ala 270 | Asn | Ile |
| Ala | Ile | Asn 275 | Gly | Asn | Asn | Ser | Pro 280 | Val | Thr | Cys | Glu | Thr 285 | Thr | Leu | Phe |
| Ala | Leu | Arg 290 | Met | Ala | Thr | Trp 295 | Asn | Gln | Ile | Leu | Asp 300 | Pro | Trp | Val | Tyr |
| Ile 305 | Leu | Leu | Arg | Lys | Ala 310 | Val | Leu | Arg | Asn | Leu 315 | Tyr | Lys | Leu | Ala | Ser 320 |
| Arg | Cys | Cys | Gly | Val 325 | Asn | Ile | Ile | Ser | Leu 330 | His | Ile | Trp | Glu | Leu 335 | Ser |
| Ser | Ile | Lys | Asn 340 | Ser | Leu | Lys | Val | Ala 345 | Ala | Ile | Ser | Glu | Ser 350 | Pro | Ala |
| Ala | Glu | Lys 355 | Glu | Asn | Gln | Gln | Ala 360 | Ser | Ser | Glu | Ala | Gly 365 | Leu |     |     |

( 2 ) INFORMATION FOR SEQ ID NO:51:

( i ) SEQUENCE CHARACTERISTICS:
        ( A ) LENGTH: 2898 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:51:

```
GAATTCAGGA TGCAGTTCCT GGTTGCGTTG CTCCTGCTGA GTGCAGCTGT CTGCCGCGGG      60
CGTGTGGTGA GAGTCCCTGC GGGCACCCTG GTTCGAGTGG TGGGCACTGA GCTGGTGATC     120
CCCTGCAATG TCAGTGACTA TGATGGCCCC AGTGAGCAAA ACTTTGACTG GAGCTTCTCG     180
TCTTCGGGAA GCAGCTTTGT GGAGCTCGCC AGCACCTGGG AGGTGGGCTT CCCGGCGCAG     240
CAGTACCGTG AGCGGCTGCA GCGGGGCGAC ATCCTGTTGA GGAGGACAGC CAATGATGCT     300
GTGGAGCTGC ACATAAAGAA TGTCCAGCCC TCGGACCAAG GCCACTACAA GTGTTCAACT     360
CCAAGCACAG ACGCCACCGT CCAGGGCAAC TATGAGGACA CAATGCAGGT TAAAGTGCTG     420
GCAGATGCCC TGGTGGTGGG CCCCAGCTCC CGGCCTCCTC CAGGCCTGAG CCTGCGCGAG     480
GGGGAGCCCT TTGAACTTCG ATGTATCGCA TCTACTACGT CACCGTTGCA CACACACCTG     540
GCACTTCGGT GGGAACTGCA CCGTGGCCCA GTGCACCGAA GCATCCTAGC CCTAAGCCAC     600
GAGGGCAGGT TCACCCAGG ACCTGGCTAT GAACAGCGCT ACCACAGTGG GGATGTACGC     660
CTGGACACGG TGGGCAGCGA TGCCTACCGC CTCTCCGTAG CCCGGGCACT CTCTGCAGAC     720
CAGGGTTCCT ACAGATGTGT GGTCAGTGAG TGGATCACAG AGCAAGGCAG CTGGCAAGAA     780
ATCCAAGAAA AAGCTGTGGA AGTGGCCACT GTGGTGATCC AGCCAACAGC TCTGCAACTG     840
GCCGTGCCCA GGACAGTGTC TGTGACCGAA GGAAAGGACC TGGACCTTTC TTGCAACATC     900
ACAACAGACC GTGTGGATGA TGTCCGGCCT GAGGTGACAT GGTACTTCAA AAAGACACCC     960
GATACCTCTT TGCTTGCCTC CCATATGCTG GCTCGGCTGG ACCGTGATTC CCTGGTACAC    1020
AGCTCACCAC ACGTTGCTCT CAGCCACGTG GATACCCGCT CTTACCATCT ACTGGTGCGA    1080
GATGTTAGCA AGAAAACTC CGGTTACTAT CTATGCCTCG TGGCCCTCTG GGCTCCTGGA    1140
CACAACCGGA GCTGGCACAA GGTGGCAGAG CCATGTCTG CCCCATCTGG TGTAAGCGTG    1200
ACCTGGCTAG AACCAGAATA CCAGGTCTAC CTGAATGCTT CTAAGGTCCC CGGGTTTTCC    1260
GACGACCCCA CAGAACTGCA ATGCCGGGTG ATAGACACGA AGCGTGTGGA TGCCGGTGTC    1320
```

| | | | | | |
|---|---|---|---|---|---|
| CGACTTACTG | TGTCGTGGTA | CTATAGAATG | AACCGTCGCA | ATGATGACGT | GGTGGCCAGC | 1380
| GAGCTTCTCG | CCGTCATGGA | CGGGGACTGG | ACTCTGAGAT | ACGGGGAGAG | AAGCAAACAG | 1440
| CGGGCCCAGG | ACGGCGAGTT | TATCTTTTCT | AAGGAGCACA | CAGACACATT | CAGTTTCCGG | 1500
| ATCCAAAGGA | CTACGGAGGA | AGACAGGGGC | AGTTATTACT | GTGTTGTGTC | TGCCTGGACC | 1560
| AGGCAGAGGA | ACAGCAGCTG | GGTGAAGAGC | AAAGATGTCT | TCTCCAAGCC | CGTCAACATA | 1620
| TTCTGGGCCT | CGGAAGATTC | TGTGCTCGTG | GTGAAGGCAC | GGCAGCCAAA | GCCTTTCTTT | 1680
| GCTGCAGGGA | ATACATTTGA | GATGACTTGC | AAAGTGTCTT | CCAAGAATAT | TAAGTCTCCA | 1740
| CGATACTCTG | TTCTCATCAC | GGCTGAGAAG | CCTGTTGGGG | ACCTCTCCAG | TCCCAATGAA | 1800
| ACCAAGTACA | TCATCTCCCT | GGACCAGGAT | TCCGTGGTGA | AGCTGGAGAA | CTGGACCGAC | 1860
| GCATCTCGGG | TGGACGGCGT | CGTGTTAGAG | AAGGTTCAAG | AGGATGAGTT | CCGATACCGA | 1920
| ATGTACCAGA | CTCAGGTCTC | CGATGCGGGC | CTGTACCGCT | GCATGGTGAC | AGCCTGGTCT | 1980
| CCTATCGGGG | GCAGCTTGTG | GCGAGAGGCA | GCGACCAGTC | TTTCCAATCC | TATTGAGATT | 2040
| GACTTCCAAA | CCTCAGGTCC | CATATTTAAC | GCCTCTGTGC | ATTCAGACAC | TCTGTCCGTC | 2100
| ACCCGGGGAG | ATCTCATCAA | GTTGTTCTGT | ATCGTCACTG | TGGACGGAGC | AGTGCTGGAC | 2160
| CCAGATGACA | TGGCCTTCGA | TGTATCCTGG | TTTGCAGTAC | ACTCTTTTGG | CTTGGACAAG | 2220
| GCTCCCATCC | TCCTATCCTC | CTTGGACCGG | AAGGGAGTCG | TGACTACAGG | CCAGAGGGAC | 2280
| TGGAAGAGTA | CCGTCAGCCT | GGAGCGAGTG | AGCGTGCTGG | AATTTTTGCT | GCAAGTGCAT | 2340
| AGCTCTGAGG | ACCAGGACTT | TGGCAACTAC | TATTGTTCTG | TGACTCCCTG | GGTGAGGTCA | 2400
| CCAACTGGTT | CCTGGCAGAG | GGAAGCCGAG | ATCCACTCCA | GGCCCATCTT | TATAACTGTG | 2460
| AAGATGGATG | TGCTGAACGC | CTTCAAGTAC | CCGCTGCTGA | TCGGCGTGGG | CCTGTCCACA | 2520
| GTCATCGGGC | TCCTGTCCTG | CCTCATTGGG | TACTGCAGTT | CCCATTGGTG | CTGTAAGAAG | 2580
| GAGGTGCGGG | AGACGCGTCG | GGAGCGCCGC | AGGCTCATGT | CCATGGAGAT | GGATTAAGCA | 2640
| GTTGGAGGGA | CAGAGGAACG | TTGTAGGAGC | AGTGGGGTGG | GGGGTGAGAA | GAGGACTCTG | 2700
| AGATTTTACA | ACCGAGTGTG | TTACACTAAA | ACCGGTCCTC | TCTAATCTCA | GGTGGGACTC | 2760
| AGCGCTCTCT | CTTTTCTGCA | TGTCAAGTTC | CGAGCGCGGA | CATGTTTACC | AGCACACGGC | 2820
| TCTTCTTCCC | ACGGCACTTT | CTGATATGTA | ACAATCGAGT | GTGTGTCTCC | CCCCCCCGC | 2880
| TGAAGCTGTT | TAATGGTT | | | | | 2898

NUCLEIC ACID ENCODING PROSTAGLANDIN $F_{2\alpha}$ RECEPTOR REGULATORY PROTEIN

STATE AS TO FEDERALLY SPONSORED RESEARCH

This invention was made in part with funds from the National Institute of Health Grant HD25961. The U.S. government therefore may have certain rights in the invention.

FIELD OF THE INVENTION

This invention relates generally to prostaglandins. Specifically, this invention relates to prostaglandin $F_{2\alpha}$ receptor binding protein (FPRP), assays for measuring FPRP, and methods of use.

BACKGROUND OF THE INVENTION

Prostaglandins were discovered through their effects on smooth muscle, specifically their ability to promote the contraction of intestinal and uterine muscle and the lowering of blood pressure. Unlike other hormones, prostaglandins are not stored in cells, but instead are synthesized and released immediately.

There are three major classes of primary prostaglandins, the A, E, and F series. The three classes are distinguished on the basis of functional groups around a cyclopentane ring.

Clinically there are two types of drugs that affect prostaglandin metabolism and are therapeutically useful. First, there are the nonsteroidal, antiinflammatory agents such as aspirin (acetylsalicylic acid), indomethacin, and phenylbutazone, which block prostaglandin production by irreversibly inhibiting cyclooxygenase, an enzyme required for prostaglandin synthesis. The second group, the steroidal antiinflammatory drugs like hydrocortisone, prednisone, and betamethasone, appear to act by decreasing phospholipase $A_2$ activity.

Prostaglandins appear to be one of the natural mediators of inflammation. Inflammatory reactions most often involve the joints (rheumatoid arthritis), skin (psoriasis), and eyes, and inflammation of these sites is frequently treated with corticosteroids that inhibit prostaglandin synthesis. Administration of the prostaglandins $PGE_2$ and $PGE_1$ induce the signs of inflammation that include redness and heat (due to arteriolar vasodilation), and swelling and edema resulting from increased capillary permeability. Prostaglandins are involved in a variety of physiological processes, including pain, fever, reproduction, gastric secretion and peptic ulcers, regulation of blood pressure, ductus arteriosus and congenital heart disease, platelet aggregation and thrombosis (Glew (1992) in: Biochemistry (Devlin, T. M., ed.); Wiley-Liss, NY: pp. 423–473).

Prostaglandin $F_{2\alpha}$ ($PGF_{2\alpha}$) plays a key role in the normal physiology of several tissues including ovary, oviduct, uterus, testis, lung, and possibly eye and heart (Moncada et al. (1985) in: The Pharmacological Basis of Therapeutics, 7th Ed. (Goodman et al., eds.), Macmillan, NY, pp. 660673; Coleman et al. (1989) in: Comprehensive Medical Chemistry Vol. 3 (Hansch et al., eds.), Pergamon Press, NY, pp. 643–714). $PGF_{2\alpha}$ is synthesized, to varying degrees, by almost every tissue in the body. Clearance of $PGF_{2\alpha}$ is also very quick, approximating 90% per pass through the liver and lungs (Piper (1973) in: Prostaglandins: Pharmacological and Therapeutic Advances (Cuthbert, M. F., ed.), J B Lippincott, Philadelphia, Pa.: pp. 125–150).

$PGF_{2\alpha}$ is a stimulant of several different types of physiologic functions including granulosa lutein cell death, myometrial smooth muscle contraction, leydig cell testosterone synthesis regulation, regulation of oviductal cilia beating, bronchoconstriction, and bone metabolism. One of the most important roles of $PGF_{2\alpha}$ is in reproductive biology as a luteolytic agent. In the non-pregnant state, at the end of the luteal phase, increased pulsatile serum levels of $PGF_{2\alpha}$ (of uterine origin) cause apoptotic cell death of the granulosa-lutein cells (Niswender & Nett (1988) in: The Physiology of Reproduction (Knobil & Neill, eds.); Raven Press, NY, N.Y.: pp. 489–525; Robert et al. (1992) Endocrine Rev. 13:432–450; McCracken (1984) Res. Reprod. 16:1–2). In contrast to the non-pregnant state, following implantation, the conceptus (embryo and placenta tissues) is able to signal the maternal adjacent ovary and impart a relative refractoriness of the corpus luteum (CL) to $PGF_{2\alpha}$. This latter phenomena is called maternal recognition of pregnancy. The conceptus influences the surrounding uterus and together the conceptus and uterus send an antiluteolytic or luteotropic signal to the CL. The antiluteolytic signal may be an interferon in some species and/or may involve other conceptus proteins. In this situation, despite the pulsatile, elevated levels of $PGF_{2\alpha}$ normally seen at the end of the luteal phase and a constant affinity of the prostaglandin $F_{2\alpha}$ receptor (FP) (Wiltbank et al. (1995) Biol. Reprod. 52:74–78), the CL is relatively insensitive to $PGF_{2\alpha}$ and continues to function and secrete progesterone and estrogen necessary for placental development and viability. However, the same increased serum $PGF_{2\alpha}$ levels present during normal luteolysis, and which are protected against by the antiluteolytic signal of uterine/conceptus origin, could also adversely affect any tissue possessing the prostaglandin $F_{2\alpha}$ receptor (FP). Thus, it is likely that FP exists in several different forms, such as are seen with the prostaglandin E receptor, or relies on associated proteins to regulate its function. Expression of the FP blocking mechanism may, therefore, be required in a number of $PGF_{2\alpha}$-responsive tissues as well as in the CL of the pregnant animal.

Recently, three independent groups have cloned the cDNA for a putative FP molecule. The cloning strategy of all three groups employed PCR-based approaches that relied on similarities among all PG receptors. Expression of the cloned cDNAs verified that they encoded a protein that specifically bound [$^3$H]$PGF_{2\alpha}$ (Sugimoto et al. (1994) J. Biol. Chem. 269:1356–1360; Sakamoto et al. (1994) J. Biol. Chem. 269:3881–3886; Abramovitz et al. (1994) J. Biol. Chem. 269:2632–2636).

SUMMARY OF THE INVENTION

The invention features a substantially purified rat prostaglandin $F_{2\alpha}$ receptor binding protein (FPRP), characterized as having the amino acid sequence of SEQ ID NO:1 (FIG. 1) and binding the prostaglandin $F_{2\alpha}$ receptor (FP).

The invention features a nucleotide sequence which encodes rat FPRP having the nucleotide sequence of SEQ ID NO:2 (FIG. 1).

In one aspect, the invention features an in vitro assay to determine the presence of $PGF_{2\alpha}$ receptors in a biological sample. The FPRP or a FPRP variant is attached to a solid support and contacted with a biological sample. Detected binding to the immobilized compound indicates the presence of $PGF_{2\alpha}$ receptor in the biological sample.

The invention features a pharmaceutical composition comprising a pharmaceutically acceptable carrier and a therapeutically effective amount of FPRP.

The invention features a method of treating a $PGF_{2\alpha}$-mediated disorder in a mammal by administering an effective amount of FPRP. $PGF_{2\alpha}$-mediated disorders include inflammation, osteoporosis, dysmenorrhea (uterine cramping), asthma, and infertility.

Also included in the invention is gene therapy by introducing into cells a nucleotide sequence encoding FPRP.

The invention features novel FPRP variant polypeptides characterized by the ability to inhibit the binding of $PGF_{2\alpha}$ to FP. In specific embodiment, the variant polypeptides have the minimum sequence of SEQ ID NO:10–24. The invention further features a method for treating a $PGF_{2\alpha}$-mediated disorder in a mammal by administering an effective amount of a FPRP variant.

These and other objects, advantages and features of the present invention will become apparent to those skilled in the art upon reading this disclosure.

BRIEF DESCRIPTION OF THE FIGURES

FIGS. 1A and 1B is the amino acid (SEQ ID NO:1) and nucleotide (SEQ ID NO:2) sequence of rat prostaglandin $F_{2\alpha}$ receptor regulatory protein (FPRP) cDNA. The A of the start ATG defines base pair position number 1. The signal sequence corresponds to aa 1–21 (bold underline). The translated sequence which corresponds to that of the amino terminus of bovine FPRP (ascertained by microsequence analysis on purified FPRP), aa 22–42 is overlined. Potential glycosylation sites are in bold print and are denoted with an asterisk. The transmembrane region, aa 832–853 is denoted with an overline and underline. ATTTA destabilization sequences in the 3' UTR are underlined. The potential poly A addition sequence bp 5760–5765 is both underlined and overlined. GenBank accession number U26595.

FIG. 3 is the ORF predicted immunoglobulin loops aligned with the consensus immunoglobulin loop (SEQ ID NO:3–9). Matches to the consensus are shown in bold type.

FIGS. 6A and 6B is the nucleic acid sequence (SEQ ID NO:49) and ORF translation of the rat ovary FP cDNA (SEQ ID NO:50). The A of the ATG start codon is designated bp 1. Beneath the aa sequence of the rat FP cDNA ORF is a comparison with the mouse ovary FP amino acid sequence. Identical amino acids in the rFP and mFP are indicated with a –, nonidentical amino acids are both shown. (Ovary rFP Accession Number U26663.)

FIG. 12A shows a comparison of rat FPRP nucleotide sequence bp 5591–5744 with the corresponding region of the human homology (SEQ ID NO:48) of FPRP.

FIG. 12B shows a comparison of the genomic rat FPRP nucleotide sequence including and surrounding exon 2 with the corresponding region of the human homolog (SEQ ID NO:52) of FPRP.

DETAILED DESCRIPTION

Figure 2:
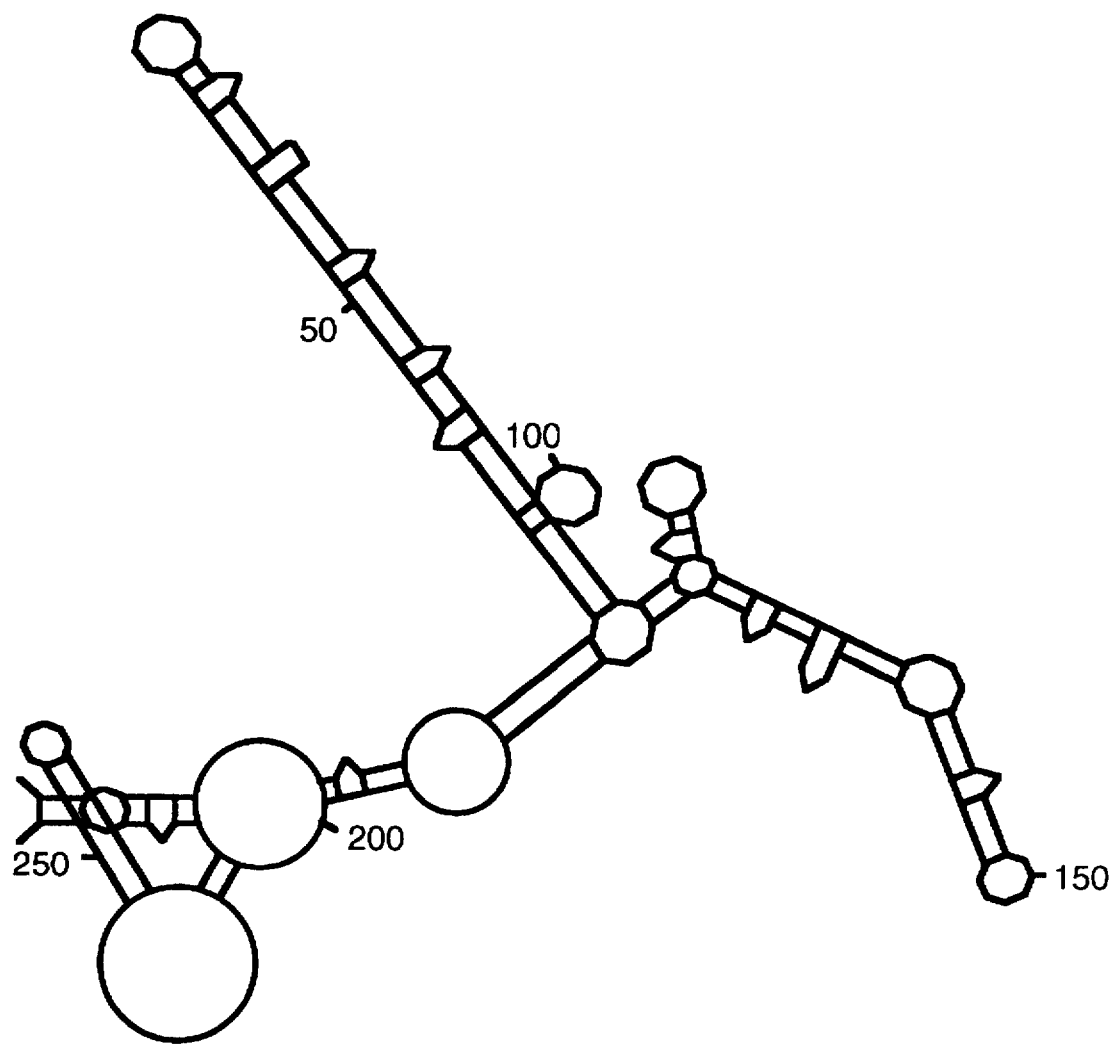
FIG. 2 is a drawing of the Zuker and Stieger algorithm proposed structure for the 5' end of the mRNA of FPRP. The single stranded mRNA molecule is depicted as a single line except in regions predicted to fold and self hybridize (a majority of this molecule). Circles are regions of single stranded mRNA. Parallel lines, such as seen near nucleotide 50, are regions of self hybridization.

Before the present invention is described, it is to be understood that this invention is not limited to the particular sequence or methodology described. It is also to be understood that the terminology used herein is for the purpose of describing particular embodiments only and is not intended to be limiting since the scope of the present invention will be limited only by the appended claims.

It must be noted that as used in this specification and the appended claims, the singular forms "a", "an" and "the" include plural references unless the context clearly dictates otherwise. Thus, for example, reference to "an antibody" includes a plurality of antibodies and mixtures thereof and reference to "the receptor" includes a plurality of receptors of the type generally described herein.

Unless defined otherwise all technical and scientific terms used herein have the same meaning as commonly understood by one of ordinary skill in the art to which this invention belongs. Although any methodology and materials similar or equivalent to those described herein can be used in the practice or testing of the present invention, the preferred methods and materials are now described. All publications mentioned herein are incorporated herein by reference for the purpose of disclosing and describing the particular materials and methodologies for which the reference was cited in connection with.

Cloning and Sequencing of FPRP

The invention features a substantially purified rat prostaglandin $F_{2\alpha}$ receptor regulatory protein (FPRP) characterized as having the amino acid sequence of SEQ ID NO:1 (FIG. 1) and binding the prostaglandin $F_{2\alpha}$ receptor (FP). FPRP has an apparent molecular weight by polyacrylamide gel electrophoresis (PAGE) of about 133 kD and competitively inhibits the binding of the natural FP ligand, $PGF_{2\alpha}$ to FP.

Biochemical purification of the protein complex possessing [$^3$H]$PGF_{2\alpha}$ binding activity has identified protein which co-elutes with the $PGF_{2\alpha}$ receptor, formerly believed to be the $PGF_{2\alpha}$ receptor, but now known to be the prostaglandin $F_{2\alpha}$ receptor associated protein (FPRP) (Orlicky et al. (1990) Prostaglandins, Leukotrienes and Essential Fatty Acids 41:51–61; Orlicky et al. (1992) Prostaglandins, Leukotrienes and Essential Fatty Acids 46:223–229; Orlicky & Williams-Skipp (1992) Prostaglandins, Leukotrienes and Essential Fatty Acids 47:247–252; Orlicky & Williams-Skipp (1993) Prostaglandins, Leukotrienes and Essential Fatty Acids 48:185–192). The co-purification of FPRP with FP first included co-localization to a membrane fraction enriched for [$^3$H]$PGF_{2\alpha}$ binding activity, and then co-enrichment through use of size, DEAE-cellulose, Concanavalin A sepharose and Wheat Germ Agglutinin sepharose chromatography.

Figure 1A:
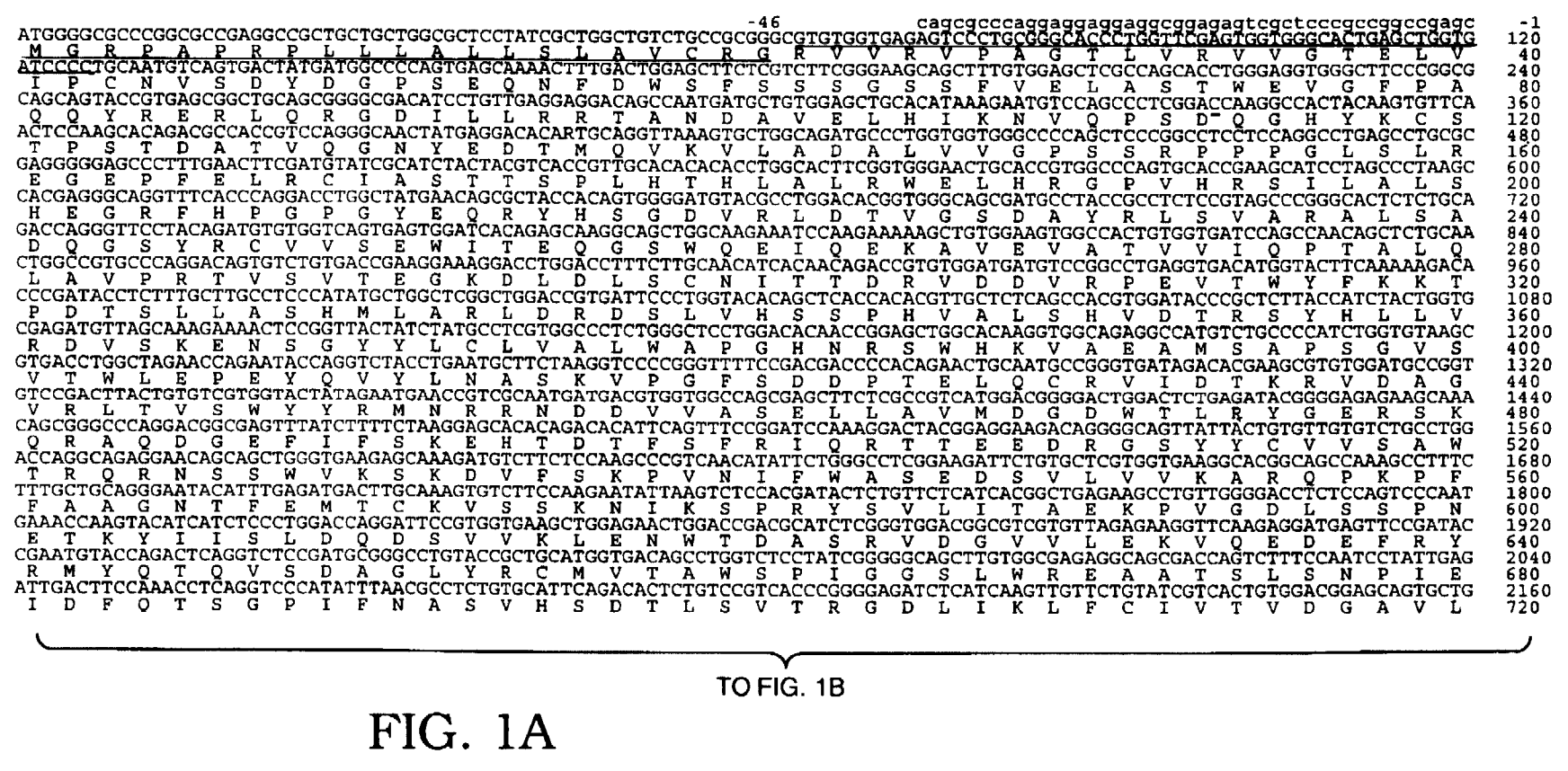
Figure 1B:
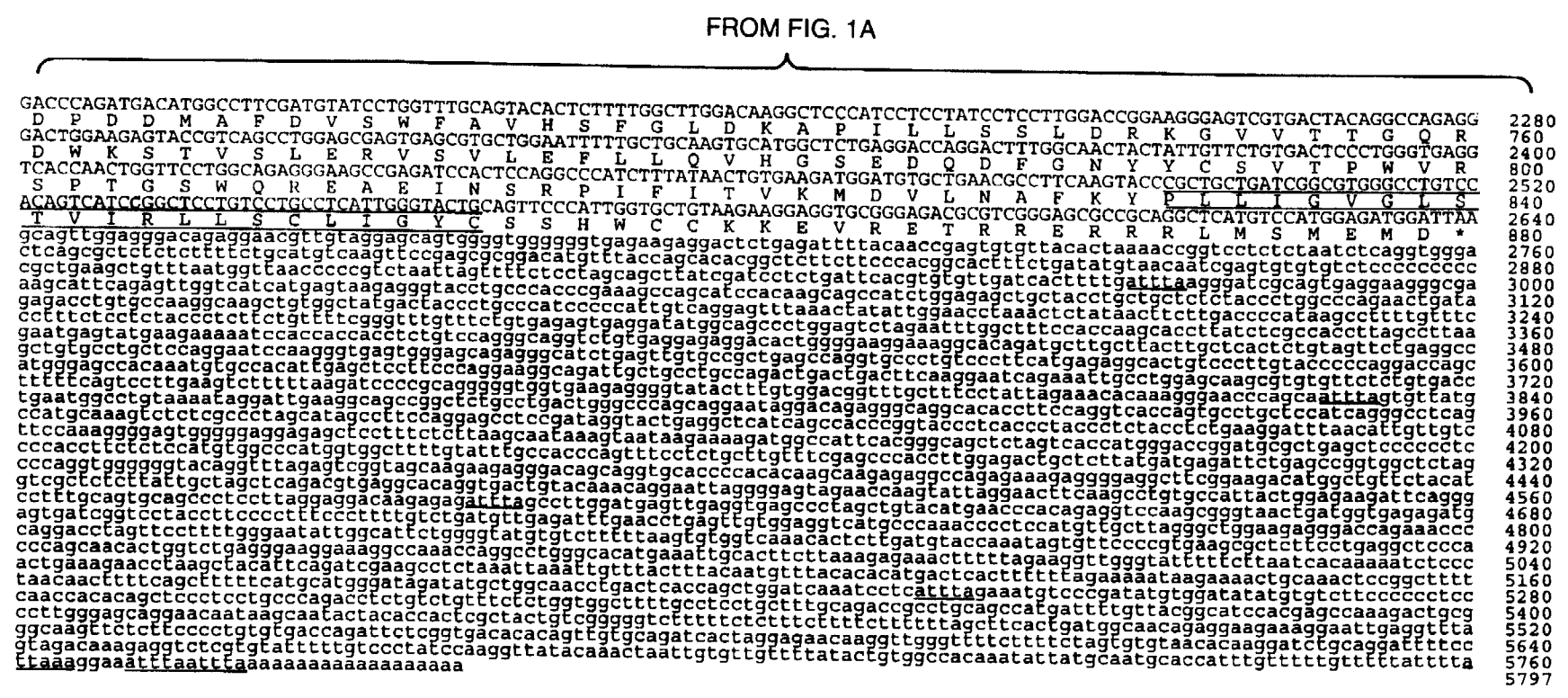

The invention provides nucleotide sequences encoding the FPRP protein (SEQ ID NO:2) (FIG. 1). These nucleotides include DNA, CDNA, and RNA sequences which encode FPRP. It is also understood that all nucleotide sequences encoding all or a portion of FPRP are also included herein, as long as they encode a polypeptide with FPRP activity. Such nucleotide sequences include naturally occuring, synthetic, and intentionally manipulated nucleotide sequences. For example, FPRP sequences may be subjected to site-directed mutagenesis. The nucleotide sequence for FPRP also includes antisense sequences. The nucleotide sequences of the invention include sequences that are degenerate as a result of the genetic code. All degenerate nucleotide sequences are included in the invention as long as the amino acid sequence of FPRP encoded by the nucleotide sequence is functionally unchanged.

Specifically disclosed herein is a cDNA sequence encoding the rat FPRP protein. The sequence contains an open reading frame encoding a protein 879 amino acids in length. Preferably, the FPRP nucleic acid sequence is SEQ ID NO:2.

Included in the invention are fragments of the above-identified nucleic acid sequence that are at least 15 bases in length, which is sufficient to permit the fragment to selectively hybridized to DNA or RNA that encodes the protein of SEQ ID NO:1 under physiological conditions. Specifically, the fragments should hybridize to DNA or RNA encoding FPRP under stringent conditions.

Minor modifications of the FPRP primary amino acid sequence may result in proteins which have substantially equivalent activity to the described activities of FPRP. Such proteins include those as defined by the term "having essentially the amino acid sequence of SEQ ID NO:1". Such modifications may be deliberate, as by site-directed mutagenesis, or may be spontaneous. All of the polypeptides produced by these modifications are included herein as long as the biological activity of FPRP still exists. Further, deletions of one or more amino acids can also result in modification of the structure of the resultant molecule without significantly altering its biological activity. This can lead to the development of a smaller active molecule which would have broader utility. For example, one can remove amino or carboxy terminal amino acids which are not required for FPRP biological activity.

The FPRP protein of the invention encoded by the polynucleotide of the invention includes the disclosed amino acid sequence (SEQ ID NO:1) and conservative variations thereof. The term "conservative variation" as used herein denotes the replacement of an amino acid residue by another, biologically similar residue. Examples of conservative variations include the substitution of one hydrophobic residue such as isoleucine, valine, leucine, or methionine for another, or the substitution of one polar residue for another, such as the substitution of arginine for lysine, glutamic acid for aspartic acid, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

The present invention provides FPRP variant polypeptides characterized by the ability to inhibit the binding of $PGF_{2\alpha}$ to FP. The invention further provides nucleotide sequences encoding FPRP variant polypeptides. In specific embodiments, polynucleotides encoding variant FPRPs are provided having the polynucleotide sequences SEQ ID NO:10–24. The FPRP variants are generated by eliminating portions of the wild-type nucleotide sequence encoding the Ig loop region, the transmembrane domain, and/or the cytoplasmic domain. Modifications of the FPRP variant amino acid sequences are encompassed by the invention so long as the resulting polypeptide exhibits a portion of the biological activity of the wild-type FPRP protein, e.g., inhibition of $PGF_{2\alpha}$ binding to FP. Further included in the invention are FPRP variants wherein one or more amino acids are replaced or changed using techniques of genetic engineering.

A previously described polyclonal antibody, which reacts with both bovine FPRP and rat FPRP (Orlicky et al. (1990) supra) was used to screen a rat ovary cDNA expression library (Example 1). Of the $4\times10^5$ plaques assayed only one clone was strongly recognized by the antibody. The insert was isolated and used as a probe for Northern blot analysis of RNA isolated from tissues previously determined to be positive or negative for [$^3$H]$PGF_{2\alpha}$ binding, e.g., possessing FP (Orlicky (1990) supra). Included in the Northern analysis was RNA from both normal cycling rats and from mid-pregnant (day 13) rats since previous work had suggested that the relative quantities of [$^3$H]PGF$_{2\alpha}$ binding to certain tissues is hormone dependent. The isolated insert was used to find and construct the remaining FPRP cDNA sequence (Example 1).

The cloned cDNA was established to encode FPRP by three criteria. First, FPRP mRNA is found to be present only in those tissues which show immunohistochemical staining with the polyclonal antibody to FPRP. Second, the isolated cDNA codes for the same mature amino terminal protein sequence as that of purified FPRP. Third, COS cells transfected with FPRP cDNA express a 133 kD protein which reacts with an anti-FPRP antibody following Western blotting.

The sequence of the cloned cDNA predicts features of interest in the regulation of expression of the encoded gene. The 5' end of the mRNA is a GC rich region predicted to possess significant secondary structure. There is also a high number of CpG dinucleotides in this region suggesting the presence of a CpG-rich island as seen with many vertebrate genes. The sequence of the long (3141 bp) 3' UTR reveals both destabilization sequences and an inflammatory mediator signature sequence. The presence of destabilizing sequences suggest that the mRNA is a highly regulated molecule with a short half-life. Despite the association of prostaglandins with inflammation, the cloning of cDNAs for genes involved in PG synthesis, binding and degradation has revealed inflammatory mediator sequences only in the cyclooxygenase type II gene (Sugimoto et al. (1994) supra; Sakamoto et al. (1994) supra; Abramovitz et al. (1994) supra; Smith et al. (1991) Pharmacol. Ther. 49:153–179; Funk (1993) Prog. Nucleic Acid Res. Molec. Biol. 45:67–98; Boie et al. (1994) J. Biol. Chem. 269:12173–12178). Sequence analysis of the FPRP cDNA shows the presence of this inflammatory mediator motif, and thus, biological activity as a regulator of prostaglandin action in inflammation.

The cDNA encodes a protein of 879 aa with no extensive homology to other known proteins. The predicted protein structure of FPRP includes a signal sequence, six glycosylated immunoglobulin loops, a transmembrane domain, a short, highly charged, intracellular carboxy tail and possible phosphorylation sites on the intracellular tail. This general type of structure has been seen previously in peptide hormone receptors, cell adhesion molecules, and myelin associated glycoprotein (Williams (1987) Immunol. Today 8:298–303).

Biological Activity of FPRP

The activity of FPRP of pregnant corpus luteum origin was investigated (Example 2). In order to obtain sufficient expression of the FPRP protein to allow Western blot and functional analysis, certain modifications of the FPRP cDNA were required. These included: 1) removal of a majority of the 3' untranslated region including all of the destabilization signals, 2) removal of a majority of the 5' untranslated region due to mRNA structural considerations, and 3) replication of the FPRP cDNA construct in the bacteria GM2163. Although certain portions of the 5' end of the FPRP cDNA acted in an unstable manner during the synthesis, subcloning and sequencing of the 5' end, once this portion had been ligated to the rest of the FPRP cDNA and the 5' UTR removed the resulting FPRP cDNA was stable during growth in DH5, XL-1 blue, and GM2163 bacteria.

Expression of the FPRP cDNA in COS cells results in production of a full length ($\approx$130 kD) molecule immunoreactive with an anti-FPRP antibody, and having an endoplasmic reticulum and golgi network distribution similar to that seen in granulosa lutein cells.

To more precisely examine the hypothesis that FPRP inhibits or regulates specific [$^3$H]PGF$_{2\alpha}$ binding requires use of a target cell line exhibiting a high level of specific [$^3$H]PGF$_{2\alpha}$ binding and which can be transfected at high efficiency. COS cells have a small amount of endogenous specific [$^3$H]PGF$_{2\alpha}$ binding, $\approx$0.01–0.02 fmole of [$^3$H]PGF$_{2\alpha}$ per µg of COS cell protein ($\approx$50 µg cell protein/35 mm culture dish). An inability to find such a cell line necessitated the FP/FPRP co-transfection experiments described in Example 3.

Figure 7:
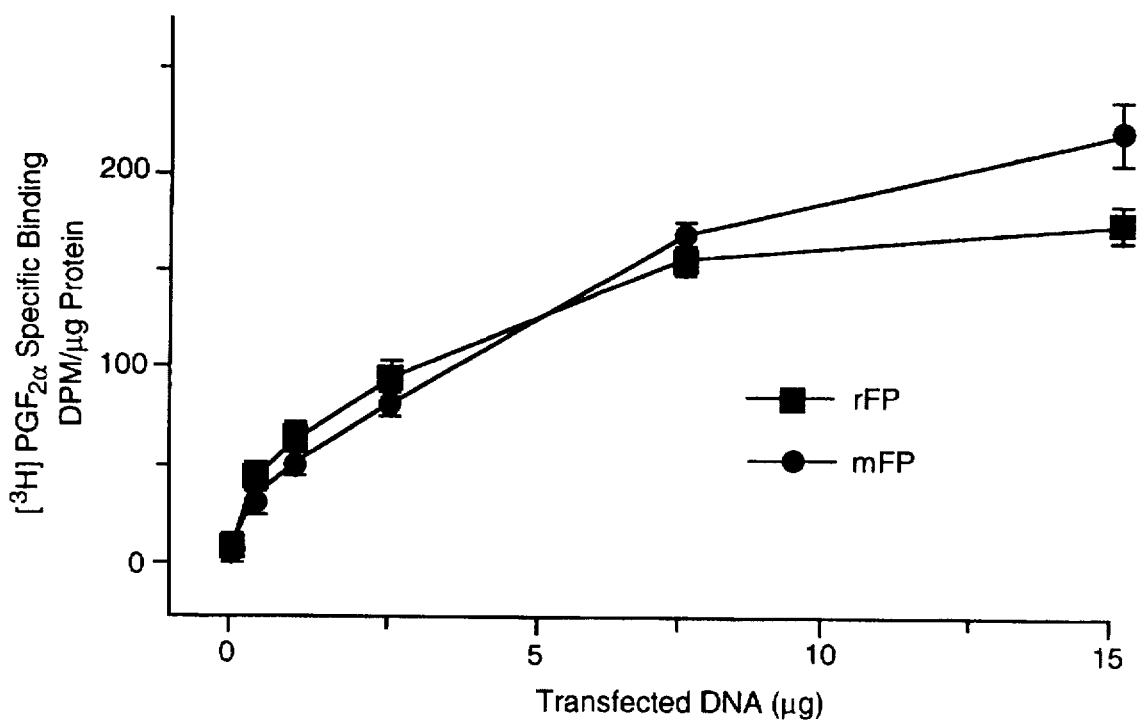
FIG. 7 is a graph of $[^3H]PGF_{2\alpha}$ binding to COS cell cultures following transfection with increasing quantities of rat FP cDNA constructs. Total transfected DNA is indicated on the abscissa. Data points represent mean±standard deviation, n=3.
Figure 8A:
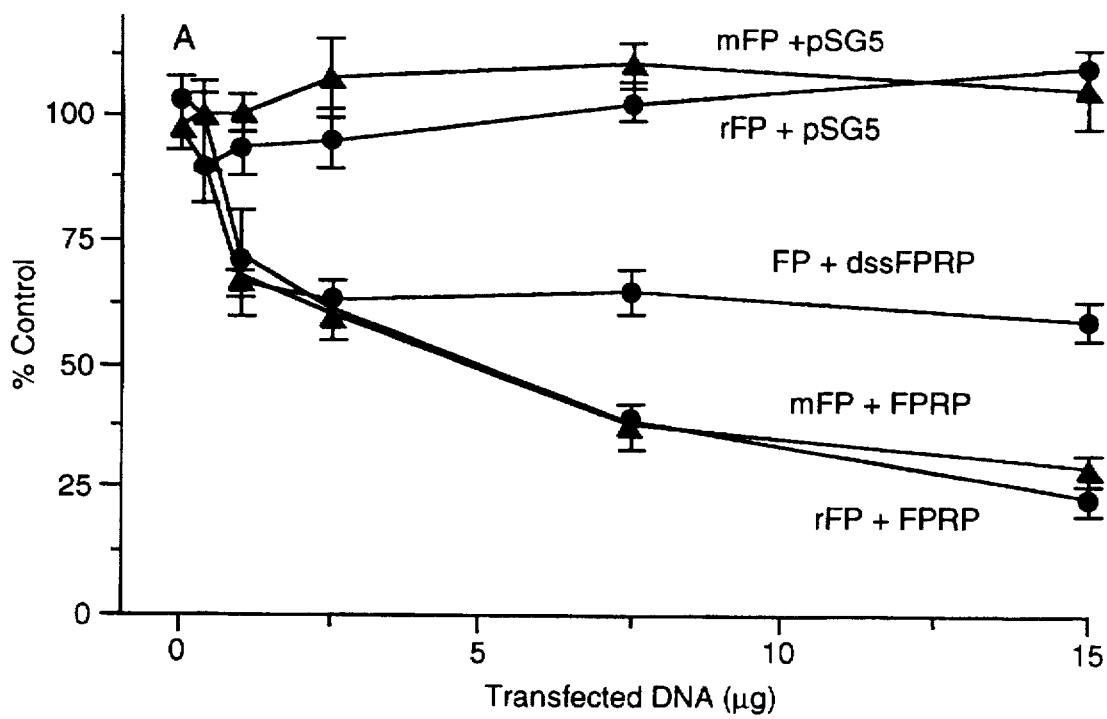
FIG. 8A is a graph of $[^3H]PGF_{2\alpha}$ binding to COS cell cultures following cotransfection with a constant quantity of FP cDNA construct (either rat FP or mouse FP) plus increasing quantities of two FPRP cDNA constructs, FPRP and different signal sequence FPRP (dssFPRP), or vector alone (pSG5).
Figure 8B:
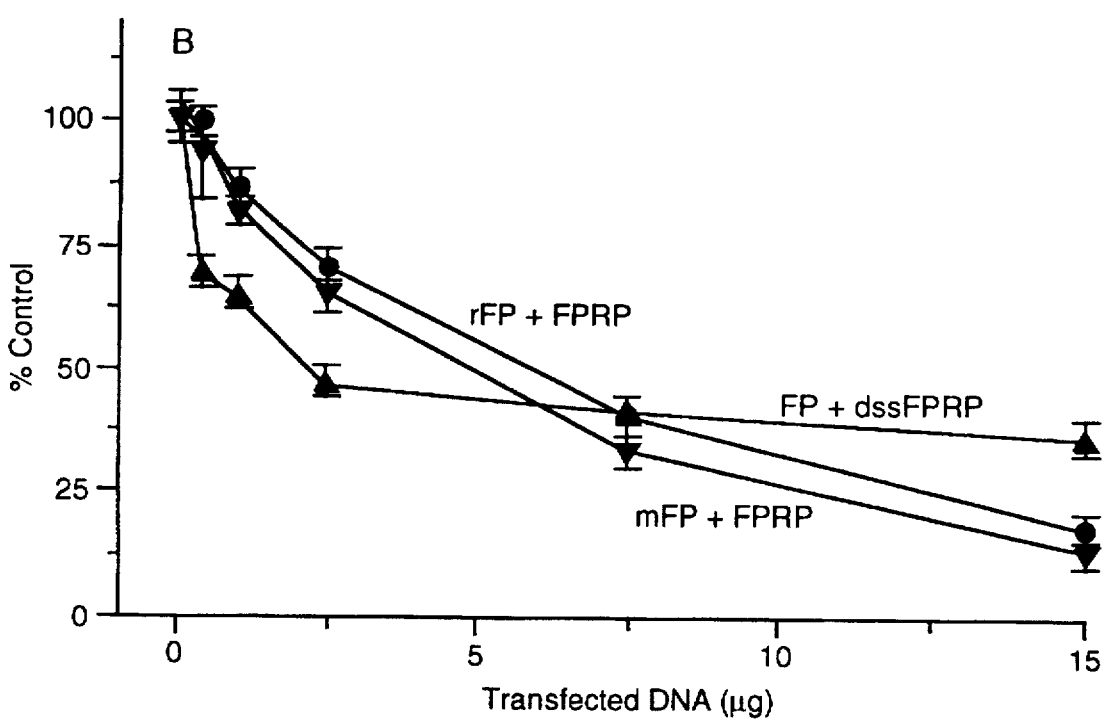
FIG. 8B is a graph of $[^3H]PGF_{2\alpha}$ binding to COS cell cultures following cotransfection with a constant quantity of FP cDNA construct plus increasing quantities of FPRP cDNA constructs. Carrier DNA (pSG5) was used to maintain the total quantity of transfected DNA constant. $[^3H]PGF_{2\alpha}$ specific binding has been expressed as a percent of control (FP cDNA construct only) to allow grouping of multiple experiments. The abscissa, transfected DNA, refers only to the quantity of FPRP cDNA construct transfected. Treatment groups are as described in the legend to FIG. 8A. Data points represent mean±standard deviation, n=3.

FP cDNA for transfection studies was obtained from two sources. First, the rat FP (rFP) cDNA was cloned and sequenced (SEQ ID NO:49). The rat FP cDNA was chosen for cloning due to the rat origin of the FPRP cDNA and the possibility of species specific inhibition. Secondly, mouse FP (mFP) cDNA was obtained from Y. Sugimoto (Kyoto University). The co-transfection experiments were performed as described in Example 3. COS cells transfected with increasing quantities of rFP or mFP alone exhibited dose-dependent [$^3$H]PGF$_{2\alpha}$ binding (FIG. 7). Cells co-transfected with FP (either rFP or mFP) and FPRP exhibited inhibition of [$^3$H]PGF$_{2\alpha}$ binding (FIGS. 8A and 8B).

Figure 10:
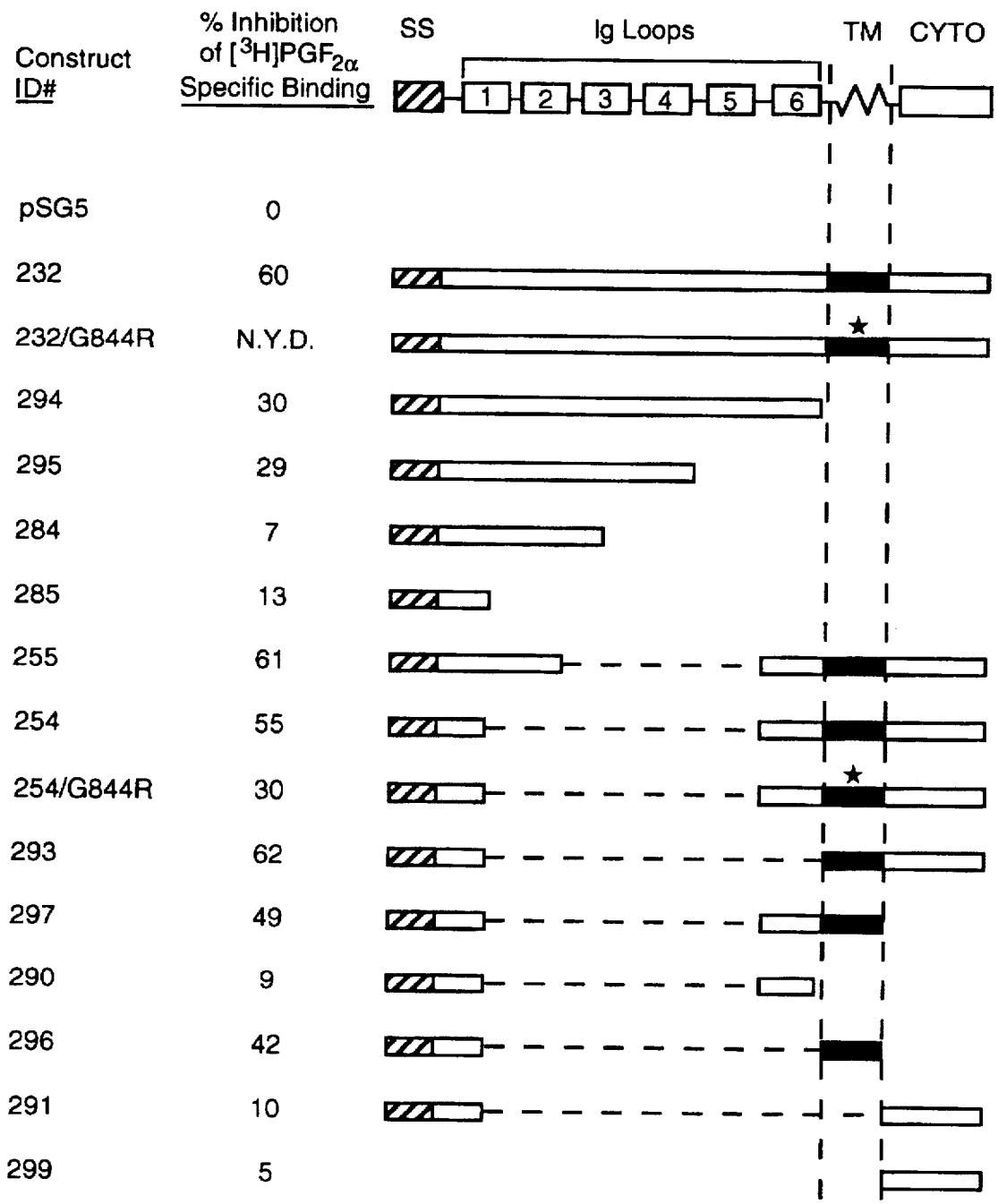
FIG. 10 is a schematic diagram of FPRP variants. The nucleotide sequence of each construct is shown. SS=signal sequence; Ig Loops=immunoglobulin loops 1–6; TM=transmembrane domain; CYTO=cytoplasmic domain. The percent inhibition of $[^3H]PGF_{2\alpha}$ specific binding is compared to FP+pSG5 $[^3H]PGF_{2\alpha}$ specific binding. In all cases, 3.5 µg of FP cDNA construct and 5 µg of test cDNA construst were used.

Modifications of the FPRP protein were constructed and used in co-transfection studies (Example 4; FIG. 10). These modifications include truncations and internal deletions. Internal deletions have been made to allow the sequence downstream of the deletion to remain in-frame with the amino terminus of the protein. All modified constructs (except the construct designated "different signal sequence FPRP") (dssFPRP) (SEQ ID NO:51) (FIG. 10) have the parent signal sequence to target them to the same intracellular location as the parent molecule. Binding study results obtained from the first set of deletions [294 (SEQ ID NO:12), 295 (SEQ ID NO:13), 284 (SEQ ID NO:14), 285 (SEQ ID NO:15)] suggest that the inhibitory activity of FPRP resides between immunoglobulin loop 3 and the carboxyl terminus of the protein. Expressed immunoglobulin loops 1 or 1 and 2 have no inhibitory activity. The second set of constructs [255 (SEQ ID NO:16), 254 (SEQ ID NO:17), 293 (SEQ ID NO:19)] suggest that the transmembrane and cytoplasmic domains can express full inhibitory activity (loop 1 or 1 and 2 with signal sequence were included here to allow correct insertion into and orientation in the membrane). While this result may seem to be at odds with the result from constructs 294 and 295 where some inhibitory activity is seen even after removal of the transmembrane and cytoplasmic portions of FPRP, it may also suggest a recognition role for immunoglobulin loops 4, 5, and 6. Lastly, constructs 293 (SEQ ID NO:19), 290 (SEQ ID NO:21), 296 (SEQ ID NO:22), and 291 (SEQ ID NO:23) attempt to localize the inhibitory activity to either the transmembrane or cytoplasmic domain. Although some inhibition is exerted by the transmembrane domain alone (296), more activity is seen when both the transmembrane and cytoplasmic domains are present (293). Construct 291 may lack activity because, without a transmembrane domain to help orient and localize the cytoplasmic tail, it may be excreted when linked to the parental signal sequence. Data from the dissection constructs presented here represents an important level of specificity by showing that the FPRP protein can be altered to lose its inhibitory activity.

A polymorphism (allele) found to be present in both genomic DNA and a cDNA library clone was isolated which possessed the charged amino acid Arg$_{844}$ in place of the neutral Gly$_{844}$ within the hydrophobic TM region of FPRP. This change was observed to result in loss of half of the activity of FPRP (for example, compare construct 254 (SEQ ID NO:17) with 254/G844R (SEQ ID NO:18).

Figure 6A:
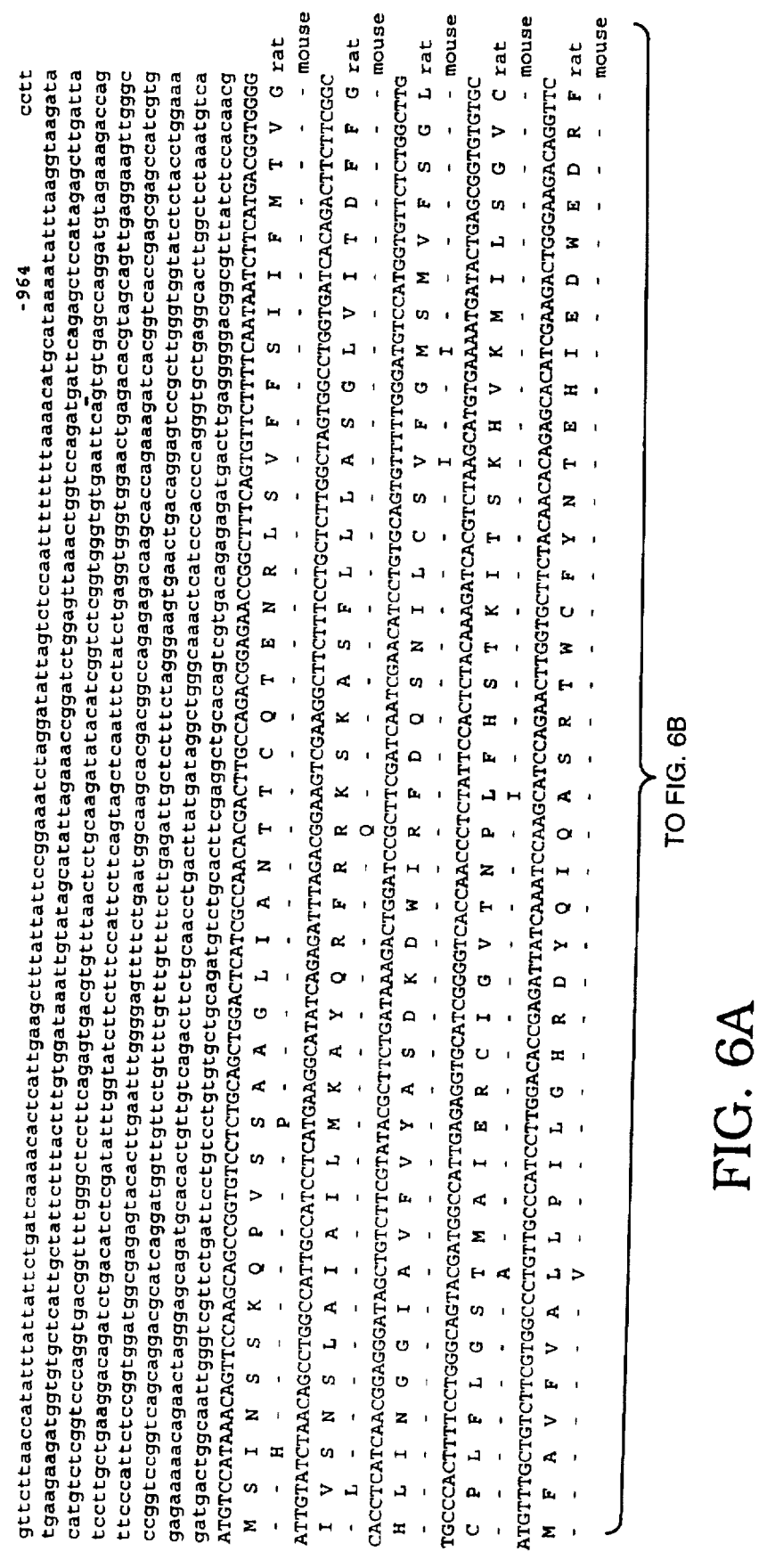
Figure 6B:
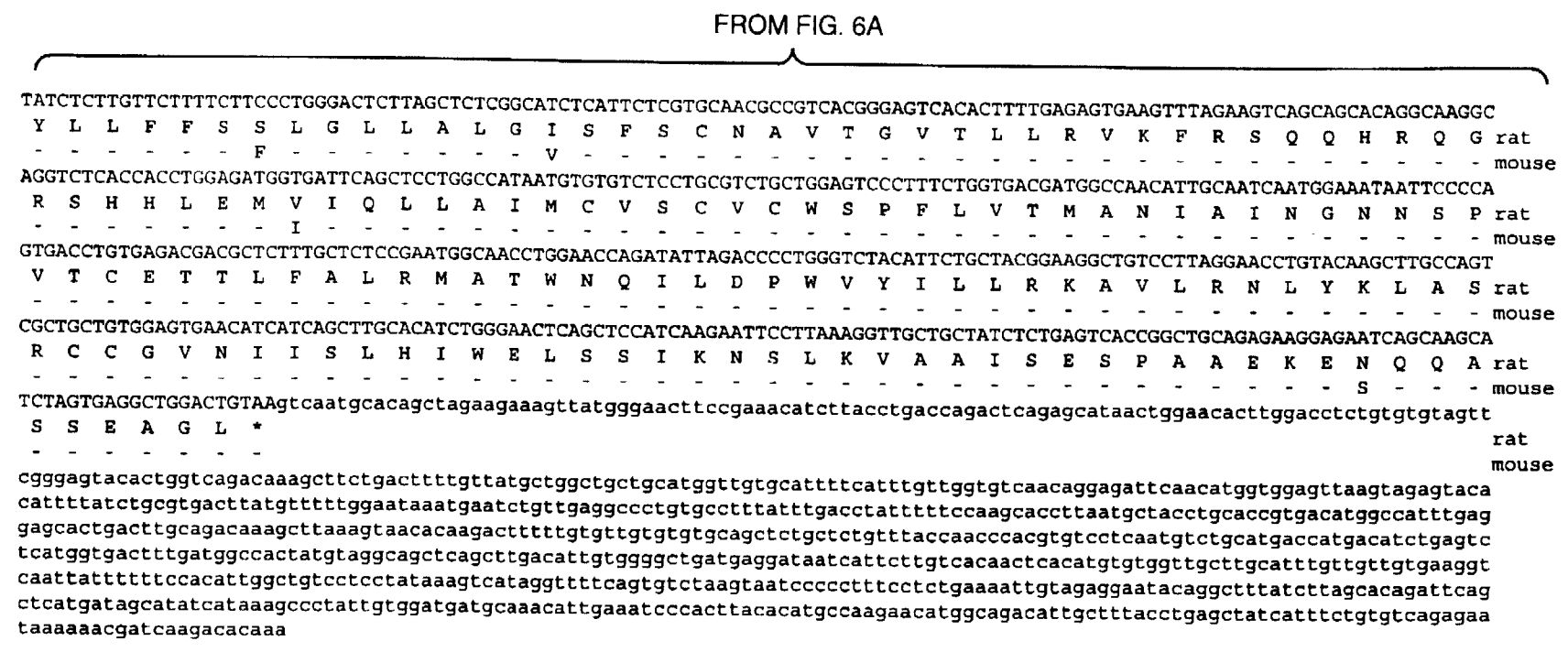

The signal sequence of the trans-golgi network molecule TGN38 (Luzio et al. (1990) Biochem. J. 270:97–102) was substituted for the signal sequence of FPRP therefore targeting FPRP to the trans-golgi network. The activity of this altered FPRP molecule (dssFPRP) is complex and therefore a dose response curve is shown (FIG. 6). The construct dssFPRP may be slightly more active at lower concentrations but does not inhibit quite as well as native FPRP (construct 232) at high concentrations assuming both cDNA constructs are equally transcribed and translated.

Figure 9A:
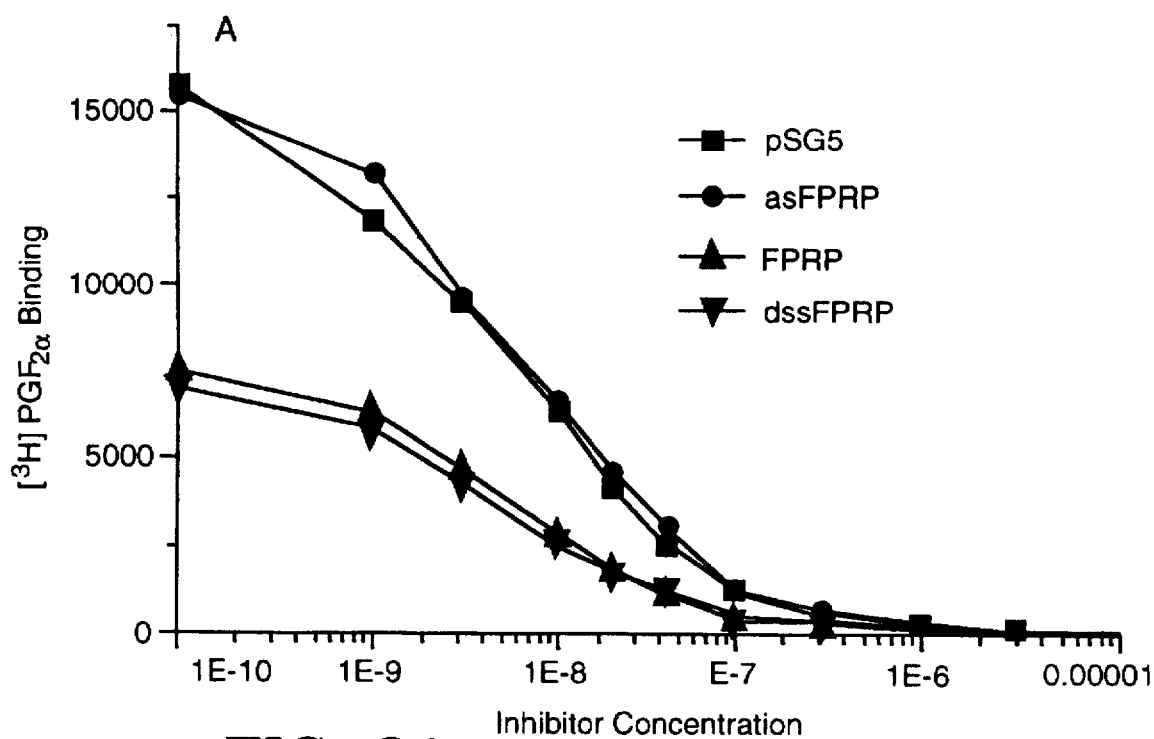
FIG. 9A is a graph of unlabeled $PGF_{2\alpha}$ competition of $[^3H]PGF_{2\alpha}$ binding to COS cell cultures following cotransfection with the cDNA constructs. Treatment groups were transfected with FP and vector only (pSG5, ■), FPRP (▲), antisense FPRP (asFPRP, ●), and dssFPRP (▼). $[^3H]PGF_{2\alpha}$ binding (DPM) was normalized to the average quantity of protein per culture dish (65 µg), and plotted against unlabeled $PGF_{2\alpha}$ concentration.
Figure 9B:
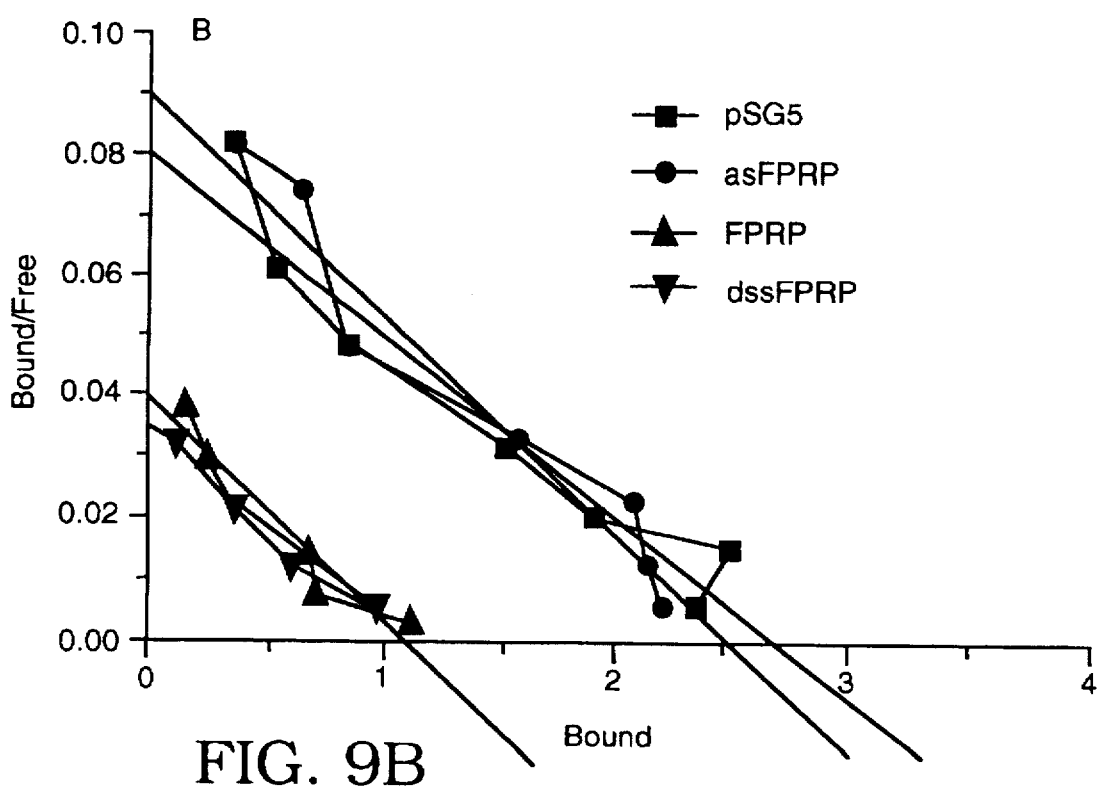
FIG. 9B is a Scatchard plot of the data presented in FIG. 9A of $[^3H]PGF_{2\alpha}$ binding to COS cell cultures following cotransfection with the cDNA constructs for the treatment groups described in the legend to FIG. 8A. Bound $PGF_{2\alpha}$/free $PGF_{2\alpha}$ is plotted against moles of bound $PGF_{2\alpha} \times 10^{-13}$ per normalized culture dish of COS cells.

Saturation binding studies were performed to examine the effect of FPRP on FP (Example 4). The results indicate that FPRP is a non-competitive inhibitor of [$^3$H]PGF$_{2\alpha}$ (FIG. 9A). Scatchard analysis reveals an apparently single, high-affinity binding site on COS cell expressed FP for [$^3$H] PGF$_{2\alpha}$ whether FPRP is present or not (FIG. 9B).

A set of experiments was designed to investigate the nature of the interaction of FPRP with FP (Example 5). Experiments were designed to test four models of interaction—a physical interaction method, an indirect biochemical mediator mechanism, a protease/inhibitor mechanism and an alternate receptor mechanism. Molecular dissection seems to indicate that the transmembrane plus cytoplasmic domains of FPRP possesses the inhibitory activity (Example 4). In support of this conclusion, FPRP was unable to inhibit [$^3$H]PGF$_{2\alpha}$ binding to FP in either conditioned media or co-culture type experiments. Brefeldin A also had no effect on the FPRP inhibitory activity supporting an intracellular mechanism of action for FPRP. Directing FPRP to a trans-golgi network (TGN) location with a TGN specific signal sequence does not alter the activity of FPRP. These findings correlate well with previous immunohistochemical data which suggest an endoplasmic reticulum/trans-golgi network location for FPRP. Furthermore, FPRP only has an inhibitory effect on [$^3$H] PGF$_{2\alpha}$ binding to FP when FPRP and FP are co expressed in the same cell. Again, these observations correlate well with the in vivo situation where the tissue localization of FPRP is highly specific and involves those cells believed to respond to PGF$_{2\alpha}$. Several second messenger perturbing agents were checked for their ability to abrogate the FPRP inhibitory effect but none of these were effective (Table 4).

Localization of the Human FPRP Gene

This negative regulatory activity of FPRP in conjunction with cDNA sequence suggesting a highly regulated molecule (a high degree of secondary structure at the 5' end of the mRNA, the presence of multiple ATTTA "destabilization" sequences in the 3' UTR, and the presence of an inflammatory mediator sequence at the 3' end) prompted a genetic based search for associated pathological conditions.

Figure 11:
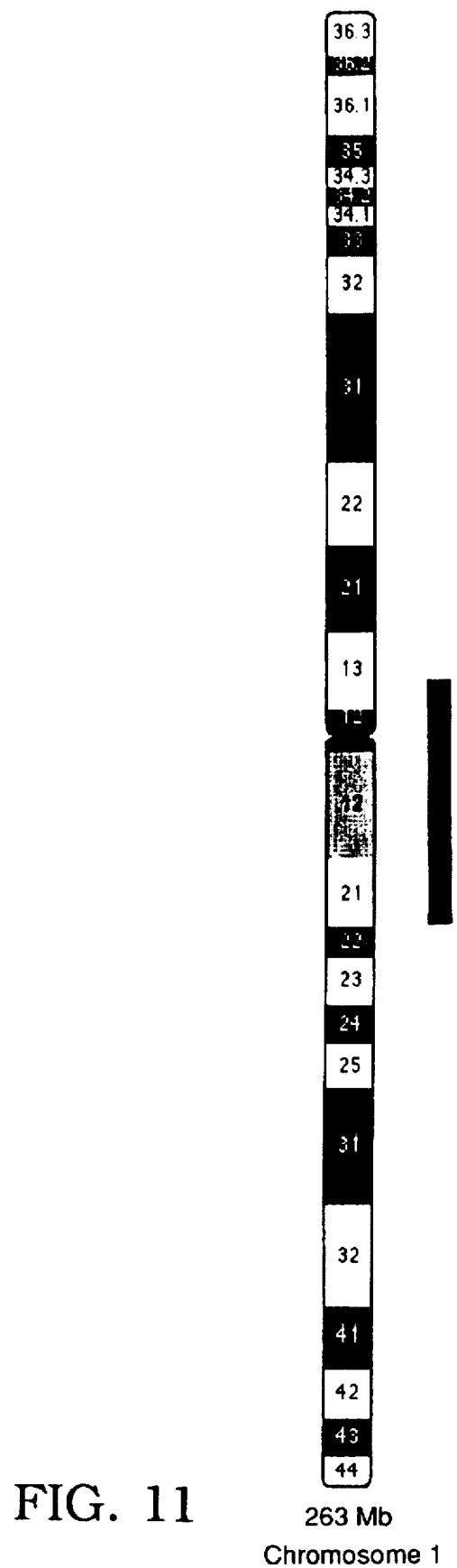
FIG. 11 shows an ideogram of chromosome 1 with the mapping site for the FPRP gene indicated.

A portion of the 3' untranslated region of the human homolog to FPRP was subcloned, sequenced, and oligonucleotide primers chosen which allow PCR amplification specifically of the human FPRP sequence. These primers were then used in a PCR based mapping protocol (Example 6). The human FPRP gene was first localized through human/rodent somatic cell hybrids to human chromosome #1 (100% concordance), and second through YAC pools to region 1p13.1–q21.3 (level 1 mapping) (FIG. 11). This result was verified by subcloning and sequencing from one of the YACs a portion of the human FPRP gene near the open reading frame ATG start (FIG. 12B).

Assay

The compounds of the invention are useful in an in vitro assay to determine the presence of PGF$_{2\alpha}$ receptors in a biological sample. The FPRP or a FPRP variant is attached to a solid support and contacted with a biological sample. Detected binding to the immobilized compound indicates the presence of PGF$_{2\alpha}$ receptor in the biological sample. Attachment of FPRP or a FPRP variant to a solid support may be accomplished in any of a number of ways well known to those skilled in the art.

Therapeutic Use

The FPRP and FPRP variant proteins of the present invention are particularly useful as PGF$_{2\alpha}$ antagonists. Antagonists are compounds which partially or completely block the physiological effect of a ligand by partially or completely preventing binding of the ligand to the receptor. An antagonist competes directly or indirectly with the ligand for the receptor binding site and, thus, reduces the proportion of ligand molecules bound to the receptor. Typically, an antagonist will be the topographical equivalent of the natural ligand and will compete directly with the ligand for the binding site on the receptor. Such a compound is referred to here as a "mimetic". A ligand mimetic is a molecule that conformationally and functionally serves as a substitute for the natural ligand recognized by a receptor, i.e., it attaches to the receptor but does not elicit the biological response of the natural ligand. Alternatively, if the ligand and the test compound can bind the receptor simultaneously, the compound may act non-competitively. A non-competitive inhibitor acts by decreasing or inhibiting the subsequent physiological effects of receptor-ligand interactions rather than by diminishing the proportion of ligand molecules bound to the receptor.

At present, no selective antagonists to FP are known to exist (see, for example, Pharmacol. Revs. (1994) 46:205–227). The present compounds disclosed herein are believed to represent the first discovery of such antagonists. The PGF$_{2\alpha}$ antagonists identified herein are useful in treating a number of PGF$_{2\alpha}$-mediated disease responses. For instance, prostaglandins play an important role in inflammatory reactions relating to rheumatoid arthritis and psoriasis, reproductive disorders, bronchoconstrictive disorders (asthma), excessive bone breakdown (osteoporosis), peptic ulcers, heart disease, platelet aggregation and thrombosis. The PGF$_{2\alpha}$ antagonists of the present invention therefore may be administered locally or systemically to control or alleviate symptoms associated with these disorders, including related tissue damage. Moreover, because of the specificity of the PGF$_{2\alpha}$ antagonists for the PGF$_{2\alpha}$ receptor, these compositions will be more effective and less likely to cause complications when compared to traditional agents.

As a PGF$_{2\alpha}$ antagonist, FPRP and FPRP variants are useful in the treatment of a number of PGF$_{2\alpha}$-mediated disorders, including osteoporosis. PGF$_{2\alpha}$ is known to stimulate osteoclast activity. An overabundance of osteoclastic activity may contribute to osteoporosis. In cases where osteoporosis results from a stimulation of osteoclastic activity, providing FPRP as a PGF$_{2\alpha}$ antagonist may help prevent osteoporosis. A role for prostaglandins in bone remodeling is supported by 1) a decrease in the process by indomethacin and glucocorticoids, 2) the fact that parathyroid hormone appears to work through the local mediator PGE$_2$ in its effects on the osteoblast, and 3) the pronounced effect of estrogen on bone remodeling (Raisz et al. (1990) Endocrinology 126:1076–1079; Huffer (1987) Lab. Invest. 59:418–442; Collins & Chambers (1991) J. Bone Min. Res. 6:157–165).

FPRP and FPRP variants can be used to treat reproductive disorders, such as infertility. In cattle and other ruminants, lack of maternal recognition of pregnancy is believed to play a large role in embryonic mortality. Treatment of a fertilized female with FPRP or FPRP variants may aid in retention of the corpora lutea and hence pregnancy.

$PGF_{2\alpha}$ causes bronchoconstriction and has a pressor-like activity. FPRP has been immunohistochemically localized to the tunica media of the bronchial artery. Lack of sufficient FPRP activity may result in an asthma-like condition. Accordingly, providing FPRP or a FPRP variant may relieve bronchoconstriction.

$PGF_{2\alpha}$ has cardiogenic activity and has been immunohistochemically localized to the myocardium. FPRP insufficiency may lead to heart problems such as high blood pressure or cardiohypertrophy, which may be relieved by providing FPRP or an FPRP derivative.

$PGF_{2\alpha}$ is believed to stimulate androgen secretion in leydig cells. Decreasing androgen secretion may be important at times, for instance, in the treatment of prostate cancer, and could be achieved by providing a $PGF_{2\alpha}$ antagonist.

Pharmaceutical compositions comprising the antagonist of the invention can be used to block or inhibit a number of FP-mediated disorders. For instance, a number of inflammatory disorders are associated with $PGF_{2\alpha}$. The term "inflammation" is used here to refer to reactions of both the specific and non-specific defense systems. A specific defense system reaction is a specific immune system reaction to an antigen. Examples of specific defense system reactions include antibody responses to antigens, such as viruses, and delayed-type hypersensitivity. A non-specific defense system reaction is an inflammatory response mediated by leukocytes generally incapable of immunological memory. Such cells include macrophages, eosinophils and neutrophils. Examples of non-specific reactions include the immediate swelling after a bee sting, and the collection of PMN leukocytes at sites of bacterial infection (e.g., pulmonary infiltrates in bacterial pneumonias and pus formations in abscesses.

Other treatable disorders include, e.g., rheumatoid arthritis, post-ischemic leukocyte-mediated tissue damage (reperfusion injury), frost-bite injury or shock, acute leukocyte-mediated lung injury (e.g., adult respiratory distress syndrome), asthma, traumatic shock, septic shock, and acute and chronic inflammation, including atopic dermatitis, psoriasis, and inflammatory bowel disease. Various platelet-mediated pathologies such as atherosclerosis and clotting can also be treated.

Thus, the present invention also provides compounds useful in producing pharmaceutical compositions which can be used in treating the aforementioned conditions. The pharmaceutical compositions can be prepared according to standard methods (see *Remington's Pharmaceutical Sciences*, Mack Publishing Co., Philadelphia, Pa., 19th ed. (1985) which is incorporated herein by reference). The pharmaceutical compositions are suitable for use in a variety of drug delivery systems. For a brief review of present methods for drug delivery, see, Langer, *Science* 249:1527–1533 (1990), which is incorporated herein by reference.

In one embodiment, FPRP or FPRP variants can be used as to target drugs or other agents to specific FP sites (See, U.S. Pat. No. 5,211,937, herein specifically incorporated by reference). By using a FP-binding moiety to target a drug to a prostaglandin receptor on, e.g., a ovary, uterus, lung or heart cell, such drugs can achieve higher concentrations at sites of interest. Side effects from conventional wide-spectrum agents can be substantially alleviated by the lower dosages, the localization of the agent at the injury sites and/or the encapsulation of the agent prior to delivery.

Targeting can be achieved by directly or indirectly linking FPRP or a FPRP variant to the agent. For instance, liposomes filled with the agent to be delivered to the FP site can be constructed which incorporate FPRP in the lipid membrane (see, Langer, supra). When the liposomes are brought into proximity of the affected cells, they deliver the elected therapeutic compositions.

The pharmaceutical compositions containing FPRP and/or an FPRP variant can be administered for prophylactic and/or therapeutic treatments. In therapeutic applications, compositions are administered to a patient already suffering from a disease, as described above, in an amount sufficient to cure or at least partially arrest the symptoms of the disease and its complications. An amount adequate to accomplish this is defined as a "therapeutically effective dose." Amounts effective for this will, of course, depend on the severity of the disease and the weight and general state of the patient.

In prophylactic applications, compositions containing FPRP and/or a FPRP variant are administered to a patient susceptible to or otherwise at risk of a particular disease. Such an amount is defined to be a "prophylactically effective dose." In this use, the precise amounts again depend on the patient's state of health and weight.

The compounds of the invention is preferably administered with a pharmaceutically acceptable carrier, the nature of the carrier differing with the mode of administration, for example, oral administration, usually using a solid carrier and I.V. administration a liquid salt solution carrier.

The desired formulation can be made using a variety of excipients including, for example, pharmaceutical grades of mannitol, lactose, starch, magnesium stearate, sodium saccharin cellulose, magnesium carbonate, and the like. Oral compositions may be taken in the form of solutions, suspensions, tablets, pills, capsules, sustained release formulations, or powders. Particularly useful is the administration of FPRP directly in transdermal formulations with permeation enhancers such as DMSO. Other topical formulations can be administered to treat dermal inflammation.

A therapeutically effective amount is an amount of FPRP and/or FPRP variant molecule which will bind to a substantial proportional number of prostaglandin receptor molecules so that a $PGF_{2\alpha}$-mediated disorder, e.g., inflammation, can either be prevented or ameliorated. Thus, "treating" as used herein shall mean preventing or ameliorating a $PGF_{2\alpha}$-mediated disorder and/or symptoms associated with the disorder. Typically, the compositions of the instant invention will contain from less than 1% to about 95% of the active ingredient, preferably about 10% to about 50%. Preferably, between 10 mg and 50 mg will be administered to a child and between 50 mg and 1000 mg will be administered to an adult. The frequency of administration will be determined by the care provider based on patient responsiveness. Other effective dosages can be readily determined by one of ordinary skill in the art through routine trials establishing dose response curves.

In determining the dose of FPRP and/or FPRP variant to be administered, it must be kept in mind that one may not wish to completely block all of the prostaglandin receptors. The amount of the FPRP administered as a blocking agent must be adjusted carefully based on the particular needs of the patient while taking into consideration a variety of factors such as the type of disease that is being treated.

Other modes of administration will also find use with the subject invention. For instance, FPRP can be formulated in suppositories and, in some cases, aerosol and intranasal compositions. For suppositories, the vehicle composition will include traditional binders and carriers such as, polyalkylene glycols, or triglycerides. Such suppositories may be formed from mixtures containing the active ingredient in the range of about 0.5% to about 10% (w/w), preferably about 1% to about 2%.

Intranasal formulations will usually include vehicles that neither cause irritation to the nasal mucosa nor significantly disturb ciliary function. Diluents such as water, aqueous saline or other known substances can be employed with the subject invention. The nasal formulations may also contain preservatives such as, but not limited to, chlorobutanol and benzalkonium chloride. A surfactant may be present to enhance absorption of the subject proteins by the nasal mucosa.

FPRP and/or FPRP variants are preferably administered as injectables. Typically, injectable compositions are prepared as liquid solutions or suspensions; solid forms suitable for solution in, or suspension in, liquid vehicles prior to injection may also be prepared. The preparation may also be emulsified or the active ingredient encapsulated in liposome vehicles.

Suitable excipient vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. See, e.g., Remington's Pharmaceutical Sciences, supra. The composition or formulation to be administered will, in any event, contain a quantity of FPRP and/or FPRP variant adequate to achieve the desired state in the subject being treated.

The FPRP and FPRP variants of the present invention can be used alone, or in combination with pharmaceutically acceptable excipient materials as described above. Further, FPRP and FPRP variants can be made as conjugate molecules wherein the FPRP is linked in some manner to a label, e.g., fluorescent, radioactive and enzyme labels. By forming such conjugates, the compound of the invention act as biochemical delivery systems for the label so that a site of inflammation can be detected.

FPRP and FPRP variants can also be used as chimeric molecules conjugated to a chemical moiety such as a peptide, protein, lipid, saccharide, oligosaccharide, polymer, etc. Such conjugate molecules can be used to target the compound to a specific site in the body, to enhance bioavailability or other desirable characteristics.

The FPRP protein and cDNA can also be used as laboratory probes to test for the presence of FP or FPRP expression in a sample. Such probes are preferably labeled.

The present invention also provides gene therapy for the treatment of $PGF_{2\alpha}$-mediated disorders, which are improved or ameliorated by FPRP. Such therapy would achieve its therapeutic effect by introduction of the FPRP or FPRP variant polynucleotide into appropriate cells. Delivery of the FPRP polynucleotide can be achieved using a recombinant expression vector such as a chimeric virus or a colloidal dispersion system. Especially preferred for therapeutic delivery of sequences is the use of targeted liposomes.

Various viral vectors which can be utilized for gene therapy as taught herein include adenovirus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV).

Preferably, when the subject is a human, a vector such as the gibbon ape leukemia virus (GaLV) is utilized. A number of additional retroviral vectors can incorporate multiple genes. All of these vectors can transfer or incorporate a gene for a selectable marker so that transduced cells can be identified and generated. By inserting a FPRP sequence into the viral vector, along with another gene which encodes the ligand for a receptor on a specific target cell, for example, the vector is now target specific. Retroviral vectors can be made target specific by attaching, for example, a sugar, a glycolipid, or a protein. Preferred targeting is accomplished by using an antibody to target the retroviral vector. Those of skill in the art will know of, or can readily ascertain without undue experimentation, specific polynucleotide sequences which can be inserted into the retroviral genome or attached to a viral envelope to allow target specific delivery of the retroviral vector containing the HIF-1 polynucleotide.

Since recombinant retroviruses are defective, they require assistance in order to produce infectious vector particles. This assistance can be provided, for example, by using helper cell lines that contain plasmids encoding all of the structural genes of the retrovirus under the control of regulatory sequences within the LTR. These plasmids are missing a nucleotide sequence which enables the packaging mechanism to recognize an RNA transcript for encapsidation. Helper cell lines which have deletions of the packaging signal include, but are not limited to $\psi 2$, PA317 and PA12, for example. These cell lines produce empty virions, since no genome is packaged. If a retroviral vector is introduced into such cells in which the packaging signal is intact, but the structural genes are replaced by other genes of interest, the vector can be packaged and vector virion produced.

Alternatively, NIH 3T3 or other tissue culture cells can be directly transfected with plasmids encoding the retroviral structural genes gag, pol and env, by conventional calcium phosphate transfection. These cells are then transfected with the vector plasmid containing the genes of interest. The resulting cells release the retroviral vector into the culture medium.

Another targeted delivery system for FPRP and FPRP variant nucleotides is a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. It has been shown that large unilamellar vesicles (LUV), which range in size from 0.2-4.0 um can encapsulate a substantial percentage of an aqueous buffer containing large macromolecules. RNA, DNA and intact virions can be encapsulated within the aqueous interior and be delivered to cells in a biologically active form (Fraley et al. (1981) Trends Biochem. Sci. 6:77). In addition to mammalian cells, liposomes have been used for delivery of polynucleotides in plant, yeast and bacterial cells. In order for a liposome to be an efficient gene transfer vehicle, the following characteristics should be present: (1) encapsulation of the genes of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino et al. (1988) Biotechniques 6:682).

The composition of the liposome is usually a combination of phospholipids, particularly high-phase-transitiontemperature phospholipids, usually in combination with sterols, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidylglycerols, where the lipid moiety contains from 14–18 carbon atoms, particularly from 16–18 carbon atoms, and is saturated. Illustrative phospholipids include egg phosphatidylcholine, dipalmitoylphosphatidylcholine and distearoylphosphatidylcholine.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticuloendothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand.

EXAMPLES

The following examples are put forth so as to provide those of ordinary skill in the art with a complete disclosure description of how to make and use the compound of the invention and are not intended to limit the scope of what is regarded as the invention. Efforts have been made to ensure accuracy with respect to numbers used (e.g., amounts, temperature, etc.) as well as the nomenclature used but some experimental error and deviation should be accounted for. Unless indicated otherwise, parts or parts by weight, molecular weight is weight average molecular weight, temperature is in degree centigrade and pressure is at or near atmospheric.

Example 1

Cloning and Sequencing of Prostaglandin $F_{2\alpha}$ Regulatory Protein

Materials. XL-1 blue bacteria, SURE bacteria, rat ovary CDNA library and rat genomic library all were purchased from Stratagene (La Jolla, Calif.). Oligonucleotide primers (University of Colorado Cancer Center, Denver, Colo. and Macromolecular Resources, Fort Collins, Colo.), [$^{35}$S]dATP and Sequenase 2.0 sequencing kit (United States Biochemical Corp., Cleveland, Ohio), Tth reverse transcriptase (Perkin Elmer, Norwalk, Conn.), and restriction enzymes (Boehringer Mannheim, Indianapolis, Ind. and Gibco BRL, Gaithersburg, Md.) were purchased and used according to accompanying instructions.

Methods. A Sprague-Dawley rat ovary cDNA library was expression screened with a previously produced and characterized polyclonal antibody that recognizes a 135 kD protein representing one of two staining bands in a preparation from pregnant bovine corpus luteum highly enriched for [$^{3}$H]PGF$_{2\alpha}$ binding activity (Orlicky et al. (1990) supra). The antiserum was preabsorbed with phage lysed XL-1 blue bacteria (overnight, 4° C.), precipitated with 50% ammonium sulfate, dialyzed extensively against 40 mM sodium phosphate pH 7.4, and passed through a diethylaminoethyl sephadex column (Sigma, St. Louis, Mo.). Approximately 400,000 plaques were grown on XL-1 blue bacteria at 41° C. for 4 hours in 10 cm petri dishes, then overlaid with nitrocellulose filters, which had been soaked in 50 mM isopropyl-β-D-thiogalactopyranoside (Boehringer Mannheim, Indianapolis, Ind.) and dried, and incubated for 3 hours at 37° C. The filters were then rinsed for 10 minutes in 50% 2-propanol, washed, blocked overnight and immunoblotted as previously described (Orlicky et al. (1990) supra) using swine anti-rabbit sera (DAKO Corporation, Santa Barbara, Calif.) and rabbit peroxidase-antiperoxidase complex (Miles, Elkhart, Ind.). Five potential positives were isolated by purification through four additional rounds of the same procedure. Phagemid from these putatives were in vivo excised according to manufacturers instructions, and the phagemid inserts were excised, purified, and nick translated (Sambrook et al. (1989) Molecular Cloning: A Laboratory Manual, 2nd ed., Cold Spring Harbor Laboratory Press, NY). These labeled probes were used in Northern analysis of several rat tissues known to either contain or not contain [$^{3}$H]PGF$_{2\alpha}$ binding activity (Orlicky (1990) Prostaglandins Leukotienes Essential Fatty Acids 40:181–189).

Following halothane anesthesia, Sprague-Dawley rats were sacrificed by cervical dislocation and RNA was extracted from fresh tissues by an acid guanidinium thiocyanate method (Orlicky (1990) supra). Total RNA (20 μg) from each tissue was electrophoresed through a formaldehyde-agarose gel (Sambrook et al. (1989) supra). Following transfer of the RNA to nitrocellulose, the Northern blots were probed using the nick translated phagemid inserts. Hybridization was performed at 42° C.×24 hours, followed by three washes at room temperature (10 minutes each) and three washes at 55° C. (15 minutes each) all in 2X SSC (0.30M NaCl, 0.03M sodium citrate, pH 7.0) plus 0.1% SDS. Autoradiography was carried out for 100 hours at −70° C.

The four weakly immunopositive clones were judged to be related to each other due to their similar patterns on the Northern blots, and unlikely to be related to the PGF$_{2\alpha}$ receptor based on the tissues in which they were expressed. The single strongly immunopositive cDNA exhibiting appropriate tissue distribution of RNA expression was sequenced. Sequencing was performed on both strands using single stranded DNA (Katayama (1990) Strat. Molec. Biol. 4:56–58) and both the dGTP and the dITP versions of the Sequenase 2.0 sequencing kits. From this initial cDNA (clone 1), which encompasses base pairs (bp) 1761 to 5764 (all numbering corresponds to that of the full sequence seen in FIG. 2) (SEQ ID NO:25), the fragments bp 1761 to 2596 (SEQ ID NO:26) and 5632 to 5764 (SEQ ID NO:27) were isolated and nick translated for use in rescreening the library. Two clones were found by rescreening the Stratagene rat ovary cDNA library (2.3×10$^6$ plaques) with the 3' 5632 to 5764 (SEQ ID NO:27) fragment. These two clones were identical to clone 1 throughout the region of overlap, and both terminated with poly A tails. Rescreening of the Stratagene rat ovary cDNA library (total ≈5×10$^6$ plaques) with the bp 1761–2596 (SEQ ID NO:26) probe resulted in the cloning of three additional unique clones. Sequencing showed these three to be 100% identical with clone 1 over the region bp 1761 to approximately 2100. Of these three new clones, the one which possessed the most 5' sequence started at bp 132. Screening of a Fisher rat lung cDNA library (Fisher, University of Colorado, Colo.) ($\approx 2 \times 10^6$ plaques) was unsuccessful in finding any cDNAs possessing sequence 5' of bp 132.

The cloning of the 5' end of the cDNA was achieved by a compilation of directed strategies. This was necessary due to difficulties that arose due to the unusual sequence composition and structure of this region of the mRNA. All sequencing between bp –46 and 228 required use of both the dGTP and 7-deaza-dGTP sequencing methods (Sequenase 2.0 Sequencing Kit, U.S. Biochemical, Ohio) to give unequivocal sequence. Subcloning at this point required use of the SURE bacterial strain (Stratagene, La Jolla, Calif.) to obviate the rearrangements and deletions seen using DH5α, JM101 and INVαF' bacterial strains.

Total RNA was extracted (Chomczynski & Sacchi (1987) Anal. Biochem. 162:156–159) from the ovaries of rats and used for preparation of poly A containing RNA by a commercial system (Poly A Tract, Promega, Madison, Wis.). First strand synthesis was performed with the heat stable Tth reverse transcriptase using either the primer bp 226 to 210 (SEQ ID NO:28) or the primer bp 200 to 169 (SEQ ID NO:29). Primers are specified with the 5' most nucleotide listed first followed by the 3' most nucleotide. Second strand synthesis was performed by the Gubler and Hoffman method (*E. coli* DNA polymerase I, T4 DNA ligase, and RNase H; Sambrook et al. (1989) supra), the double stranded cDNA was blunt ended with Klenow enzyme, phosphorylated, and ligated to the double stranded adaptor 5'-CTGAATTCTAGATCGATG-3' (P1) (SEQ ID NO:30) and 3'GAGACTTAAGATCTAGCTAC 5' (P2) (SEQ ID NO:31). This product was amplified by polymerase chain reaction (PCR) with the common primer P1 plus a nested primer on the 3' end bp 200 to 169 (SEQ ID NO:29) or bp 160 to 144 (SEQ ID NO:32), respectively. The PCR products were subcloned into either pCRII (InVitrogen, San Diego, Calif.) or pCR-Script SK (+) (Stratagene, La Jolla, Calif.) and sequenced. In a PCR check of this synthesis single stranded cDNA was prepared as above, amplified with the primers bp –30 to –14 (SEQ ID NO:33) and bp 200 to 169 (SEQ ID NO:29), subcloned and sequenced.

The 5' most sequence was generated by first strand cDNA synthesis using primer bp 79 to 63 (SEQ ID NO:34) plus Tth. The second strand synthesis through ligation to the P1/P2 double stranded adaptor were as described above. PCR amplification using primers P1 (SEQ ID NO:30) plus bp 38 to 22 (SEQ ID NO:35), subcloning and sequencing yielded the present 5' end. This end was checked by the above PCR method. First strand synthesis of CDNA from ovary poly A containing RNA by Tth reverse transcriptase and the primer bp 79 to 63 (SEQ ID NO:34) was followed by PCR amplification with primers bp –46 to –28 (SEQ ID NO:36) and bp 38 to 22 (SEQ ID NO:35). The subcloned product was sequenced and showed 100% identity to the previously synthesized cDNA.

A further check on the cloned cDNA sequence was provided by subcloning and sequencing genomic DNA corresponding to both the 5' and 3' ends of the identified cDNA. A Sprague-Dawley rat genomic library (Stratagene, La Jolla, Calif.; $2.5 \times 10^6$ plaques) was screened with nick translated probes corresponding to bp –30 to 38 (SEQ ID NO:37), bp 50 to 226 (SEQ ID NO:38), and bp 5632 to 5764 (SEQ ID NO:27). Positive clones were purified, the appropriate portions were subcloned and sequenced.

The amino acid sequence of the mature amino terminus of the protein was identified by protein sequencing. Briefly, bovine FPRP protein was purified as described (Orlicky et al. (1990) supra), electrophoresed using the pH 7.28 MZE 3328.IV buffer system (Moos et al. (1988) J. Biol. Chem. 263:6005–6008), transferred to PVDF membrane using CHAPS buffer (Matsudaira (1987) J. Biol. Chem. 262:10035–10038) and visualized with Coomassie blue staining. The appropriate portion of the PVDF membrane was excised and used for protein sequencing on an Applied Biosystems 477A protein microsequencer (Colorado Cancer Center Protein Microsequencing Core Laboratory, Denver, Colo.).

Results. An mRNA of approximately 6 kb was found to be present in cycling rat ovary, uterus, lung and possibly heart but not in liver, kidney, spleen, and salivary gland. In midpregnant rat tissues, an equal size mRNA was present in ovary, uterus, lung and heart and absent in liver, kidney, spleen, and pancreas. Faint transcripts of approximately 7.5 kb and 4 kb were also seen in ovary, uterus and lung tissue. Ovary, uterus, lung, and heart have been previously shown to contain [$^3$H]PGF$_{2\alpha}$ binding activity whereas liver, kidney, spleen, salivary gland and pancreas possessed little if any (Orlicky (1990) supra). Similarly, FPRP has been localized by immunohistochemistry to the subpopulations of cells in the ovary, uterus, lung, and heart which are suspected to respond to PGF$_{2\alpha}$ (Orlicky et al. (1992) supra; Orlicky & Williams-Skipp (1992) supra; Orlicky & Williams-Skipp (1993) supra).

Sequencing of the cDNA insert of clone 1 revealed a sequence of 4003 basepairs including an ORF of 879 bp which extended to the 5' end. Use of the nick translated fragments bp 1761 to 2596 (SEQ ID NO:26) and bp 5632 to 5764 (SEQ ID NO:27) in rescreening of the rat ovary cDNA library ($5 \times 10^6$ plaques) yielded five additional independent positive clones. Two of these clones possessed sequences 3' of the known sequence. The fragments from bp 5632 to the 3' end of each of these two was subcloned and sequenced. These two subclones were 100% identical in their portions of overlap with the original clone, and extended the 3' end from bp 5764 to 5781 where the poly A tail began in both of the new clones. These two clones had a poly A tail of 17 and 19 nucleotides. Neither clone extended 5' of the previously known sequence. Two of the other three clones from the library rescreening contained sequence extending 5' of clone 1. The ORF sequence of these three clones was 100% identical to the original clone over the portions sequenced. The clone containing the most 5' sequence starts at bp 132. Sequence analysis revealed an additional 1629 bp of ORF that continued to its 5' border. No convincing start sequence was evident. A sum total of six independent clones were isolated from $5.4 \times 10^6$ plaques (library complexity $\approx 1.7 \times 10^6$) suggesting a low abundance transcript.

Reverse transcriptase synthesis and PCR amplification of the 5' end of the cDNA yielded the final 178 bp of sequence presented in FIG. 1 (GenBank accession number U26595). It is of note that clones containing bp –46 to 210 required growth in the *E. coli* strain SURE to obviate the problems of rearrangement/deletion of the sequence (data not shown). SURE bacteria were specifically engineered to limit rearrangement/deletion events (Greener (1990) Strat. Molec. Biol. 3:5–6).

Subcloning and sequencing of genomic DNA corresponding to the 3' (discussed here) and 5' ends (discussed below)

of the cDNA was performed to confirm the completed cDNA sequence. Seven AUUUA sequences are seen in the 3' UTR of the predicted mRNA. The AUUUA motif is usually seen in inflammation-related and short half-life transcription regulator encoding mRNAs where it is hypothesized to act in cis and confer a short half life upon the mRNA (Shaw & Kamen (1986) Cell 46:659–667). The sequence TTATTT-TAT is observed at bp 5753 to 5761 and is quite similar to a previously described sequence (TTATTTAT) seen near the 3' end of the cDNAs of inflammatory mediators (Caput et al. (1986) Proc. Natl. Acad. Sci. USA 85:2444–2448). The overall size of the 3' UTR is 3141 bp.

At the 5' end of the cDNA, genomic sequence was cloned and sequenced which confirmed bp −36 to 418 with the exception of bp 406 (A in cDNA, G in genomic). The change at bp 406 is a silent third base pair change and may represent a polymorphism. This region of genomic sequence exhibits 3 introns, the first between bp −37 and −36, the second between bp 49 and 50, and the third between bp 418 and 419. No genomic sequence was found for cDNA bp −46 to −37 and yet, following first strand synthesis with reverse transcriptase, successful use of the primer bp −46 to −28 (SEQ ID NO:36) during PCR amplification (annealing temperature 57° C.) is consistent with its presence. Subsequent primer extension experiments show −46 and −44 are the actual sites of transcription initiation. Including this sequence, the observed 5' UTR is 46 bp long. Examination of the sequence from bp −46 to 54 shows the presence of 19 GpC dinucleotides (up from the normal five per hundred) and 13 CpG dinucleotides (up from the normal one per hundred) and is therefore suggestive of a CpG island (Bird (1986) Nature 321:209–213). This same 100 bp region is 77% G plus C. Application of the Zuker and Stieger algorithm (Zuker & Stieger (1981) Nucleic Acis Res. 9:133–148) to the first 256 nucleotides of the predicted mRNA suggests a highly structured 5' end (FIG. 2). Consistent with the presence of structure was extreme difficulty in successfully cloning cDNA for this region. Such a structural element may be implicated in regulating FPRP expression. The inferred initiation codon is found in a CGAGC ATGG sequence which is an acceptable fit to the Kozak initiation sequence (Kozak (1984) Nucleic Acids Res. 12:857–869).

Predicted structure of the FPRP protein. Conceptual translation of the only long ORF in the cDNA (bp 1 to 2640) predicts a protein with 879 amino acids (aa) possessing a 98% chance of coding for a protein (Fickett (1982) Nucleic Acids Res. 10:5303–5318). Protein microsequencing of bovine FPRP suggested a sequence at the mature amino terminus of RVVRVPAGSLVRVVGTELVIP (SEQ ID NO:39). This sequence matches aa 22 to 42 of the proposed rat sequence with one change: a conservative S for T substitution at position 30. Examination of aa 1–21 suggests this is a signal sequence with good conservation of the C, H, and N regions as previously hypothesized (Von Heijne (1985) J. Mol. Biol. 184:99–105). The presence of a signal sequence is consistent with this molecule residing in, and being purified from, a membrane-rich cell subfraction (Orlicky et al. (1990) supra). Six predicted extracellular immunoglobulin loops are present in the aa sequence (Williams (1987) supra). The amino acid sequence of these loops, as well as the consensus aa sequence seen in other immunoglobulin loops is presented in FIG. 3. A 19 amino acid portion of one of these, loop 6, has a hydrophobic moment of 0.5 suggesting it to be either associated with (buried in) a membrane or that it is the site of interaction with another hydrophobic protein. One transmembrane region, aa 812 to 833 (hydrophobic moment 0.64) and a highly charged, short, helical intracellular tail are also predicted (Rao & Argos (1986) Biochim. Biophys. Acta 869:197–214). Eight potential glycosylation sites, N-X-S/T, are present in the extracellular region but none are present in the intracellular region (PROSITE Subprogram of MacD-NAsis version 3.0 (1993), Hitachi Software Engineering America, LTD.). One potential intracellular protein kinase C phosphorylation site, S/T-X-K/R, $T_{845}$-R-R, and one potential calmodulin-dependent protein kinase phosphorylation site, R-X-Y-S, $R_{826}$-L-M-S are present. One endoplasmic reticulum retention signal sequence, P-T-E-L is present at positions 424–427. The mature 858 aa protein (after removal of aa 1–21) is predicted to have a molecular weight of approximately 99 kD. By polyacrylamide gel electrophoresis and Western blot the bovine FPRP was approximately 135 kD. However, following N-glycosidase F treatment, a size of 106–108 kD was observed. For rat FPRP, these values were 133 kD and 104–106 kD respectively (Orlicky et al. (1990) supra). FASTA search of the NIH protein data bank was unable to locate any protein sequence with similarity over more than short stretches (Pearson & Lipman (1988) Proc. Natl. Acad. Sci. USA 85:2444–2448).

Figure 4B:
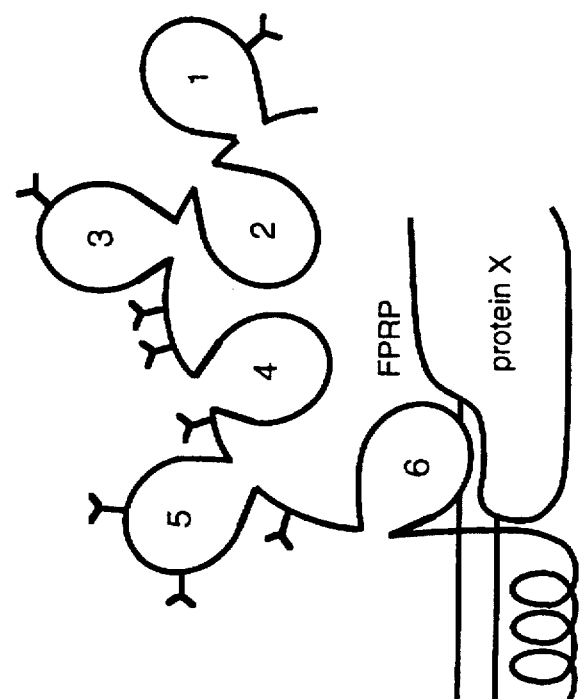
FIG. 4B is a schematic drawing of a second proposed structures for FPRP. Immunoglobulin loops are indicated as loop structures in the extracellular domain, potential glycosylation sites are denoted with the Y shaped symbol. The hydrophobic region of immunoglobulin loop 6 is shown interacting with the hydrophobic region of another protein (protein X) in the plane of the membrane.
Figure 4A:
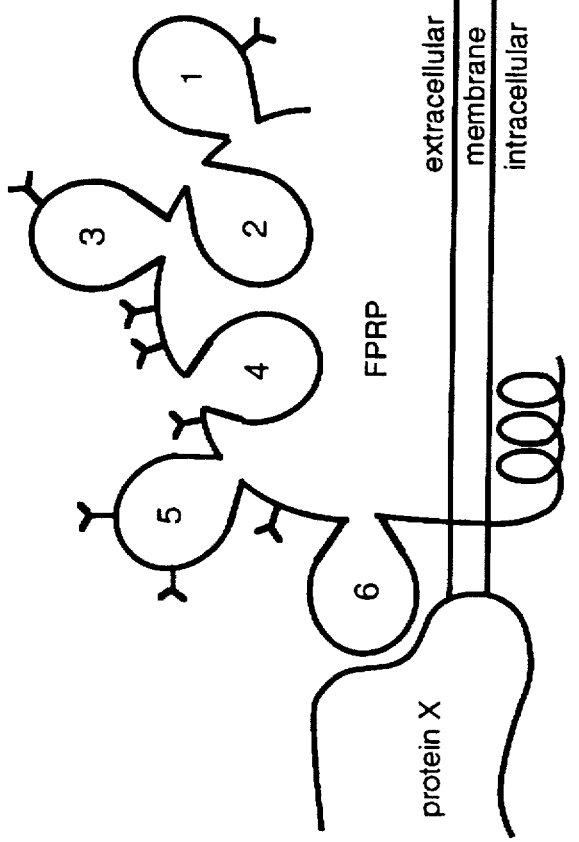
FIG. 4A is a schematic drawing of a first proposed structure for FPRP. Immunoglobulin loops are indicated as loop structures in the extracellular domain, potential glycosylation sites are denoted with the Y shaped symbol. The hydrophobic region of immunoglobulin loop 6 is interacting with the hydrophobic region of another protein (protein X) in the extracellular environment.

FIGS. 4A and 4B presents two hypothetical versions of FPRP. In FIG. 4A, the hydrophobic portion of immunoglobulin loop 6 is interacting with the hydrophobic portion of another protein (protein X) in the extracellular environment; in FIG. 4B this association of loop 6 with protein X occurs in the plane of the membrane.

Example 2

Negative Regulatory Activity of FPRP

Materials. The following materials were used: COS-1 cells (Gluzman (1981) Cell 23:175–182) were obtained from Dr. J. Brown, UCHSC, Denver, Colo.; plasmids pSG5 (Dr. P. Chambon, INSERM, Strasbourg, France; Green et al. (1988) Nucleic Acids Res. 16:369), pCMV6 (Chapman et al. (1991) Nucleic Acids Res. 14:3979–3986), pcDNA3 (Invitrogen, San Diego, Calif.); Ham's F-12 plus 8% fetal bovine serum (Colorado Cancer Center Tissue Culture Care Laboratory), [$^3$H]PGF$_{2\alpha}$ (Amersham Life Science, Arlington Heights, Ill.; 200 Ci (mmol), rat ovary cDNA library (Stratagene, La Jolla, Calif.), oligonucleotide primers (Macromolecular Resources, Fort Collins, Colo.), trypsin (Enzar T 40x trypsin concentrate, Intergen Company, Purchase, N.Y.) and GM 2163 bacteria (New England Biolabs, Beverly, Mass.).

Methods. COS-1 cells were used for transient expression experiments. Briefly, 70–80% confluent cultures (grown in Ham's F-12 media plus 8% fetal bovine serum, with media replacement 24 hours prior to transfection) were harvested with a trypsin/EDTA solution (final concentration: 0.02% ethylenediaminetetracetic acid, 0.05% sodium bicarbonate, and 0.5% Enzart 40x trypsin), washed twice with culture media, then resuspended in ice cold culture media at approximately 1.66×10$^7$ cells per ml. Aliquots of 0.15 ml (2.5×10$^6$ cells) were placed in electroporation cuvettes (BioRad, Hercules, Calif.) along with plasmid DNA, placed on ice for 10 minutes, electroporated with a Bio Rad electroporater (settings: 250 μF, 250 mV, ∞Ω, 0.4 cm cuvette), 1 ml of ice cold culture media was added and the cells were left on ice for 10 minutes before plating.

For [$^3$H]PGF$_{2\alpha}$ binding experiments, the above electroporated cells were divided equally and cultured in six 35×10 mm culture dishes with 1.5 ml culture media each. Binding was performed at 24–26 hours post electroporation (Orlicky et al. (1986) J. Cell Physiol. 127:61–72). Briefly, media was removed from the culture dishes, the dishes were washed 4 times in 1 L each of phosphate buffered saline (PBS, 10 mM phosphate), 150 mM NaCl, pH 7.0), and 0.35 ml of binding buffer (1×Hanks, 0.1% BSA, 2 mM $MnCl_2$, 0.5 mM $CaCl_2$, pH 6.0) containing either $2\times10^{-9}$M [$^3$H]PGF$_{2\alpha}$ (total binding) or $2\times10^{-9}$M [$^3$H]PGF$_{2\alpha}$ plus $2\times10^{-6}$M unlabelled PGF$_{2\alpha}$ (non-specific binding). The binding incubation was at 37° for 20 minutes. Following incubation, the binding buffer was removed, the dishes were washed 4 times in 1 L each of PBS, then 0.5 ml of 1.0M NaOH was added to each dish. Dishes were then incubated overnight at 37° C., the NaOH solution removed, neutralized with 0.5 ml of 1M HCL (made with 200 mM phosphate buffer pH 7.4), vortexed, and aliquots were analyzed for protein by the Bradford technique (1976) Anal. Biochem. 72:248–252, or analyzed for $^3$H content with a Beckman 6000 TA liquid scintillation counter (using Aquasol-2, New England Nuclear, Boston, Mass.; approximate counting efficiency 50–55%). Specific binding is the result of subtracting non-specific binding (dpm per µg protein) from total binding (dpm per µg protein) (three dishes each, total and nonspecific, data expressed as mean±S.D. of dpm per µg protein or as % control if multiple experiments are combined.

For Western blot analysis experiments, the above electroporated cells were divided equally and cultured in three 60 mm culture dishes with 4 ml culture media each. Harvest of the culture occurred at 24–26 hours post electroporation. For harvesting, culture media was removed, centrifuged (1500×g 10 minutes). The cells were removed from the culture dish by rubber policeman in the presence of 1 ml harvest buffer (10 mM Tris, 2 mM ethyleneglycol-bis-N,N, N',N',-tetraacetic acid, 10 mM sucrose, pH 7.0), the removed cells were added to the cells from the media and together they were precipitated overnight at −20° C. with 4 ml acetone:NH$_4$OH 100:1. After the precipitation, material was pelleted by centrifugation (4° C., 8,000×g for 10 min), solubilized in Laemmli sample buffer (Laemmli (1970) Nature 227:248–252), centrifuged (13,000×5 minutes, room temperature) to pellet nucleic acid, and aliquots were electrophoresized through 8% polyacrylamide gels. Following electrophoresis, proteins were Western transferred (125 volt-hour) in Towbin Western blot transfer buffer containing 10% methanol (Towbin et al. (1979) Proc. Natl. Acad. Sci. USA 76:4350–4354), and immunoblotted and developed as previously described (Orlicky et al. (1990) supra).

Results. Expression. Analysis of expression of the cloned FPRP cDNA by Western blot analysis showed that COS cells transfected with no DNA or pSG5 (empty expression vector) lacked immunoreactive material in the 50–200 kD size range. However, transfection with a construct containing the FPRP cDNA, #232 (SEQ ID NO:10), (FPRP cDNA in pSG5) resulted in prominent immunoreactive bands seen near ≈130 kD and ≈105 kD. The 130 kD band is consistent with the size of mature FPRP protein, the 105 kD band may represent either nonglycosylated FPRP or, less likely, initiation at the internal, poor Kozak sequence ACACAATGC to yield a truncated FPRP. Results for expression and activity of the FPRP cDNA in an SV40 promoted expression vector were similar to results observed when the FPRP cDNA is placed in a cytomegalovirus (CMV) promoted expression vector such as pCMV6c.

Analysis of FPRP expression by immunocytochemistry showed that FPRP was visually detected in 20–30% of the FPRP transfected COS cells but not in pSG5 transfected cells. The intracellular localization of the FPRP reactive material was in an endoplasmic reticulum and trans-golgi network type pattern.

Figure 5:
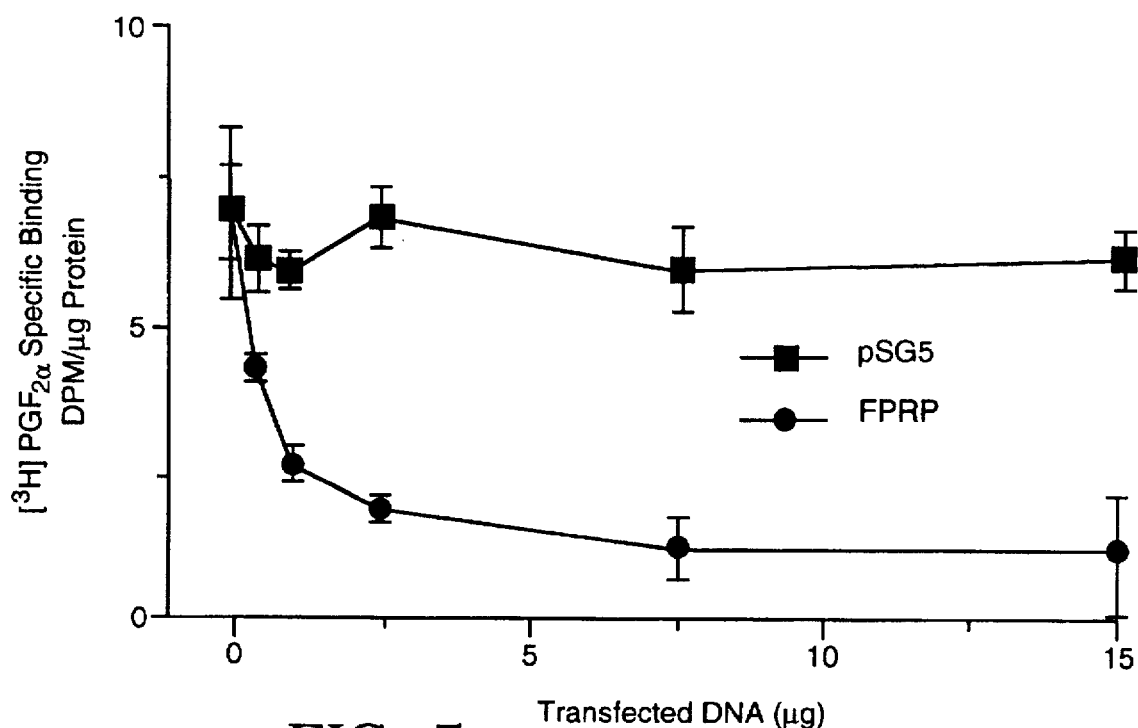
FIG. 5 is a graph of $[^3H]PGF_{2\alpha}$ binding to COS cell cultures following transfection with either pSG5 (expression vector) or with FPRP cDNA construct. COS cells were electroporated, cultured for 24 h and analyzed for specific $[^3H]PGF_{2\alpha}$ binding. Total transfected DNA is indicated on the abscissa. Data points represent mean±standard deviation, n=3.

Function. FPRP expression in COS cells results in a marked, dose dependent decrease in [$^3$H]PGF$_{2\alpha}$ binding, whereas transfection of COS cells with pSG5 DNA has no effect on [$^3$H]PGF$_{2\alpha}$ binding (FIG. 5).

Example 3

Cloning of Rat Prostaglandin F$_{2\alpha}$ Receptor (rFP) and Co-Transfection with Cloned FPRP To clone the rat prostaglandin F$_{2\alpha}$ receptor (rFP), the ORF sequences of the already cloned mouse, bovine, and human FP cDNAs (Sugimoto et al. (1994) supra; Abramovitz et al. (1994) supra; Sakamoto et al. (1994) supra) were first aligned and examined for regions of high sequence homology. Two regions were identified, in transmembrane regions 2 and 7, and oligonucleotides were synthesized corresponding to these. They were mouse bp 223 to bp 239 (5'-ATCACA/TGAC/TTTCTTTGG-3') (SEQ ID NO:40) and bp 890 to bp 874 (5'-TGATTCCAC/TGTTGCAT-3') (SEQ ID NO:41). Polymerase chain reaction (PCR) amplification of a rat ovary cDNA library using these two primers resulted in the expected 667 bp product. This product was subcloned into pCR-Script SK(+) in both orientations, single stranded DNA was prepared (Katayama (1990) supra), and sequenced by both the dGTP and dITP methods using the Sequenase 2.0 kit (United States Biochemical, Cleveland, Ohio) and [$^{35}$S] dATP (Amersham, Arlington Heights, Ill.).

Conceptual translation of the amplified DNA revealed 203 out of the 211 amino acids between these two primers were identical in the mouse and rat FP, establishing that the correct (FP) cDNA had been amplified. The 667 bp PCR product was then purified, nick translated, and used to screen 1×10$^6$ plaques of the rat ovary cDNA library. Eleven positive clones were obtained and the clones which extended farthest 5' and 3' (checked by PCR analysis) were plaque purified and in vivo excised. MRF' E. coli (Stratagene, La Jolla, Calif.) were used for the 5' clone and SURE E.coli (Stratagene, La Jolla, Calif.) were used for the 3' clone due to perceived minor instability problems. Both clones were sequenced using single stranded DNA and sequenase 2.0 as above. These two clones overlapped by ≈950 bp and were identical in sequence in this region of overlap.

The cDNAs of FPRP and both FP's were ligated into expression vectors for the transfection experiments as described below (for nucleotide numbering, see FIG. 1 for FPRP and FIG. 6 for FP). The new junctions of all constructions were sequenced to insure correctness. The FPRP cDNA was ligated into pSG5 following this preparation: FPRP cDNA EagI$_{-8}$ cut, Klenow blunted, HpaI$_{2901}$ cut; pSG5 EcoRI$_{1043}$ cut, Klenow blunted, BglII cut, Klenow blunted. This FPRP/pSG5 construct is referred to as 232 (SEQ ID NO:10). The rFP was ligated into pcDNA3 following this preparation: rFP MunI$_{-110}$ cut, Klenow blunted, Hind II$_{1282}$ cut; pcDNA3 HindIII$_{890}$ cut, Kienow blunted, and EcoRV$_{951}$ cut. The mFP was ligated into pcDNA3 following this preparation: mouse PGFR (MC 205/HindIII #2) cut with HindIII at −12 and 1706; PcDNA3 HindIII$_{890}$ cut. Co-transfection experiments were conducted following the methods described above, in two ways: a constant amount of FP cDNA was used with increasing quantities of FPRP cDNA (increasing total cDNA) or a constant amount of FP cDNA was used with increasing quantities of FPRP cDNA but the total DNA used was kept constant by adding carrier DNA (pSG5).

Controls. A series of control experiments were conducted to verify the results obtained. In the first series, the effect of various vectors and over-expressed proteins was investigated (listed in Table 1). A second series of experiments examined [$^3$H]PGF$_{2\alpha}$ binding under a variety of conditions: the standard binding buffer at pH 6.0, pH 7.0, or the buffer of Weipz et al. (1992) Biol. Reprod. 47:984–991, pH 6.0; cell density prior to electroporations of 60–70%, 80%, or 100% confluency; density of cells post-electroporation at 20–30, 40, or 60–80 μg/dish; and the time between electroporation and binding assay of 24 hr or 48 hr.

Results. FIG. 6 shows the consensus cDNA sequence (SEQ ID NO:49) of the rFP (excluding the 76 bp poly A tail present on this clone), conceptual translation of the open reading frame (ORF) (SEQ ID NO:50), and comparison of the predicted amino acid (aa) sequence with that for the mouse FP (mFP) (rat FP GeneBank Accession Number U26663). The A of the ATG start is designated bp 1. The 5' untranslated region (UTR) of the cloned rFP is much longer than that presented for the mouse, human, or bovine FP sequences. Both the rFP and mFP ORFs predict polypeptides of 366 aa. Furthermore, these two polypeptides differ only at 13 aa (96% identical) and most of these changes are conservative. The 3' UTR of rFP and mFP are similar in size and sequence. The portion of the rFP cDNA which contains the coding region was then placed in the CMV promoted expression vector pcDNA3, and the mFP cDNA coding region was also placed in the CMV promoted expression vector pcDNA3.

FIG. 7 shows that transfection of COS cells with increasing quantities of rFP or mFP increased subsequent specific [$^3$H]PGF$_{2\alpha}$ binding in a simple dose dependent manner. Transfection of 2.5–3.5 μg of either rFP or mFP into ≈2.5× 10$^6$ COS cells yielded binding of ≈100 DPM/μg protein (100 DPM≈0.2 fmole of [$^3$H]PGF$_{2\alpha}$, which was suitable for subsequent cotransfection studies.

Co-transfection with FP and FPRP. FIG. 8A shows the effect of FPRP cDNA expression on the high levels of [$^3$H]PGF$_{2\alpha}$ binding which result from transfection of either the rFP or mFP cDNA constructs. FP cDNA was held constant while FPRP cDNA increased. FIG. 8B shows the results when a constant amount of FP cDNA was used with increasing quantities of FPRP cDNA, but the total DNA used was kept constant by adding carrier DNA (pSG5). Carrier DNA was used due to possible negative nonspecific effects of increasing DNA concentrations during transfection. These negative nonspecific effects could manifest themselves as a decrease in cellular functions. In this case, however, the results of the experiments were the same in either case. Expression of FPRP cDNA decreases subsequent [$^3$H]PGF$_{2\alpha}$ binding. Furthermore, FPRP inhibited rFP and mFP equally showing there was no species specificity.

Functionally and structurally, rat FP and mouse FP are very similar, e.g., sequence homology, [$^3$H]PGF$_{2\alpha}$ binding, and inhibition of [$^3$H]PGF$_{2\alpha}$ binding by FPRP. Also, it is of interest to note that FPRP expression can inhibit FP from all sources tested, including from COS cells, rats and mice.

Controls. Table 1 shows the effect of various vectors and other over-expressed proteins on subsequent [$^3$H]PGF$_{2\alpha}$ binding. While many of these cotransfected, non-FPRP construct DNAs have a minor effect on subsequent [$^3$H] PGF$_{2\alpha}$ binding, none of them inhibit [$^3$H]PGF$_{2\alpha}$ binding to the degree that the FPRP construct does. These results show that the effect of FPRP expression on [$^3$H]PGF$_{2\alpha}$ binding is not simply the result of the presence of a heterologous cDNA nor of heterologous protein expression. Furthermore, expression of the FPRP cDNA in the antisense orientation also lacked negative effects on [$^3$H]PGF$_{2\alpha}$ binding suggesting the effect is not due to the cDNA of FPRP itself, but rather is due to the expressed FPRP gene product.

Further control studies examined the effect of experimental parameters on FPRP inhibitory activity. The results, shown in Table 2, support the finding that the FPRP inhibition of [$^3$H]PGF$_{2\alpha}$ binding by FP is not due to a readily discernable technique artifact. In the course of these experiments it was observed that the expression of FPRP often decreased the viability of the transfected cells by approximately 20–60% relative to pSG5 vector only. Other constructs reduced the viability by 0–60% while having no effect on subsequent [$^3$H]PGF$_{2\alpha}$ binding (Table 1). However, in experiments where the COS cell population used for transfection was nearly 100% confluent and the culture media replaced ≈48 h prior to transfection, then cell viability was unperturbed by transfection with FPRP and yet the inhibitory activity of FPRP remained the same, approximately 60%. Using this 2 day confluent target population for electroporation lowered (by ≈10–30%) the amount of subsequent [$^3$H]PGF$_{2\alpha}$ binding conferred by transfection with FP but it also decreased the [$^3$H]PGF$_{2\alpha}$ binding following cotransfection with FPRP by an equal amount such that the FPRP containing group was still 60% lower. This finding suggests that FPRP does not inhibit binding to FP by a simple toxic mechanism.

Example 4

Construction and Expression of FPRP Variant Polypeptides

FPRP variant molecules were constructed as follows. Number 294 (SEQ ID NO:12) started with 232 (SEQ ID NO:10), was BstXI$_{2363}$ and BstXI$_{2632}$ cut, both ends were T4 DNA polymerase blunted, and religated without the intervening piece. Number 295 (SEQ ID NO:13) started with 232, was BamHI$_{1503}$ and BstXI$_{2632}$ cut, both ends were T4 DNA polymerase blunted, and religated without the intervening piece. Number 284 (SEQ ID NO:14) started with 232, was SstI$_{210}$ and BstXI$_{2632}$ cut, both ends were T4 DNA polymerase blunted, and religated without the intervening piece. Number 285 (SEQ ID NO:15) started with 232, was SstI$_{210}$ and BstXI$_{2632}$ cut, both ends were T4 DNA polymerase blunted, and religated without the intervening piece. In this way, 294 (SEQ ID NO:12), 295 (SEQ ID NO:13), 284 (SEQ ID NO:14), and 285 (SEQ ID NO:15) were truncated and an in-frame stop codon was present at the site of truncation. 255 (SEQ ID NO:16), 254 (SEQ ID NO:17), 293 (SEQ ID NO:19), 290 (SEQ ID NO:21), 296 (SEQ ID NO:22), and 291 (SEQ ID NO:23) all contain internal deletions which were constructed so the resulting protein was in-frame with the coding sequence of the FPRP molecule. 255 (SEQ ID NO:16) started with 232, SmaI$_{707}$ and SmaI$_{2108}$ cut, and religated without the intervening piece. 254 (SEQ ID NO:17) started with 232, was SstI$_{210}$ cut and T4 DNA polymerase blunted, was SmaI$_{2108}$ cut, and religated without the intervening piece. 293 (SEQ ID NO:19) started with 232, was SstI$_{210}$ and Asp 700I$_{2483}$ cut, T4 DNA polymerase blunted, and religated without the intervening piece. 290 (SEQ ID NO:21) started with 254, was BstXI$_{2363}$ and BstXI$_{2632}$ cut, both ends were T4 DNA polymerase blunted, and religated without the intervening piece. 296 (SEQ ID NO:22) started with 293, was PstI$_{2561}$ and BstXI$_{2632}$ cut, both ends were T4 DNA polymerase blunted, and religated without the intervening piece. 291 (SEQ ID NO:23) started with 232, was SstI$_{210}$ and PstI$_{2561}$ cut, both ends were T4 DNA polymerase blunted, and religated without the intervening piece. The variant having a different signal construct (dssFPRP) (SEQ ID NO:51) required two construction steps. First, the FPRP genomic sequence which correlates with part of intron 2 (between bp 49 and 50 of FPRP) to SstI$_{210}$ was cut with PvuII$_{50}$, and the genomic intron was replaced with the oligonucleotide pair 5'-GAATTCAGGATGCAGTTCCTGGTTGCGTTGCTC-CTGCTGAGTGCAG-3' (SEQ ID NO:42) and 3'-CTTAAGTCCTACGTCAAGGACCAACGCAACGAG-GACGACTCACGTC-5' (SEQ ID NO:43). This construct was cut with EcoRI (5' end of the synthesized oligonucleotide pair) and SstI$_{210}$, then the isolated 5' synthetic FPRP fragment was ligated into the FPRP cDNA (prepared by removing the 5' end down to SstI$_{210}$). The resulting FPRP with synthetic 5' signal sequence was cut with EcoRI at the 5' end and HpaI$_{2901}$ and ligated into pSG5 prepared by BglIII$_{1055}$ cut, Klenow blunted and EcoRI$_{1043}$ cut. In this way a signal sequence of (amino acid sequence) MQFLVALLLLSAAVCHG↓ (SEQ ID NO.44) was engineered onto the FPRP molecule in place of its own signal sequence and yet the processing point VCHG↓ was retained. This resulting signal sequence was modeled after the trans-Golgi network protein TGN38 signal sequence (MQFLVALLLLSVAVARA↓) (SEQ ID NO:45). [$^3$H] PGF$_{2\alpha}$ binding was measured in cells co-transfected with FP and a FPRP variant following the procedure described above.

Saturation binding. A saturation binding experiment was performed to examine the effect of FPRP on FP. Scatchard analysis should discriminate between competitive and noncompetitive methods of FPRP action. [$^3$H]PGF$_{2\alpha}$ binding was assessed following transfection with either FP+pSG5 or FP+anti-sense FPRP (2 controls) and following transfection with FP+FPRP or FP+ dss FPRP (2 experimentals). Data are shown in FIG. 9A for unlabelled PGF$_{2\alpha}$ inhibition of [$^3$H] PGF$_{2\alpha}$ binding and in FIG. 9B for the Scatchard transformation of this same data.

Results. FIG. 10 is a diagram of the sequences of the modified FPRP variants and their effect on [$^3$H]PGF$_{2\alpha}$ binding when co-transfected with FP.

Saturation binding. Both controls (pSG5 and asFPRP) had similar effects on [$^3$H]PGF$_{2\alpha}$ binding (FIG. 9A). Both experimental groups (FPRP and dssFPRP) also yielded similar effects on binding.

The [$^3$H]PGF$_{2\alpha}$ binding affinity measured with these 4 treatments all were similar (8×10$^{-9}$) and approximated the binding affinity (25×10$^{-9}$) reported by Ito el al. (1994) supra. Similar binding affinities for the control and experimental groups suggest a noncompetitive type of inhibition.

FPRP inhibited [$^3$H]PGF$_{2\alpha}$ binding to FP by approximately 60% in this experiment consistent with previous experiments.

Example 5

Interaction of FPRP with FP

Models for FPRP interaction with FP were tested as follows. First, a conditioned media experiment was performed with either the pSG5 vector, or the FPRP cDNA construct transfected into COS cells. Following plating and culture of these transfected cells for 24 hours the media in which the cells were grown was placed on cultures of cells transfected with FP. The cells transfected with FP and cultured with the conditioned medium for 4 hours were then analyzed for [$^3$H]PGF$_{2\alpha}$ binding. In a second experiment, FPRP or pSG5 were transfected as described above into one set of cells, FP alone into a second set of cells, and the cells co-cultured in the ratios shown in Table 3.

Briefly, COS cells were transfected with FP, pSG5, or FPRP, and plated. 24 h post transfection, media was removed from the pSG5 and FPRP transfected cultures, centrifuged 7 min at 1000×g, and added back to the FP culture media at the indicated ratios. Following 4 h of this media treatment, [$^3$H]PGF$_{2\alpha}$ binding was analyzed. As a control, FP and FPRP were cotransfected. For co-cultured cells, COS cells were transfected with FP, pSG5, or FPRP, mixed at a 1:1 ratio and cultured. As a control, cells were either transfected with FP or FP+FPRP.

In a third experiment, transfected cells were treated for 30 min with exposure to the following: phorbol 12-myristate 13-acetate 10$^{-8}$M, prostaglandin E$_1$, 10$^{-7}$M, A23187 10$^{-6}$M, okadaic acid 10$^{-6}$M, or 8-Br-cAMP 10$^{-5}$M (Table 4). Pretreating with PGF$_{2\alpha}$ 10$^{-7}$M for 30 min decreased subsequent basal FP binding and also decreased FPRP inhibited FP binding such that the percent inhibition in this and all treatments tested was ≈50%.

The effect of brefeldin A (3 μg/ml, 2 hr), chloroquine (100 μM, 6 hr) and tunicamysin (2.5 μg/ml, 20 hr) was determined. The results, shown in Table 4, show these compounds had little effect on the FPRP inhibition of [$^3$H] PGF$_{2\alpha}$. In fact, there is little or no effect of brefeldin A or chloroquine on either the basal [$^3$H]PGF$_{2\alpha}$ binding or FPRP inhibition of that binding. The lack of a brefeldin A effect on FPRP's inhibitory action may suggest that FPRP acts within the endoplasmic reticulum lumen since befeldin A inhibits trafficking of molecules from the endoplasmic reticulum to the golgi apparatus (McCracken (1984) supra). On the other hand, tunicamycin pretreatment decreased [$^3$H]PGF$_{2\alpha}$ binding suggesting glycosylation of FP is necessary for [$^3$H] PGF$_{2\alpha}$. FPRP inhibited [$^3$H]PGF$_{2\alpha}$ binding to approximately the same extent following this tunicamycin pretreatment.

The third model for FPRP interaction with FP suggests that an enzymatic activity of FPRP is involved. The amino acid sequence of FPRP was first checked for motifs consistent with known enzymatic activities (PROSITE) but none were found. Therefore, a strategy based on cotransfection of a third construct (along with FP and FPRP) was pursued. These third party constructs included ones coding for the protease inhibitors alpha-1 trypsin inhibitor and crmA, an inhibitor of cell death, bcl2, and few nonspecific control molecules including the vitamin D receptor, a secreted immunoglobulin molecule, and the empty parent vector pSG5 only. All groups and treatments were compared with control treatment of FP+pSG5 vs. FP+FPRP. In all cases the quantity of [$^3$H]PGF$_{2\alpha}$ binding to these cultures was the same (35±5% of control) indicating no effect of the third party construct on FPRP inhibition of [$^3$H]PGF$_{2\alpha}$ binding to FP (Table 4).

Due to its structure, the possibility was considered that FPRP is in fact a receptor (for an unknown ligand) and that following stimulation of it, a cascade of events was initiated which resulted in the decreased binding of [$^3$H]PGF$_{2\alpha}$ to FP. Cells transfected with either FP and pSG5 or FP and FPRP were plated in normal media containing serum and at either 21 h, 6 h or 0 h prior to [$^3$H]PGF$_{2\alpha}$ binding analysis had their media replaced with serum deficient medium, in order to obviate any effects due to hormones or factors present in the added serum. Growth in serum deficient media decreased subsequent [$^3$H]PGF$_{2\alpha}$ binding, but did not alter the percent of FPRP inhibition of [$^3$H]PGF$_{2\alpha}$ binding (Table 4). The lack of an effect of serum deprivation suggests that FPRP is not a receptor for some molecule in serum.

Example 6

Localization of the Human FPRP Gene

Chromosome regional mapping of the FPRP gene required three stages. First, a portion of the 3' UTR of the human FPRP, which was identified through homology to the rat FPRP was amplified, subcloned and sequenced. Next, following synthesis of oligonucleotides specific to human FPRP, PCR screening of a human/rodent somatic hybrid panel allowed assignment of the FPRP gene to a chromosome. Finally, a regional map location was identified by PCR screening of yeast artificial chromosome (YAC) DNA pools.

The EMBL data base was screened with the rat FPRP nucleotide sequence and a single human cDNA sequence (260 bp, single read, unpublished, Genexpress, Accession #Z18311) was identified as being homologous (poisson probability $5.6 \times 10^{-39}$) to the rat sequence bp 5593 to bp 5822. Visual alignment of the rat and human sequences allowed selection of oligonucleotide primers, one of which was common to both sequences and one of which maximized the differences between the rat and human sequences. These oligonucleotide primers (5'-ACAAATGGTGCATTGCATA-3' (SEQ ID NO:46) and 5'-ACGTTGACTTTCCTTTTAA-3' (SEQ ID NO:47)) were then synthesized (Macromolecular Resources, Fort Collins, Colo.) and used in a PCR amplification protocol (PCR reactions performed as indicated below) on genomic DNA of several sources. The expected 157 bp fragment was produced from human genomic DNA, and no product was detected between 0–300 bp following PCR amplification of yeast, hamster, or mouse genomic DNA. This 157 bp PCR product of human DNA origin was subcloned using the vector pCRII (Invitrogen, San Diego, Calif.) and sequenced (Sequenase 2.0 kit, United States Biochemical, Cleveland, Ohio) with both the dGTP and dITP methods in both directions. Sequence analysis of this 157 bp PCR product (GenBank accession number U26664) revealed a 23 bp difference between the amplified human sequence and the rat FPRP sequence (85% identity) and a 4 bp difference from the EMBL Accession #Z18311 human sequence. Optimal alignment of the rat and human sequences showed that a large proportion of these mismatches are in the 5' end allowing for a unique oligonucleotide at that end while the 3' ends of the rat and human sequences are identical (FIG. 12).

These same oligonucleotide primers were then used for chromosomal assignment by means of a PCR screening of the National Institute of General Medical Science (NIGMS/NIH) human/rodent somatic hybrid panel no. 1 available from the Coriell Institute for Medical Research (Camden, N.J.). Human/rodent somatic cell hybrids GM/NA09925, GM/NA09926, GM/NA09927, and GM/NA09933, all were positive for the 157 bp product, suggesting the human FPRP gene resides on chromosome 1. All PCR reactions were performed using a Perkin-Elmer Gene Amp PCR System 9600 thermal cycler. In the 15 µl PCR reaction, 50 ng of DNA was used for each somatic hybrid in the panel, as well as for the human, mouse, and hamster genomic DNA controls. The PCR reaction contained 250 µM of each dNTP, 100 ng of each primer and 0.4 units of AmpliTaq polymerase in 1× GeneAmp reaction buffer (50 mM KCl, 10 mM Tris-HCl, pH 8.3, 1.5 mM $MgCl_2$, Perkin Elmer Cetus, Norwalk, Conn.). Reactions were cycled 4 min at 94° C., then 35 cycles of 15 s at 94° C., 1 min 15 s at 55° C., and 1 min 15 s at 72° C. followed by an extension step of 10 min at 72° C. Reactions were kept at 4° C. until analyzed on 2% agarose gels stained with ethidium bromide. The results were 100% concordant with the human FPRP gene residing on human chromosome 1.

For regional chromosome mapping the above identified primers were used in a PCR based screening of megabase-insert Centre d'Etude du Polymorphisme Humaine (CEPH) yeast artificial chromosome (YAC) library (CEPH, Paris, France) DNA pools (Research Genetics, Huntsville, Ala.). For a description of the pooling scheme, see Berry et al. (1995) Nature Genet 10:415–423. A 6 ul aliquot of each YAC pool DNA was used in the 15 ul PCR reaction. For PCR amplification of human and yeast (Saccharomyces cerevisiae) genomic control DNAs, 40 ng of DNA was used. The PCR reaction mixture and cycling protocol were the same as for somatic hybrid mapping except for 1X Gibco buffer (Life Technologies, Gaithersburg, Md., pH 8.6) and 3.5 mM $MgCl_2$.

Two positive YACs (759_e_10 and 716_c_11) were identified, both of which have been mapped to the chromosome contig WC-513 (Whitehead Institute/MIT Center for Genome Research). Information on the characterization of the YAC clones was available from the Infoclone/Quickmap program or Genethon's World Wide Web Server (Cohen et al. (1993) Nature 366:698–701) and from the Whitehead Institute/MIT Center for Genome Research. The regional location for the fprp gene is estimated to be 1p13.1–q21.3. FIG. 11 shows an ideogram of chromosome 1 with the mapping site for the FPRP gene indicated. Notable, the prostaglandin $F_{2\alpha}$ receptor gene has also been mapped to chromosome 1 at 1p31.1. Other prostaglandin receptors map to chromosome 1, 5, and 19 (Duncan et al. (1995) Genomics 25:740–742).

The two positive human YACS, 759_e_10 and 716_c_11, were then obtained (Research Genetics, Huntsville, Ala.) and DNA was prepared from them (Mendez et al. (1994) In: Nelson D, Brownstein B (eds) YAC's: A Users Guide. Nelson/Freeman Publishers, pp 57–92). Following EcoRI digestion of the DNA from the YAC clones, agarose electrophoresis, Southern blotting and probing with random primed $\alpha[^{32}P]dCTP$ labeled rat exon 2, YAC 716_c_11 was chosen for further examination. YAC 716_c_11 DNA was then digested with EcoRI restriction enzyme, ligated to EcoRI predigested Lambda ZAP II arms (Strategene, LaJolla, Calif.), and packaged with Gigapack II packaging extract (Stratagene, LaJolla, Calif.) all according to manufacturers instructions. In this way a Lambda Zap II phage library was made of YAC 716_c_11. This library was screened using random primed, $\alpha[^{32}P]dCTP$ labeled rat exon 2 and 5 positive plaques were identified. A portion of the human genomic sequence surrounding and including exon 2 (FIG. 12) (SEQ ID NO:48) was produced by plaque purification, in vivo excision of the phagemid bluescript II with insert, identification of the appropriate portion of the insert (all according to manufacturers instructions) and single stranded sequencing (Sequenase 2.0 kit, both dG and 7-de-aza required, Amersham Life Science, Arlington Heights, Ill.).

TABLE 1

INHIBITION OF [$^3$H]PGF$_{2\alpha}$ SPECIFIC BINDING

| DNA TRANSFECTED | PROMOTER | % CONTROL |
|---|---|---|
| FP | CMV | 100 |
| FP + FPRP | SV40 | 30–50% |
| FP + pSG5 (vector only) | SV40 | 100 ± 3 |
| FP + pCMV6C (vector only) | CMV | 121 ± 4 |
| FP + pCDNA3 (vector only) | CMV | 135 ± 3 |
| FP + pSV2neo (vector only) | SV40 | 102 ± 6 |
| FP + Vitamin D receptor | CMV | 131 ± 7 |
| FP + Progesterone Receptor | SV40/metallothionein | 103 ± 5 |
| FP + βPDGF Receptor | SV40 | 90 ± 6 |
| FP + Prolactin Receptor | SV40 | 130 ± 7 |
| FP + bcl-2 | β-actin | 84 ± 5 |
| FP + crmA | β-actin | 141 ± 9 |
| FP + single chain IgG | CMV | 177 ± 15 |
| FP + TGN38 | CMV | 135 ± 6 |
| FP + α-1 Trypsin Inhibitor | SV40 | 141 ± 3 |
| FP + antisense FPRP | CMV | 100 ± 9 |

TABLE 2

FPRP INHIBITORY ACTIVITY

| CONDITIONS | % CONTROL [$^3$H]PGF$_{2\alpha}$ BINDING |
|---|---|
| Standard: | 30–50% |
| [$^3$H]PGF$_{2\alpha}$ binding assay pH | |
| 80% confluent cells | |
| post-electroporation cells grown at 40 µg/dish | |
| binding assay at 24 h post-electroporation | |
| Binding Buffers: | |
| standard buffer pH 6.0 | 41 ± 5 |
| standard buffer pH 7.0 | 45 ± 3 |
| Weipz et al. (1992) Biol. Reprod. 47:984–991, pH 6.0 | 53 ± 8 |
| Density of cells prior to electroporation: | |
| 100% confluent | 38 ± 4 |
| 80% confluent | 40 ± 5 |
| 60–70% confluent | 35 ± 3 |
| Density of cells post-electroporation: | |
| 60–80 µg/dish | 43 ± 4 |
| 40 µg/dish | 40 ± 5 |
| 20–30 µg/dish | 30 ± 5 |
| Time between electroporation and [$^3$H]PAGF$_{2\alpha}$ binding: | |
| 24 hr | 36 ± 3 |
| 48 hr | 33 ± 3 |

TABLE 3

% Control [$^3$H]PGF$_{2\alpha}$ Binding

| Conditioned Media | % Control [$^3$H]PGF$_{2\alpha}$ Binding |
|---|---|
| FP | 100 ± 11 |
| FP + FPRP | 43 ± 5 |
| (cotransfection pos. control) | |
| FP + 1:2 media from pSG5 transfection | 100 ± 6 |
| FP + 1:4 media from pSG5 transfection | 107 ± 4 |
| FP + 1:8 media from pSG5 transfection | 118 ± 3 |
| FP + 1:2 media from FPRP transfection | 103 ± 10 |
| FP + 1:4 media from FPRP transfection | 112 ± 10 |
| FP + 1:8 media from FPRP transfection | 113 ± 11 |
| CoCulture | |
| FP | 100 ± 3 |
| FP + FPRP | 45 ± 3 |
| (cotransfection positive control) | |
| FP + pSG5 1:1 | 136 ± 10 |
| FP + FPRP 1:1 | 120 ± 10 |

TABLE 4

Effect of Intracellular Messenger Altering Agents on FPRP Inhibition of [$^3$H]PGF$^{2\alpha}$ Binding

| Treatment | % Control [$^3$H]PGF$_{2\alpha}$ Binding | | |
|---|---|---|---|
| | FP + pSG5 | FP + FPRP | % Inhibition |
| Control (EtOH vehicle) | 100 ± 9 | 52 ± 3 | 48 |
| Phorbol 12-myristate 13-acetate 10$^{-8}$M | 105 ± 7 | 54 ± 3 | 50 |
| PGF$_{2\alpha}$ 10$^{-7}$m | 73 ± 9 | 40 ± 3 | 45 |
| PGE$_1$ 10$^{-7}$M | 100 ± 3 | 51 ± 3 | 49 |
| Calcium ionophore A23187 10$^{-6}$M | 102 ± 6 | 51 ± 6 | 50 |
| Okadaic acid 10$^{-6}$M | 94 ± 3 | 45 ± 3 | 52 |
| 8-Br-cAMP 10$^{-5}$M | 94 ± 6 | 52 ± 3 | 45 |
| Control | 100 ± 3 | 37 ± 3 | 63 |
| Brefeldin A 3 µg/ml, 2 h | 91 ± 3 | 27 ± 3 | 70 |
| Chloroquine 100 µM, 6 h | 91 ± 3 | 37 ± 3 | 59 |
| Tunicamycin 2.5 µg/ml, 20 h | 46 ± 3 | 23 ± 3 | 50 |

| Cotransfection | % Control [$^3$H]PGF$_{2\alpha}$ Binding |
|---|---|
| FP + pSG5 | 100 ± 3 |
| FP + FPRP | 37 ± 5 |
| FP + FPRP + pSG5 | 33 ± 5 |
| FP + FPRP + bcl-2 | 30 ± 3 |
| FP + FPRP + crmA | 29 ± 3 |
| FP + FPRP + α-1 trypsin inhibitor | 38 ± 3 |
| FP + FPRP + vitamin D receptor | 36 ± 3 |
| FP + FPRP + single chain Ig (secreted) | 39 ± 5 |
| Serum Removal: | |
| t = 1 h | 38 ± 7 |
| t = −6 h | 48 ± 4 |
| t = −21 h | 41 ± 3 |

What is claimed is:

1. An isolated nucleic acid molecule encoding a prostaglandin $F_{2\alpha}$ receptor regulatory protein (FPRP) comprising the amino acid sequence of SEQ ID NO:1.

2. The nucleic acid molecule of claim 1, wherein the nucleic acid molecule comprises the nucleotide sequence as set forth in SEQ ID NO:2.

3. An isolated nucleic acid molecule complementary to SEQ ID NO:2.

4. An isolated nucleic acid molecule selected from the group consisting of: SEQ ID NO.10, SEQ ID NO:11, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, and SEQ ID NO:24.

* * * * *